(12) United States Patent
Betenbaugh et al.

(10) Patent No.: US 6,949,372 B2
(45) Date of Patent: Sep. 27, 2005

(54) ENGINEERING INTRACELLULAR SIALYLATION PATHWAYS

(75) Inventors: Michael J. Betenbaugh, Baltimore, MD (US); Shawn Lawrence, Dobbs Ferry, NY (US); Yuan C. Lee, Timonium, MD (US); Timothy A. Coleman, Gaithersburg, MD (US)

(73) Assignees: The Johns Hopkins University, Baltimore, MD (US); Human Genome Sciences, Inc., Rockville, MD (US)

( * ) Notice: Subject to any disclaimer, the term of this patent is extended or adjusted under 35 U.S.C. 154(b) by 143 days.

(21) Appl. No.: 09/930,440

(22) Filed: Aug. 16, 2001

(65) Prior Publication Data

US 2002/0142386 A1 Oct. 3, 2002

Related U.S. Application Data

(62) Division of application No. 09/516,793, filed on Mar. 1, 2000, now abandoned.
(60) Provisional application No. 60/227,579, filed on Aug. 25, 2000, provisional application No. 60/169,624, filed on Dec. 8, 1999, and provisional application No. 60/122,582, filed on Mar. 2, 1999.

(51) Int. Cl.$^7$ .............................. C12N 9/00; C12N 9/10; C07H 21/04
(52) U.S. Cl. ............................... 435/193; 435/4; 435/6; 435/69.1; 435/183; 435/252.3; 435/320.1; 536/23.2; 536/23.4; 536/23.5; 536/23.7; 530/350
(58) Field of Search .............................. 435/4, 6, 69.1, 435/183, 193, 252.3, 320.1, 41, 72, 71.1, 71.2, 232, 254.1, 255.1, 325, 348, 410, 233, 15–30; 536/23.2–23.7

(56) References Cited

U.S. PATENT DOCUMENTS

| | | |
|---|---|---|
| 5,593,887 A | 1/1997 | Wong et al. |
| 5,962,302 A | 10/1999 | Hillman et al. |
| 6,030,824 A | 2/2000 | Hillman et al. |

FOREIGN PATENT DOCUMENTS

| | | |
|---|---|---|
| WO | WO 98/06835 | 2/1998 |
| WO | WO 00/05378 | 2/2000 |
| WO | WO 00/52135 | 9/2000 |
| WO | WO 00/52136 | 9/2000 |
| WO | WO 01/42492 | 6/2001 |

OTHER PUBLICATIONS

European Search Report dated Jul. 11, 2002.*
European Search Report dated Jun. 10, 2002.*
Munster et al., "Mammalian cytidine 5'–monophosphate N–acetylneuraminic acid synthetase: A nuclear protein with evolutionarily conserved structural motifs", Proc. Natl. Acad. Sci. 95:9140–9145 (1998).*
Kean, E.L., "Mini Review Sialic Acid Activation", Glycobiology, 1(5):441–447 (1991).*
Kolisis, F.N., "Studies on Acylneuraminate Cytidylytransferase from Human Placenta" Archives Internationales de Physiologie et de Biochimie 92:179–184 (1984).*
Gu et al., "Improvement of Interferoy–$\gamma$ Sialylation in Chinese Hamster Ovary Culture by Feeding of N–Acetylmannosamine", Biotechnology and Bioengineering 58(6):642–648 (1998).*
Ogonah et al., "Isolation and Characterization of an Insert Cell Line Able to Perform Complex N–Linked Glycosylation on Recombinant Proteins" Biotechnology 14:197–202 (1996).*
Munster, A–K., et al., "Mammalian cytidin 5'–monophosphate N–acetylneuraminic acid synthetase: A nuclear protein with evolutionary conserved structural motifs", Proc. Natl. Acad. Sci. USA, vol. 95, pp. 9140–9145 (Aug. 1998).
Redenbach, M., et al., "A set of ordered cosmids and a detailed genetic and physical map for the 8 Mb Streptomyces coelicolor A3(2) chromosome", Mol. Microbiol., vol. 21, No. 1, pp. 77–96 (Jul. 1996).
Sakakibara et al., Constructions and expression of human aldolase A and B expression plasmids in *Escherichia coli* host, Biochimica et Biophysica Acta, 1007:334–342 (1989).
Lubineau et al., "Combined Chemical and Enzymatic Synthesis of the Sialylated Non Reducing Terminal Sequence of $GM_{1b}$ Glycolylated Ganglioside, a Potential Human Tumor Marker," *Bioorganic & Medicinal Chemistry* 2(7):669–674 (1994).
International Preliminary Examination Report mailed on Aug. 22, 2001, in corresponding International Application No. PCT/US00/05313.
International Search Report mailed on Jun. 20, 2000, in corresponding International Application No. PCT/US00/05313.
Fussenegger et al. "Genetic optimization of recombinant glycoprotein production by mammalian cells," *TIBS* 17:35–42 (1999).

(Continued)

*Primary Examiner*—Manjunath N. Rao
(74) *Attorney, Agent, or Firm*—Whitham, Curtis & Christofferson, PC

(57) ABSTRACT

Methods for manipulating carbohydrate processing pathways in cells of interest are provided. Methods are directed at manipulating multiple pathways involved with the sialylation reaction by using recombinant DNA technology and substrate feeding approaches to enable the production of sialylated glycoproteins in cells of interest. These carbohydrate engineering efforts encompass the implementation of new carbohydrate bioassays, the examination of a selection of insect cell lines and the use of bioinformatics to identify gene sequences for critical processing enzymes. The compositions comprise cells of interest producing sialylated glycoproteins. The methods and compositions are useful for heterologous expression of glycoproteins.

98 Claims, 40 Drawing Sheets

OTHER PUBLICATIONS

Shames et al. "CMP–N–acetylneuraminic acid synthase of *E. coli*: high level expression purification and use in the enzymatic synthesis of CMP–N–acetylneuraminic acid and CMP–neuraminic acid derivatives," *Glycobiology* 1:187–191 (1991).

Murhammer et al. "Review and Patents and Literature: The use of insect cell cultures for recombinant protein synthesis: engineering aspects," *Appl. Biochem. Biotech.* 31:283–310 (1991).

Yang et al.. "Human transferrin: cDNA characterization and the chromosomal localization," *PNAS USA* 81:2752–2756 (1984).

Sakakibara et al. "Nucleotide sequence of a cDNA clone for human aldolase; a mRNA in the liver," *Biochem. Biophys. Res. Commun.* 131(1):413–420 (1985).

Gonzalez et al. "Identification, expression, and characterization of a cDNA encoding human endoplasmic reticulum mannosidase I, the enzyme that catalyzes the first mannose trimming step in mammalian Asn–linked oligosaccharide biosynthesis," *J. Biol. Chem.* 274(30):21375–21386 (1999).

Rodriguez–Aparicio, et al. "Purification and Characterization of the Nuclear Cytidine 5'Monophosphate N–Acetylneuraminic Acid Synthetase from Rat Liver" *J. Biol. Chem.* 267(13):9257–9263 (1992).

International Search Report mailed on Apr. 30, 2001, in related International Application No. PCT/US00/33136.

Ganguli et al., *Journal of Bacteriology*, 176(15):4583–4589 (1994).

Gilbert et al., *Journal of Biological Chemistry*, 275(6):3896–3906 (2000).

Weikert et al., *Nature Biotechnology*, 17:1116–1121 (1999).

* cited by examiner

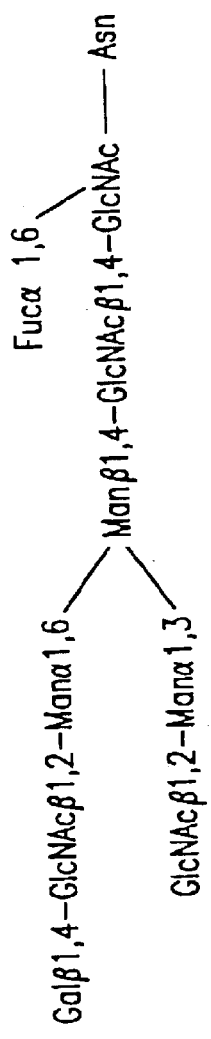

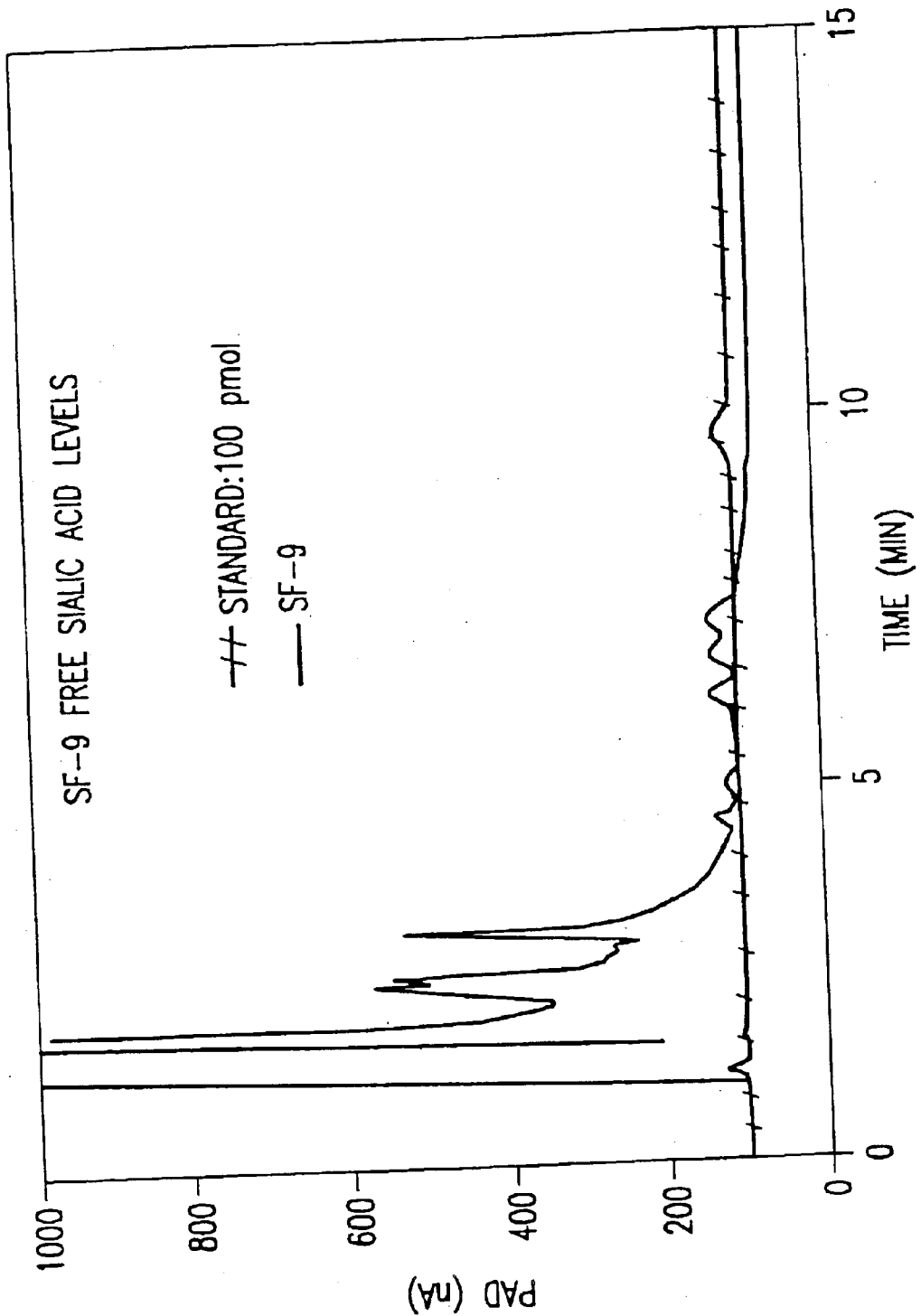

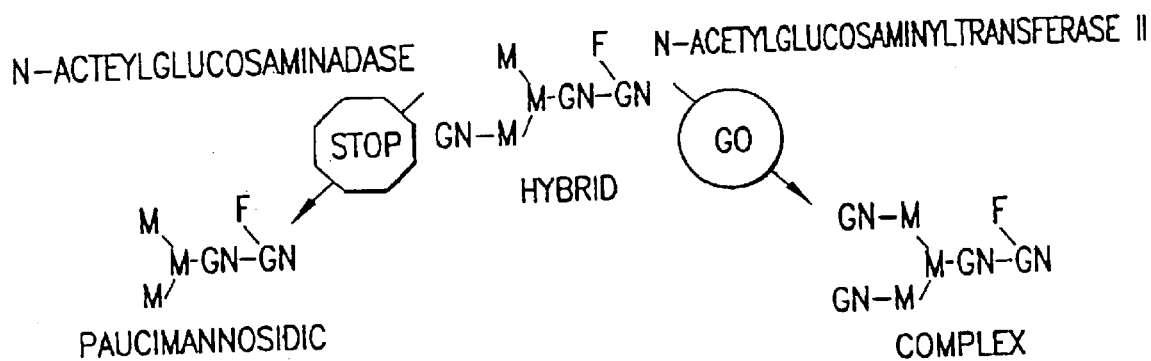
FIG. 17
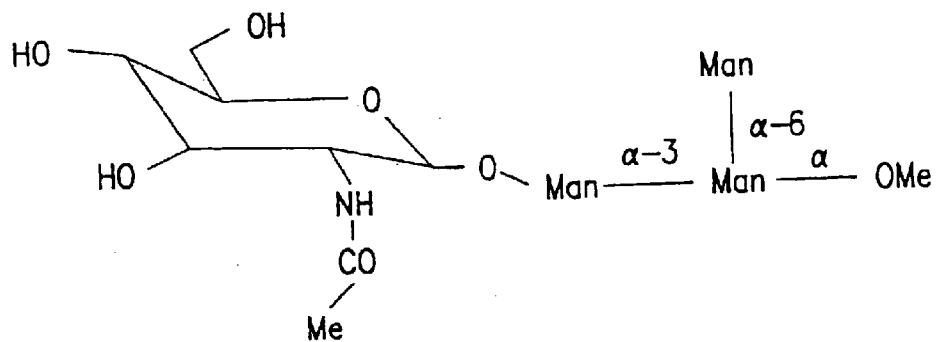
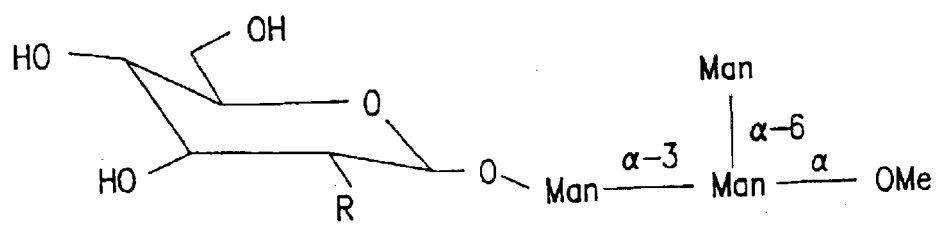
R=MeCONH      II
R=BrCH2CONH   III
R=N2CH2CONH   IV
FIG. 19

CMP-SIALIC ACID

```
ATGGCCTTCCCAAAGAAGAAACTTCAGGGTCTTGTGGCTGCAACCATCACGCCAATGACTGAGAATGGAGAAATCAA
CTTTTCAGTAATTGGTCAGTATGTGGATTATCTTGTGAAAGAACAGGGAGTGAAGAACATTTTTGTGAATGGCACAA
CAGGAGAAGGCCTGTCCCTGAGCGTCTCAGAGCGTCGCCAGGTTGCAGAGGAGTGGGTGACAAAAGGGAAGGACAAG
CTGGATCACGTGATAATTCACGTAGGAGCACTGAGCTTGAAGGAGTCACAGGAACTGGCCCAACATGCAGCAGAAAT
AGGAGCTGATGGCATCGCTGTCATTGCACCGTTCTTCCTCAAGCCATGGACCAAAGATATCCTGATTAATTTCCTAA
AGGAAGTGGCTCCTGCCGCCCCTGCCCTGCCATTTTATTACTATCACATTCCTGCCTTGACAGGGGTAAAGATTCGT
GCTGAGGAGTTGTTGGATGGGATTCTGGATAAGATCCCCACCTTCCAAGGGCTGAAATTCAGTGATACAGATCTCTT
AGACTTCGGGCAATGTGTTGATCAGAATCGCCAGCAACAGTTTGCTTTCCTTTTTGGGGTGGATGAGCAACTGTTGA
GTGCTCTGGTGATGGGAGCAACTGGAGCAGTGGGCAGTTTTGTATCCAGAGATTTATCAACTTTGTTGTCAAACTAG
GTTTTGGACTGTCACAGACCAAAGCCATCATGACTCTGGTCTCTGGGATTCCAATGGGCCCACCCCGGCTTCCACTG
CAGAAAGCCTCCAGGCAGTTTACTGATAGTGCTGAAGCTAAACTGAAGAGCCTGGATTTCCTTTCTTTCACTGATTT
AAAGGATGGAAACTTGGAAGCTGGTAGCTAGTGCCTCTCTATCAAATCAGGGTTTGCACCTTGAGACATAATCTACC
TTAAATAGTGCATTTTTTTCTCAGGGAATTTTAGATGAACTTGAATAAACTCTCCTAGCAAATGAAATCTCACAATA
AGCATTGAGGTACCTTTTGTGAGCCTTAAAAAGTCTTATTTTGTGAAGGGGCAAAAACTCTAGGAGTCACAACTCTC
AGTCATTCATTTCACAGATTTTTTTGTGGAGAAATTTCTGTTTATATGGATGAAATGGAATCAAGAGGAAAATTGTA
ATTGATTAATTCCATCTGTCTTTAGGAGCTCTCATTATCTCGGTCTCTGGTTCCTAATCCTATTTTAAAGTTGTCTA
ATTTTAAACCACTATAATATGTCTTCATTTTAATAAATATTCATTTGGAATCTAGGAAAACTCTGAGCTACTGCATT
TAGGCAGGCACTTTAATACCAAACTGTAACATGTCTCAACTGTATACAACTCAAAATACACCAGCTCATTTGGCTGC
TCAGTCTAACTCTAGAATGGATGCTTTTGAATTCATTTCGATG
```

FIG.27

MAFPKKKLQGLVAATITPMTENGEINFSVIGQYVDYLVKEQGVKNIFVNGTTGEGLSLSVSERRQVAEEWVTKGKDKLDQ
VIIHVGALSLKESQELAQHAAEIGADGIAVIAPFFLKPWTKDILINFLKEVAAAAPALPFYYYHIPALTGVKIRAEELLD
GILDKIPTFQGLKFSDTDLLDFGQCVDQNRQQQFAFLFGVDEQLLSALVMGATGAVGSFVSRDLSTLLSN.VLECHRPKP
S.LWSLGFQWAHPGFHCRKPPGSLLIVLKLN.RAWISFLSLI.RMETWKLVASASLSNQGFAPLRHNL

FIG. 28

ATGGACTCGGTGGAGAAGGGGGCCGCCACCTCCGTCTCCAACCCGCGGGGGCGACCGTCCCGGGGCCGGCCGCCGAAGCT
GCAGCGCAACTCTCGCGGCGGCCAGGGCCGAGGTGTGGAGAAGCCCCCGCACCTGGCAGCCCTAATTCTGGCCCCGGGAG
GCAGCAAAGGCATCCCCCTGAAGAACATTAAGCACCTGGCGGGGGTCCCGCTCATTGGCTGGGTCCTGCGTGCGGCCCTG
GATTCAGGGGCCTTCCAGAGTGTATGGGTTTCGACAGACCATGATGAAATTGAGAATGTGGCCAAACAATTTGGTGCACA
AGTTCATCGAAGAAGTTCTGAAGTTTCAAAAGACAGCTCTACCTCACTAGATGCCATCATAGAATTTCTTAATTATYATA
ATGAGGKTGACATTGTAGGAAATATTCAAGCTACTTCTYCATGTTTACATCCTACTGATCTTCAAAAAGTTGCAGAAATG
ATTCGAGAAGAACGATATGATTCTGKTTTCTCTGTTGTGAGACGCCATCAGTTTCGATGGAGTGAAATTCAGAAGGAGT
TCGTGAAGTGACCGAACCTCTGAATTTAAATCCAGCTAAACGGCCTCGTCGACAAGACTGGGATGGAGAATTATATGAAA
ATGGCTCATTTTATTTTGCTAAAAGACATTTGATAGAGATGGGTTACTTGCAGGGTGGAAAATGGCATACTACGAAATGC
GAGCTGGAACATAGTGTGGATATAGATGTGGATATTGATTGGCCTATTGCAGAGCAAAGAGTATTAAGATATGGCTATTT
TGGCAAAGAGAAGCTTAAGGAAATAAAACTTTTGCTTTGCAATATTGATGGATGTCTCACCAATGGCCACATTTATGTAT
CAGGAGACCAAAAAGAAATAATATCTTATGATGTAAAAGATGCTATTGGGATAAGTTTATTAAAGAAAAGTGGTATTGAG
GTGAGGCTAATCTCAGAAAGGGCCTGTTCAAAGCAGACGCTGTCTTCTTTAAAACTGGATTGCAAAATGGAAGTCAGTGT
ATCAGACAAGCTAGCAGTTGTAGATGAATGGAGAAAAGAAATGCCCCTGTGCTGGAAAGAAGTGGCATATCTTGGAAATG
AAGTGTCTGATGAAGAGTGCTTGAAGAGAGTGGGCCTAAGTGGCGCTCCTGCTGATGCCTGTTCCTACGCCCAGAAGGCT
GTTGGATACATTTGCAAATGTAATGGTGGCCGTGGTGCCATCCGAGAATTTGCAGAGCACATTTGCCTACTAATGGAAAA
AGTTAATAATTCATGCCAAAAATAG

FIG. 29

MDSVEKGAATSVSNPRCRPSRGRPPKLQRNSRGGQGRGVEKPPHLAALILARGGSKGIPLKNIKHLACVPLIGWVLRAAL
DSGAFQSVWVSTDHDEIENVAKQFGAQVHRRSSEVSKDSSTSLDAIIEFLNYXNEXDIVGNIQATSXCLHPTDLQKVAEM
IREEGYDSXFSVVRRHQFRWSEIQKGVREVTEPLNLNPAKRPRRQDWDGELYENGSFYFAKRHLIEMGYLQCGKWHTTKC
ELEHSVDIDVDIDWPIAEQRVLRYGYFGKEKLKEIKLLVCNIDGCLTNGHIYVSGDQKEIISYDVKDAIGISLLKKSGIE
VRLISERACSKQTLSSLKLDCKMEVSVSDKLAVVDEWRKEMGLCWKEVAYLGNEVSDEECLKRVGLSGAPADACSYAQKA
VGYICKCNGGRGAIREFAEHICLLMEKVNNSCQK.

FIG. 30

ATGCCGCTGGAGCTGGAGCTGTGTCCCGGGCGCTGGGTGGGCGGGCAACACCCGTGCTTCATCATTGCCGAGATCGGCCA
GAACCACCAGGGCGACCTGGACGTAGCCAAGCGCATGATCCGCATGGCCAAGGAGTGTGGGGCTGATTGTGCCAAGTTCC
AGAAGAGTGAGCTAGAATTCAAGTTTAATCGGAAAGCCTTGGAGAGGCCATACACCTCGAAGCATTCCTGGGGGAAGACG
TACGGGGAGCACAAACGACATCTGGAGTTCAGCCATGACCAGTACAGGGAGCTGCAGACGTACGCCGAGGAGGTTGGGAT
CTTCTTCACTGCCTCTGGCATGGATGAGATGGCAGTTGAATTCCTGCATGAACTGAATGTTCCATTTTTCAAAGTTGGAT
CTGGAGACACTAATAATTTTCCTTATCTGGAAAAGACAGCCAAAAAAGGTCGCCCAATGGTGATCTCCAGTGGGATGCAG
TCAATGGACACCATGAAGCAAGTTTATCAGATCGTGAAGCCCCTCAACCCCAACTTCTGCTTCTTGCAGTGTACCAGCGC
ATACCCGCTCCAGCCTGAGGACGTCAACCTGCGGGTCATCTCGGAATATCAGAAGCTCTTTCCTGACATTCCCATAGGGT
ATTCTGGGCATGAAACAGGCATAGCGATATCTGTGGCCGCAGTGGCTCTGGGGGCCAAGGTGTTGGAACGTCACATAACT
TTGGACAAGACCTGGAAGGGGAGTGACCACTCGGCCTCGCTGGAGCCTGGAGAACTGGCCGAGCTGGTGCGGTCAGTGCG
TCTTGTGGAGCCTGCCCTGGGCTCCCCAACCAAGCAGCTGCTGCCCTGTGAGATGGCCTGCAATGAAGCTGGGCAAGT
CTGTGGTGGCCAAAGTGAAAATTCCGGAAGGCACCATTCTAACAATGGACATGCTCACCGTGAAGGTGGGTGAGCCCAAA
GCCTATCCTCCTGAAGACATCTTTAATCTAGTGGGCAAGAAGGTCCTGGTCACTGTTGAAGAGGATGACACCATCATGGA
AGAATTGGTAGATAATCATGGCAAAAAAATCAAGTCTTAA

FIG.31

MPLELELCPGRWVGGQHPCFIIAEIGQNHQGDLDVAKRMIRMAKECGADCAKFQKSELEFKFNRKALERPYTSKHSWGKT
YGEHKRHLEFSHDQYRELQRYAEEVGIFFTASGMDEMAVEFLHELNVPFFKVGSGDTNNFPYLEKTAKKGRPMVISSGMQ
SMDTMKQVYQIVKPLNPNFCFLQCTSAYPLQPEDVNLRVISEYQKLFPDIPIGYSGHETGIAISVAAVALGAKVLERHIT
LDKTWKGSDHSASLEPGELAELVRSVRLVERALGSPTKQLLPCEMACNEKLGKSVVAKVKIPEGTILTMDMLTVKVGEPK
AYPPEDIFNLVGKKVLVTVEEDDTIMEELVDNHGKKIKS

FIG.32

| Peak/code (G.U. ODS, amide) | PA-oligosaccharide structure | Secreted hTf (mol%) −GalT | +GalT |
|---|---|---|---|
| A/M8.1 (4.9,9.0) | Manα2−Manα6\\Manα6\\Manβ4−GlcNAcβ4−GlcNAc<br>Manα3/<br>Manα2−Manα2−Manα3/ | 3.9 | 10.1 |
| B1/M7.2 (5.1,8.1) | Manα2−Manα6\\Manα6\\Manβ4−GlcNAcβ4−GlcNAc<br>Manα3/<br>Manα2−Manα2−Manα3/ | 2.3 | 5.5 |
| B2/M9.1 (5.2,9.7) | Manα2−Manα6\\Manα6\\Manβ4−GlcNAcβ4−GlcNAc<br>Manα3/<br>Manα2−Manα2−Manα3/ | 11.6 | 23.5 |
| C/M7.1 (5.8,8.0) | Manα6\\Manα6\\Manβ4−GlcNAcβ4−GlcNAc<br>Manα3/<br>Manα2−Manα2−Manα3/ | 2.3 | 5.5 |
| D/M6.1 (6.1,7.1) | Manα6\\Manα6\\Manβ4−GlcNAcβ4−GlcNAc<br>Manα3/<br>Manα2−Manα2−Manα3/ | 4.7 | 13.4 |

| Peak/code (G.U. ODS, amide) | PA-oligosaccharide structure | Secreted hTf (mol%) −GalT | +GalT |
|---|---|---|---|
| E1/M9.2 (6.3,10.3) | Manα2–Manα6\Manα6\Manβ4–GlcNAcβ4–GlcNAc<br>Manα2–Manα3/<br>Glcα3–Manα2–Manα2–Manα3/ | 1.3 | 3.7 |
| E2/M8.2 (6.4,8.5) | Manα6\Manα6\Manβ4–GlcNAcβ4–GlcNAc<br>Manα2–Manα3/<br>Manα2–Manα2–Manα3/ | 0.3 | 0.8 |
| F1/M5.1 (7.2,6.2) | Manα6\Manα6\Manβ4–GlcNAcβ4–GlcNAc<br>Manα3/<br>Manα3/ | 4.6 | 2.4 |
| F2/000.1 (7.4,4.3) | Manα6\Manβ4–GlcNAcβ4–GlcNAc<br>Manα3/ | 9.0 | 5.8 |
| F3/100.2 (7.4,4.7) | Manα6\Manβ4–GlcNAcβ4–GlcNAc<br>GlcNAcβ2–Manα3/ | 6.5 | 3.1 |
| G1/M6.10 (7.9,6.8) | Manα6\Manα6\Manβ4–GlcNAcβ4–GlcNAc<br>Manα2–Manα3/<br>Manα3/ | 1.1 | 1.1 |

| Peak/code (G.U. ODS, amide) | PA-oligosaccharide structure | Secreted hTf (mol%) −GalT | +GalT |
|---|---|---|---|
| G2/100.4 (8.0,5.7) | Galb4−GlcNAcb2−Mana3<br>Manα6\Manb4−GlcNAcb4−GlcNAc | nd | 5.0 |
| H/000.1FF (8.5,5.5) | Manα6\Manb4−GlcNAcb4−GlcNAc (Fucα6, Fucα3)<br>Manα3/ | 5.9 | 1.7 |
| I/100.4FF (8.9,7.0) | Galb4−GlcNAcb2−Mana3<br>Manα6\Manb4−GlcNAcb4−GlcNAc (Fucα6, Fucα3) | nd | 1.3 |
| J1/010.0 (7.2,6.2) | Manα6\Manb4−GlcNAcb4−GlcNAc (Fucα6)<br>Manα3/ | 23.4 | 4.0 |
| J2/010.1 (10.2,4.7) | Manα6\Manb4−GlcNAcb4−GlcNAc (Fucα6)<br>Manα3/ | 15.7 | 6.1 |

FIG. 33C

| Peak/code (G.U. ODS, amide) | PA-oligosaccharide structure | Secreted hTf (mol%) −GalT | +GalT |
|---|---|---|---|
| J3/110.2 (10.2,5.1) | Manα6⟍Manβ4−GlcNAcβ4−GlcNAc<br>GlcNAcb2−Manα3⟋    Fucα6 (on GlcNAc) | 3.5 | nd |
| K/110.4 (10.9,6.3) | Manα6⟍Manβ4−GlcNAcβ4−GlcNAc<br>Galb4−GlcNAcb2−Manα3⟋    Fucα6 | nd | 4.3 |
| L/110.1 (12.7,5.1) | GlcNAcb2−Manα6⟍Manβ4−GlcNAcβ4−GlcNAc<br>Manα3⟋    Fucα6 | 3.9 | 0.7 |

FIG.33D

```
                  10           20           30           40           50           60
                   .            .            .            .            .            .
  1  CGG ACC CAG ACT GGT AGT GCA GGC TTT GGA CCC CGA GCC GCT GCA ATG CCG CTG GAG CTG  60
  1                                                                  M   P   L   E   L   5
                  70           80           90          100          110          120
                   .            .            .            .            .            .
 61  GAG CTG TGT CCC GGG CGC TGG GTG GGC GGG CAA CAC CCG TGC TTC ATC ATT GCC GAG ATC 120
  6   E   L   C   P   G   R   W   V   G   G   Q   H   P   C   F   I   I   A   E   I  25
                 130          140          150          160          170          180
                   .            .            .            .            .            .
121  GGC CAG AAC CAC CAG GGC GAC CTG GAC GTA GCC AAG CGC ATG ATC CGC ATG GCC AAG GAG 180
 26   G   Q   N   H   Q   G   D   L   D   V   A   K   R   M   I   R   M   A   K   E  45
                 190          200          210          220          230          240
                   .            .            .            .            .            .
181  TGT GGG GCT GAT TGT GCC AAG TTC CAG AAG AGT GAG CTA GAA TTC AAG TTT AAT CGG AAA 240
 46   C   G   A   D   C   A   K   F   Q   K   S   E   L   E   F   K   F   N   R   K  65
                 250          260          270          280          290          300
                   .            .            .            .            .            .
241  GCC TTG GAG AGG CCA TAC ACC TCG AAG CAT TCC TGG GGG AAG ACG TAC GGG GAG CAC AAA 300
 66   A   L   E   R   P   Y   T   S   K   H   S   W   G   K   T   Y   G   E   H   K  85
                 310          320          330          340          350          360
                   .            .            .            .            .            .
301  CGA CAT CTG GAG TTC AGC CAT GAC CAG TAC AGG GAG CTG CAG AGG TAC GCC GAG GAG GTT 360
 86   R   H   L   E   F   S   H   D   Q   Y   R   E   L   Q   R   Y   A   E   E   V 105
                 370          380          390          400          410          420
                   .            .            .            .            .            .
361  GGG ATC TTC TTC ACT GCC TCT GGC ATG GAT GAG ATG GCA GTT GAA TTC CTG CAT GAA CTG 420
106   G   I   F   F   T   A   S   G   M   D   E   M   A   V   E   F   L   H   E   L 125
                 430          440          450          460          470          480
                   .            .            .            .            .            .
421  AAT GTT CCA TTT TTC AAA GTT GGA TCT GGA GAC ACT AAT AAT TTT CCT TAT CTG GAA AAG 480
126   N   V   P   F   F   K   V   G   S   G   D   T   N   N   F   P   Y   L   E   K 145
```

FIG. 35A

```
              490         500         510         520         530         540
               .           .           .           .           .           .
481 ACA GCC AAA AAA GGT CGC CCA ATG GTG ATC TCC AGT GGG ATG CAG TCA ATG GAC ACC ATG 540
146  T   A   K   K   G   R   P   M   V   I   S   S   G   M   Q   S   M   D   T   M  165
              550         560         570         580         590         600
               .           .           .           .           .           .
541 AAG CAA GTT TAT CAG ATC GTG AAG CCC CTC AAC CCC AAC TTC TGC TTC TTG CAG TGT ACC 600
166  K   Q   V   Y   Q   I   V   K   P   L   N   P   N   F   C   F   L   Q   C   T  185
              610         620         630         640         650         660
               .           .           .           .           .           .
601 AGC GCA TAC CCG CTC CAG CCT GAG GAC GTC AAC CTG CGG GTC ATC TCG GAA TAT CAG AAG 660
186  S   A   Y   P   L   Q   P   E   D   V   N   L   R   V   I   S   E   Y   Q   K  205
              670         680         690         700         710         720
               .           .           .           .           .           .
661 CTC TTT CCT GAC ATT CCC ATA GGG TAT TCT GGG CAT GAA ACA GGC ATA GCG ATA TCT GTG 720
206  L   F   P   D   I   P   I   G   Y   S   G   H   E   T   G   I   A   I   S   V  225
              730         740         750         760         770         780
               .           .           .           .           .           .
721 GCC GCA GTG GCT CTG GGG GCC AAG GTG TTG GAA CGT CAC ATA ACT TTG GAC AAG ACC TGG 780
226  A   A   V   A   L   G   A   K   V   L   E   R   H   I   T   L   D   K   T   W  245
              790         800         810         820         830         840
               .           .           .           .           .           .
781 AAG GGG AGT GAC CAC TCG GCC TCG CTG GAG CCT GGA GAA CTG GCC GAG CTG GTG CGG TCA 840
246  K   G   S   D   H   S   A   S   L   E   P   G   E   L   A   E   L   V   R   S  265
              850         860         870         880         890         900
               .           .           .           .           .           .
841 GTG CGT CTT GTG GAG CGT GCC CTG GGC TCC CCA ACC AAG CAG CTG CTG CCC TGT GAG ATG 900
266  V   R   L   V   E   R   A   L   G   S   P   T   K   Q   L   L   P   C   E   M  285
              910         920         930         940         950         960
               .           .           .           .           .           .
901 GCC TGC AAT GAG AAG CTG GGC AAG TCT GTG GTG GCC AAA GTG AAA ATT CCG GAA GGC ACC 960
286  A   C   N   E   K   L   G   K   S   V   V   A   K   V   K   I   P   E   G   T  305
```

FIG. 35B

```
              970         980         990        1000        1010        1020
               .           .           .           .           .           .
961 ATT CTA ACA ATG GAC ATG CTC ACC GTG AAG GTG GGT GAG CCC AAA GCC TAT CCT CCT GAA 1020
306  I   L   T   M   D   M   L   T   V   K   V   G   E   P   K   A   Y   P   P   E  325
              1030        1040        1050        1060        1070        1080
               .           .           .           .           .           .
1021 GAC ATC TTT AAT CTA GTG GGC AAG AAG GTC CTG GTC ACT GTT GAA GAG GAT GAC ACC ATC 1080
326  D   I   F   N   L   V   G   K   K   V   L   V   T   V   E   E   D   D   T   I  345
              1090        1100        1110        1120        1130        1140
               .           .           .           .           .           .
1081 ATG GAA GAA TTG GTA GAT AAT CAT GGC AAA AAA ATC AAG TCT TAA AAA TAA AGT GCC ATT 1140
346  M   E   E   L   V   D   N   H   G   K   K   I   K   S   *                       359

1141 CTC TGA 1146
```

FIG. 35C

```
  1 MPLELELCPGRWVGGQHPCFIIAEIGQNHQGDLDVAKRMIRMAKECGADCAKFQKSELEF
    |             ||||  ||  |  ||  ||   ||| |          |||
  1 MS-------------NIYIVAEIGCNHNGSVDIAREMILKAKEAGVNAVKFQTFKADK

61 KFNRKALERPYTSKHSWG-KTYGEHKRHLEFSHDQYRELQRYAEEVGIFFTASGMDEMAV
      |   |           |   ||    ||  | |  ||                 ||
 46 LISAIAPKAEYQIKNTGELESQLEMTKKLEMKYDDYLHLMEYAVSLNLDVFSTPFDEDSI

120 EFLHELNVPFFKVGSGDTNNFPYLEKTAK---KGRPMVISSGMQSMDTMKQ---VYQIVK
    ||  |    |  ||   | ||||||  ||      || ||   |  | ||            |
106 DFLASLKQKIWKIPSGELLNLPYLEKIAKLPIPDKKIIISTGMATIDEIKQSVSIFINNK

174 PLNPNFCFLQCTSAYPLQPEDVNLRVISEYQKLFPDIPIGYSGHETGIAISVAAVALGAK
      |  |   ||  ||||| |  | ||  |  ||  ||| | |      ||| |
166 VPVGNITILHCNTEYPTPFEDVNLNAINDLKKHFPKNNIGFSDHSSGFYAAIAAVPYGIT

234 VLERHITLDKTWKGSDHSASLEPGELAELVRSVRLVERALGSPTKQLLPCEMACNEKLGK
    | |||   | || ||  ||    | || |||   |                |
226 FIEKHFTLDKSMSGPDHLASIEPDELKHLCIGVRCVEKSLGSNSKVVTASERKNKIVARK

294 SVVAKVKIPEGTILTMDMLTVKVGEPKAYPPEDIFNLVGKKVLVTVEEDDTIMEELVDNH
    |  ||  |      ||     |     ||||    |  |||     |   ||
286 SIIAKTEIKKGEVFSEKNITTKRP-GNGISPMEWYNLLGK-----IAEQDFIPDELIIHS

354 G-KKIKS
    |
340 EFKNQGE
```

FIG. 35D

ENGINEERING INTRACELLULAR SIALYLATION PATHWAYS

This application claims benefit of U.S. Provisional Application Ser. No. 60/227,579, filed Aug. 25, 2000, which is herein incorporated by reference in its entirety, and also claims benefit of and is a divisional of U.S. application Ser. No. 09/516,793, filed Mar. 1, 2000, now abandoned, which is herein incorporated by reference in its entirety and which claims benefit of U.S. Provisional Applications Nos. 60/169,624, filed Dec. 8, 1999, and 60/122,582, filed Mar. 2, 1999, both of which are herein incorporated by reference in their entireties.

Part of the work performed during the development of this invention utilized U.S. Government funds in the form of grants from the National Science Foundation, Grant Numbers BES9814157, BES9814100, and the National Institutes of Health, Grant Number RO1-GM-49734. The U.S. Government has certain rights in this invention.

FIELD OF THE INVENTION

The invention relates to methods and compositions for expressing sialylated glycoproteins in heterologous expression systems, particularly insect cells.

BACKGROUND OF THE INVENTION

While heterologous proteins are generally identical at the amino acid level, their post-translationally attached carbohydrate moieties often differ from the carbohydrate moieties found on proteins expressed in their natural host species. Thus, carbohydrate processing is specific and limiting in a wide variety of organisms including insect, yeast, mammalian, and plant cells.

The baculovirus expression vector has promoted the use of insect cells as hosts for the production of heterologous proteins (Luckow et al. (1993) *Curr. Opin. Biotech.* 4:564–572, Luckow et al. (1995) *Protein production and processing from baculovirus expression vectors*). Commercially available cassettes allow rapid generation of recombinant baculovirus vectors containing foreign genes under the control of the strong, polyhedrin promoter. This expression system is often used to produce heterologous secreted and membrane-bound glycoproteins normally of mammalian origin.

However, post-translational processing events in the secretory apparatus of insect cells yield glycoproteins with covalently-linked oligosaccharide attachments that differ significantly from those produced by mammalian cells. While mammalian cells often generate complex oligosaccharides terminating in sialic acid (SA), insect cells typically produce truncated (paucimannosidic) and hybrid structures terminating in mannose (Man) or N-acetylglucosamine (GlcNAc) (FIG. 1). The inability of insect cell lines to generate complex carbohydrates comprising sialic acid significantly limits the wider application of this expression system.

The carbohydrate composition of an attached oligosaccharide, especially sialic acid, can affect a glycoprotein's solubility, structural stability, resistance to protease degradation, biological activity, and in vivo circulation (Goochee et al. (1991) *Bio/technology* 9:1347–1355, Cumming et al. (1991) *Glycobiology* 1:115–130, Opdenakker et al. (1993) *FASEB J.* 7:1330, Rademacher et al. (1988) *Ann. Rev. Biochem.*, Lis et al. (1993) *Eur. J. Biochem.* 218:1–27). The terminal residues of a carbohydrate are particularly important for therapeutic proteins since the final sugar moiety often controls its in vivo circulatory half-life (Cumming et al (1991) *Glycobiology* 1:115–130). Glycoproteins with oligosaccharides terminating in sialic acid typically remain in circulation longer due to the presence of receptors in hepatocytes and macrophages that bind and rapidly remove structures terminating in mannose (Man), N-acetylglucosamine (GlcNAc), and galactose (Gal), from the bloodstream (Ashwell et al. (1974) *Giochem. Soc. Symp.* 40:117–124, Goochee et al. (1991) *Bio/technology* 9:1347–1355, Opdenakker et al. (1993) *FASEB J.* 7:1330). Unfortunately, Man and GlcNAc are the residues most commonly found on the termini of glycoproteins produced by insect cells. The presence of sialic acid can also be important to the structure and function of a glycoprotein since sialic acid is one of the few sugars that is charged at physiological pH. The sialic acid residue is often involved in biological recognition events such as protein targeting, viral infection, cell adhesion, tissue targeting, and tissue organization (Brandley et al. (1986) *J. of Leukocyte bio.* 40:97–111, Varki et al. (1997) *FASEB* 11:248–255, Goochee et al. (1991) *Bio/technology* 9:1347–1355, Lopez et al. (1997) *Glycobiology* 7:635–651, Opdenakker et al. (1993) *FASEB J.* 7:1330).

The composition of the attached oligosaccharide for a secreted or membrane-bound glycoprotein is dictated by the structure of the protein and by the post-translational processing events that occur in the endoplasmic reticulum and Golgi apparatus of the host cell. Since the secretory processing machinery in mammalian cells differs from that in insect cells, glycoproteins with very different carbohydrate structures are produced by these two host cells (Jarvis et al. (1995) *Virology* 212:500–511, Maru et al. (1996) *J. Biol. Chem.* 271:16294–16299, Altmann et al. (1996) *Trends in Glycoscience and Glycotechnology* 8:101–114). These differences in carbohydrate structure can have dramatic effects on the in vitro and in vivo properties of the resulting glycoprotein. For example, the in vitro activity of human thyrotropin (hTSH) expressed in insect cells was five times higher than the activity of the same glycoprotein produced from mammalian Chinese hamster ovary (CHO) cells (Grossman et al. (1997) *Endocrinology* 138:92–100). However, the in vivo activity of the insect cell-derived product was substantially lower due to its rapid clearance from injected rats. The drop in in vivo hTSH activity was linked to the absence of complex-type oligosaccharides terminating in sialic acid in the insect cell product (Grossman et al. (1997) *EndocrinologyI* 138:92–100).

N-glycosylation is highly significant to glycoprotein structure and function. In insect and mammalian cells N-glycosylation begins in the endoplasmic reticulum (ER) with the addition of the oligosaccharide, $Glc_3Man_9GlcNAc_2$ onto the asparagine (Asn) residue in the consensus sequence Asn-X-Ser/Thr (Moremen, et al. (1994) *Glycobiology* 4:113–125, Varki et al. (1993) *Glycobiology* 3(2):97–130, Altmann et al. (1996) *Trends in Glycoscience and Glycotechnology* 8:101–114). As the glycoprotein passes through the ER and Golgi apparatus, enzymes trim and add different sugars to this N-linked glycan. These carbohydrate modification steps can differ in mammalian and insect hosts.

In mammalian cell lines, the initial trimming steps are followed by the enzyme-catalyzed addition of sugars including N-acetylglucosamine (GlcNAc), galactose (Gal), and sialic acid (SA) by the steps shown in FIG. 2, and as described in Goochee et al. (1991) *Bio/technology* 9:1347–1355.

In insect cells, N-linked glycans attached to heterologous and homologous glycoproteins comprise either high-mannose (Man$_{9-5}$GlcNAc$_2$) or truncated (paucimannosidic) (Man$_{3-2}$GlcNAc$_2$) oligosaccharides; occasionally comprising alpha(1,6)-fucose (FIG. 3; Jarvis et al. (1989) *Mol. Cell. Biol.* 9:214–223, Kuroda et al. (1990) *Virology* 174:418–329, Marz et al. (1995) *Glycoproteins* 543–563, Altmann et al. (1996) *Trends in Glycoscience and Glycotechnology* 8:101–114). These reports primarily directed to Sf-9 or Sf-21 cells from *Spodoptera frugiperda,* indicated that insect cells could trim N-linked oligosaccharides but could not elongate these trimmed structures to produce complex carbohydrates. Reports from other insect cell lines, including *Tricoplusia ni* (*T. ni;* High Five™) and *Estigmena acrea* (Ea-4), indicated the presence of limited levels of partially elongated hybrid (structures with one terminal Man branch and one branch with terminal Gal, GlcNAc, or another sugar; FIG. 4*a*) and complex (structures with two non-Man termini; FIG. 4*b*) N-linked oligosaccharides (Oganah et al. (1996) *Bio/Technology* 14:197–202, Hsu et al. (1997) *J. Biol. Chem.* 272:9062–9070). Low levels of GlcNAc transferase I and II (GlcNAc TI and TII), fucosyltransferase, mannosidases I and II, and Gal transferase (Gal T) have been reported in these insect cells; indicating a limited capability for production of these hybrid and complex N-linked oligosaccharides in these cells (Velardo et al. (1993) *J. Biol. Chem.* 268:17902–17907, Altmann et al. (1996) *Trends in Glycoscience and Glycotechnology* 8:101–114, van Die et al. (1996) *Glycobiology* 6:157–164).

However; most insect cell derived glycoproteins lack complex N-glycans. This absence may be attributed to the presence of the hexosaminidase N-acetylglucosaminidase that cleaves GlcNAc attached to the alpha(1,3) Man branch to generate paucimannosidic oligosaccharides (Licari et al (1993) *Biotech. Prog.* 9:146–152, Altmann et al. (1995) *J. Biol. Chem.* 270:17344–17349). Chemicals have been added in an attempt to inhibit this glycosidase activity, but significant levels of paucimannosidic structures remain even in the presence of these inhibitors (Wagner et al. (1996) *J. Virology* 70:4103–4109).

Manipulating carbohydrate processing in insect cells has been attempted; and in mammalian cells, the expression of sialyltransferases, galactosyltransferases and other enzymes is well established in order to enhance the level of oligosaccharide attachment (see U.S. Pat. No. 5,047,335). However, in these cases, the presence of the necessary donor nucleotide substrates, most significantly the sialylation nucleotide, CMP-sialic acid, in the proper subcellular compartment has been assumed. Attempts to manipulate carbohydrate processing have been made by expressing single transferases such as N-Acetylglucosamine transferase I (GlcNAc T1), galactose transferase (GAL T), or sialyltransferase (Lee et al. (1989) *J. Biol. Chem.* 264:13848–13855, Wagner et al. (1996) *Glycobiology* 6:165–175, Jarvis et al. (1996) *Nature Biotech.* 14:1288–1292, Hollister et al. (1998) *Glycobiology* 8:473–480, Smith et al. (1990) *J. Biol. Chem.* 265:6225–6234, Grabenhorst et al. (1995) *Eur. J. Biochem.* 232:718–725). Introduction of a mammalian beta(1, 4)-GalT using viral vectors (Jarvis et al. (1995) *Virology* 212:500–511) or stably-transformed cell lines (Hollister et al. (1998) *Glycobiology* 8:473–480) indicates that both approaches can enhance the extent of complex glycosylation of foreign glycoproteins expressed in insect cells. GlcNAcT1 co-expression can increase the number of recombinant glycoproteins with oligosaccharides containing GlcNAc on the Man alpha(1,3) branch (Jarvis et al. (1996) *Nature Biotech.* 14:1288–1292, Jarvis et al. (1995) *Virology* 212:500–511, Hollister et al. (1998) *Glycobiology* 8:473–480; Wagner et al. (1996) *Glycobiology* 6:165–175).

However, the production of complex carbohydrates comprising sialic acid has not been observed in these studies. Sialylation of a single recombinant protein (plasminogen) produced in baculovirus-infected insect cells has been reported (Davidson et al. (1990) *Biochemistry* 29:5584–5590), but findings appear to be specific to this glycoprotein. Conversely, many reports indicate the complete absence of any attached sialic acid on glycoproteins from all insect cell lines tested to date (Voss et al. (1993) *Eur. J. Biochem.* 217:913–919, Jarvis et al. (1995) *Virology* 212:500–511, Marz et al. (1995) *Glycoproteins* 543–563, Altmann et al. (1996) *Trends in Glycoscience and Glycotechnology* 8:101–114, Hsu et al. (1997) *J. Biol. Chem.* 272:9062–9070).

The reason for this absence of sialylated glycoproteins was initially puzzling since polysialic acid structures were obtained in *Drosophila* embryos (Roth et al. (1992) *Science* 256:673–675). However, as demonstrated herein, it is now evident that insect cell lines generate very little sialic acid as compared to mammalian CHO cells (See FIG. 16). With very little sialic acid, the insect cells cannot generate the donor nucleotide CMP-sialic acid essential for sialylation. A similar lack or limitation in donor nucleotide substrates may be observed in other eukaryotes as well. Thus, the co-expression of sialyltransferase and other transferases must be accompanied by the intracellular generation of the proper donor nucleotide substrates and the proper acceptor substrates in order for the production of sialylated and other complex glycoproteins in eukaryotes. In addition, sialic acid and CMP-sialic acid are not permeable to cells so these substrates can not be provided directly to the medium of the cultures (Bennett et al. (1981) *J. Cell. Biol.* 88:1–15).

The manipulation of post-translational processing is particularly relevant to biotechnology since recombinant DNA products generated in different hosts are usually identical at the amino acid level and differ only in the attached carbohydrate composition (Goochee et al. (1991) *Bio/technology* 9:1347–1355). Engineering carbohydrate pathways is useful to make recombinant DNA technology more versatile and expand the number of hosts that can generate particular glycoforms. This flexibility could ultimately lower biotechnology production costs since host efficiency would be the primary factor dictating which expression system is chosen rather than a host's capacity to produce a specific glycoform. Furthermore, carbohydrate engineering is useful to tailor a glycoprotein to include specific oligosaccharides that could alter biological activity, structural properties or circulatory targets. Such carbohydrate engineering efforts will provide a greater variety of recombinant glyco-products to the biotechnology industry.

Glycoproteins containing sialylated oligosaccharides would have improved in vivo circulatory half-lives that could lead to their increased utilization as vaccines and therapeutics. In particular, complex sialylated glycoproteins from insect cells would be more appropriate biological mimics of native mammalian glycoproteins in molecular recognition events in which sialic acid plays a role.

Therefore, manipulating carbohydrate processing pathways in insect and other eukaryotic cells so that the cells produce complex sialylated glycoproteins is useful for enhancing the value of heterologous expression systems and increasing the application of heterologous cell expression products as vaccines, therapeutics, and diagnostic tools; for increasing the variety of glycosylated products to be generated in heterologous hosts; and for lowering biotechnology production costs, since particular expression systems can be selected based on efficiency of production rather than the capacity to produce particular product glycoforms.

SUMMARY OF THE INVENTION

Compositions and methods for producing glycoproteins having sialylated oligosaccharides are provided. The compositions of the invention comprise enzymes involved in carbohydrate processing and production of nucleotide sugars, nucleotide sequences encoding such enzymes, and cells transformed with these nucleotide sequences. The compositions of the invention are useful in methods for producing complex sialylated glycoproteins in cells of interest including, but not limited to, mammalian cells and non-mammalian cells (e.g., insect cells).

The sialylation process involves the post-translational addition of a donor substrate, cytidine monophosphate-sialic acid (CMP-SA) onto a specific acceptor carbohydrate (GalGlcNAcMan-R) via an enzymatic reaction catalyzed by a sialyltransferase in the Golgi apparatus. Since one or more of these three reaction components (i.e., acceptor, donor substrate, and the enzyme sialyltransferase) is limiting or absent in certain cells of interest, methods are provided to enhance the production of the limiting components. Polynucleotide sequences encoding the enzymes used according to the methods of the invention are known or novel bacterial invertebrate, fungal, or mammalian sequences and/or fragments or variants thereof, that are optionally identified using bioinformatics searches. According to one embodiment of the invention, completion of the sialylation reaction is achieved by expressing a sialyltransferase enzyme, or a fragment or variant thereof, in the presence of acceptor and/or donor substrates. The invention also provides an assay for sialylation, wherein the structures and compositions of N-linked oligosaccharides attached to a model secreted glycoprotein, (e.g., transferrin), is elucidated using multidimensional chromatography.

Cells of interest that have been recombinantly engineered to produce new forms of sialylated glycoproteins, higher concentrations of sialylated glycoproteins, and/or elevated concentrations of donor substrates (.g., nucleotides sugars) required for sialylation, as well as kits for expression of sialylated glycoproteins are also provided.

BRIEF DESCRIPTION OF THE DRAWINGS

FIG. 3 depicts a Paucimannosidic oligosaccharide.

FIG. 4a depicts a hybrid glycan from *Estigmena acrea* (Ea-4) insect cells.

FIG. 4b depicts a complex glycan from *Estigmena acrea* (Ea-4) insect cells.

FIG. 12 depicts the reaction products resulting from incubation of UDP-Gal-6-Naph and Dans-AE-GlcNAc in the presence of Galactose-transferase, as described in the "Experimental" section below.

FIG. 17 depicts how selective inhibition of N-acetylglucosaminidase allows for production of complex oligosaccharide structures.

FIG. 19 depicts two potential specific chemical inhibitors of N-acetylglucosaminidase.

FIG. 27 depicts the nucleotide sequence of human aldolase (SEQ ID NO:1).

FIG. 28 depicts the amino acid sequence of human aldolase (SEQ ID NO: 2) encoded by the sequence shown in FIG. 27 (SEQ ID NO: 1).

FIG. 29 depicts the nucleotide sequence of human CMP-SA synthetase (cytidine monophosphate-sialic acid synthetase) (SEQ ID NO: 3).

FIG. 30 depicts the amino acid sequence of human CMP-SA synthetase (SEQ ID NO: 4) encoded by the sequence shown in FIG. 29 (SEQ ID NO: 3).

FIG. 31 depicts the nucleotide sequence of human sialic acid synthetase (human SA-synthetase; human SAS) (SEQ ID NO: 5).

FIG. 32 depicts the amino acid sequence of human SA-synthetase (SAS) (SEQ ID NO: 6) encoded by the sequence shown in FIG. 31 (SEQ ID NO: 5).

FIG. 33 depicts the types and quantities of oligosaccharide structures found on recombinant human transferrin in the presence and absence of Gal T overexpression.

FIGS. 35 A–C depicts an alignment of the polypeptide (SEQ ID NO: 6) encoded by the human SAS polynucleotide open-reading frame (SEQ ID NO:5).

FIG. 35 D depicts the amino acid sequence homology between human SAS (top sequence) (SEQ ID NO: 6) and bacterial sialic acid synthetase (NeuB) (bottom sequence) (SEQ ID NO: 8).

FIG. 36 (B) depicts an RNA (Northern) blot of human tissues (spleen, thymus, prostate, testis, ovary, small intestine, peripheral blood lymphocytes (PBL), colon, heart, brain, placenta, lung, liver, skeletal muscle, kidney, and pancreas) probed for sialic acid synthetase RNA transcripts. Transcript sizes (in kilobases) are indicated by comparison to the scale on the left side.

FIG. 37 (A) depicts the sialic acid content of lysed cell lines after filtration through a 10,000 MWCO membrane. The cell lines analyzed were Sf-9 (insect) cells in standard media, SF-9 cells supplemented with 10% FBS (fetal bovine serum), or CHO (Chinese Hamster Ovary) cells. The original chromatogram values have been divided by protein concentration to normalize chromatograms. The standards shown are Neu5Ac at 1000 fmol, Neu5Gc at 200 fmol, and KDN at 50 fmol. FIG. 37 (B) depicts a chromatogram of the sialic acid content of lysates from various Sf-9 cells. "AcSAS Infected" cell lysates were from Sf-9 cells infected with baculovirus containing the human SAS cDNA. The Neu5Ac and KDN "Standards" are shown at 1,000 fmol concentrations. "A35 Infected" cell lysates are from Sf-9 infected by baculovirus not containing the SAS cDNA. "Uninfected" cell lysates are from normal Sf-9 cells not infected by any baculovirus. Original chromatogram values have been divided by protein concentration to normalize chromatograms. FIG. 37 (C) depicts a chromatogram of the sialic acid content from lysates of Sf-9 grown in media supplemented by 10 mM ManNAc; cells were infected or not infected with baculovirus as shown in FIG. 37 (B). Original chromatogram values have been divided by protein concentrations to normalize chromatograms. Neu5Ac and KDN standards represent 1,000 fmol.

FIG. 38 (A) depicts chromatogram results of a Neu5Ac-9-phosphate assay performed using lysates from Sf-9 cells infected with the AcSAS baculovirus (containing the human SAS cDNA). KDN and Neu5Ac standards are shown at 5000 fmol. FIG. 38 (B) depicts chromatogram results of a KDN-9-phosphate assay performed using lysates from Sf-9 cells infected with the AcSAS baculovirus (containing the human SAS cDNA). KDN and Neu5Ac standards are shown at 5000 fmol.

DETAILED DESCRIPTION OF THE INVENTION

Figure 1:
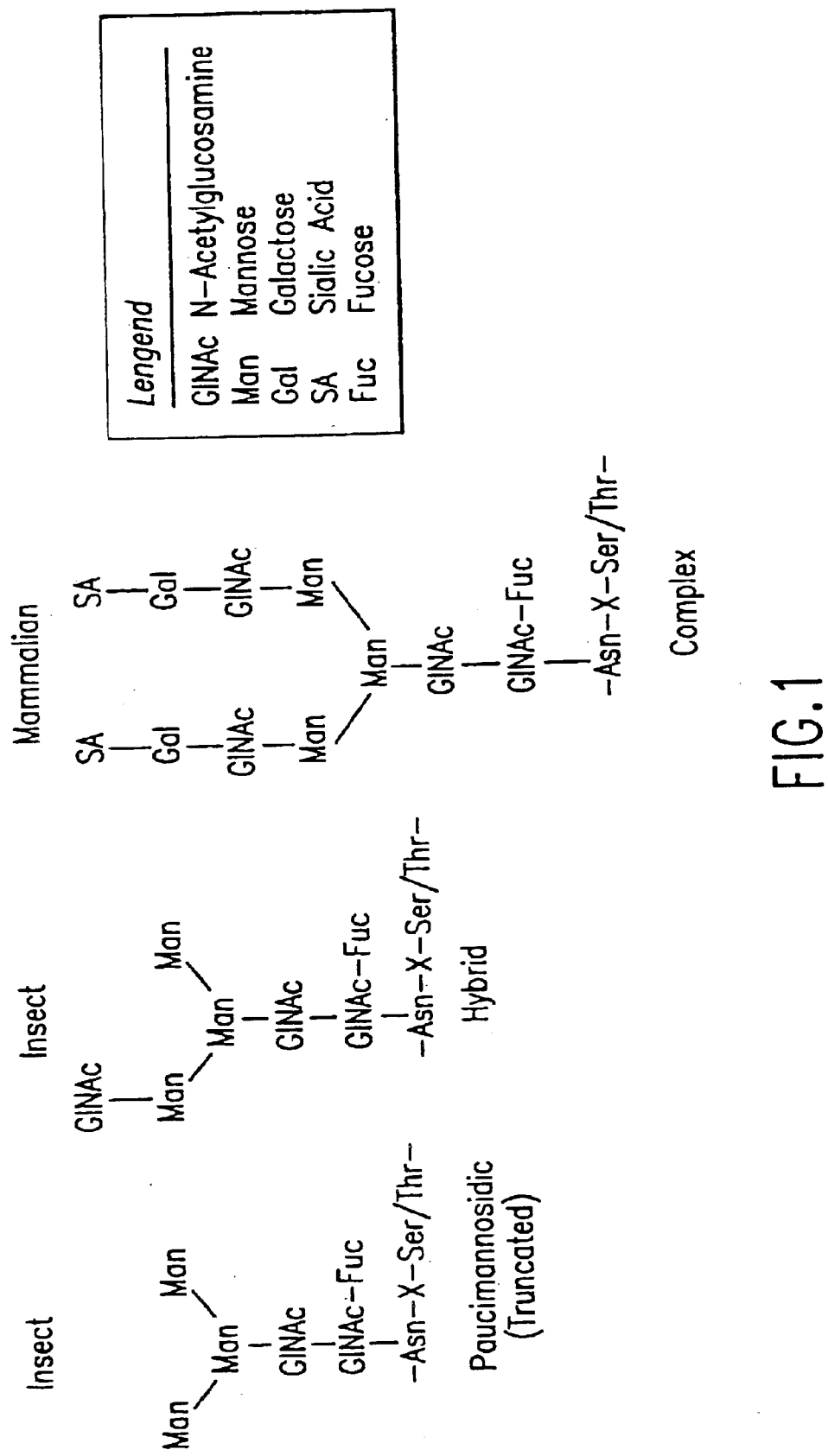
FIG. 1 depicts the typical differences in insect and mammalian carbohydrate structures.
Figure 2:
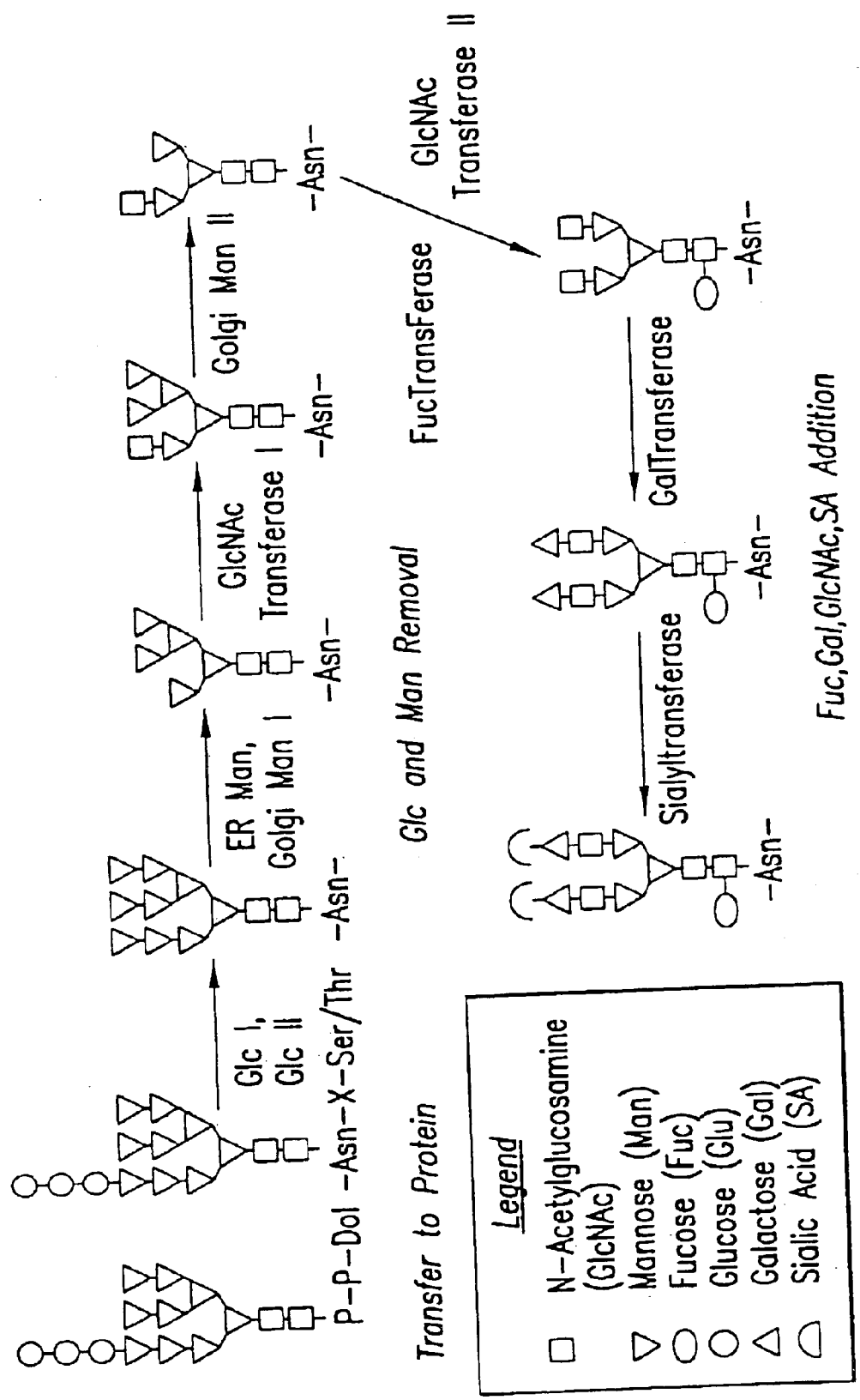
FIG. 2 depicts the enzymatic generation of a complex sialylated carbohydrate in mammalian cells.

Compositions and methods for producing glycoproteins with sialylated oligosaccharides are provided. In particular, the carbohydrate processing pathways of cell lines of interest are manipulated to produce complex sialylated glycoproteins. Such sialylated glycoproteins find use as pharmaceutical compositions, vaccines, diagnostics, therapeutics, and the like.

Cells of interest include, but are not limited to, mammalian cells and non-mammalian cells, such as, for example, CHO, plant, yeast, bacterial, insect, and the like. The methods of the invention can be practiced with any cells of interest. By way of example, methods for the manipulation of insect cells are described fully herein. However, it is recognized that the methods may be applied to other cells of interest to construct processing pathways in any cell of interest for generating sialylated glycoproteins.

Oligosaccharides on proteins are commonly attached to asparagine residues found within Asn-X-Ser/Thr consensus sequences; such asparagine-linked oligosaccharides are commonly referred to as "N-linked". The sialylation of N-linked glycans occurs in the Golgi apparatus by the following enzymatic mechanism: CMP-SA+ GalGlcNAcMan-R sialyltransferase SAGalGlcNAcMan-R+ CMP. The successful execution of this sialylation reaction depends on the presence of three elements: 1) the correct carbohydrate acceptor substrate (designated GalGlcNAcMan-R in the above reaction; where the acceptor substrate is a branched glycan, GalGlcNAcMan is comprised by at least one branch of the glycan, the Gal is a terminal Gal, and R is an N-linked glycan); 2) the proper donor nucleotide sugar, cytidine monophosphate-sialic acid (CMP-SA); and 3) a sialyltransferase enzyme. Each of these reaction components is limiting or missing in insect cells (Hooker et al. (1997) *Monitoring the glycosylation pathway of recombinant human interferon-gamma produced by animal cells,* Hsu et al. (1997) *J. Biol. Chem.* 272:9062–9070, Jarvis et al. (1995) *Virology* 212:500–511, Jenkins et al. (1998) *Cell Culture Engineering VI,* Oganah et al. (1996) *Bio/Technology* 14:197–202).

It will be apparent to those skilled in the art that where a cell of interest is manipulated according to the methods of the invention such that the cell produces a desired level of the donor substrate CMP-SA, and expresses a desired level of sialyltransferase; any oligosaccharide or monosaccharide, any compound containing an oligosaccharide or monosaccharide, any compatible aglycon (for example Galsphingosine), any asparagine (N)-linked glycan, any serine- or threonine-linked (O-linked) glycan, and any lipid containing a monosaccharide or oligosaccharide structure can be a proper acceptor substrate and can be sialylated within the cell of interest.

Accordingly, the methods of the invention may be applied to generate sialylated glycoproteins for which the acceptor substrate is not necessarily limited to the structure GalGlcNAcMan-R, although this structure is particularly recognized as an appropriate acceptor substrate structure for production of N-linked sialylated glycoproteins. Thus, according to the methods of the present invention, the acceptor substrate can be any glycan. Preferably, the acceptor substrate according to the methods of the invention is a branched glycan. Even more preferably, the acceptor substrate according to the methods of the invention is a branched glycan comprising a terminal Gal in at least one branch of the glycan. Yet even more preferably, the acceptor substrate according to the methoids of the invention has the structure GalGlcNAcMan in at least one branch of the glycan and the Gal is a terminal Gal.

It will also be apparent to those skilled in the art that engineering the sialylation process into cells of interest according to the methods of the present invention requires the successful manipulation and integration of multiple interacting metabolic pathways involved in carbohydrate processing. These pathways include participation of glycosyltransferases, glycosidases, the donor nucleotide sugar (CMP-SA) synthetases, and sialic acid transferases. "Carbohydrate processing enzymes" of the invention are enzymes involved in any of the glycosyltransfer, glycosidase, CMP-SA synthesis, and sialic acid transfer pathways. Known carbohydrate engineering efforts have generally focused on the expression of transferases (Lee et al. (1989) *J. Biol. Chem.* 264:13848–13855, Wagner et al. (1996) *J. Virology* 70:4103–4109, Jarvis et al. (1996) *Nature Biotech.* 14:1288–1292, Hollister et al. (1998) *Glycobiology* 8:473–480, Smith et al. (1990) *J. Biol. Chem.* 265:6225–6234, Grabenhorst et al. (1995) *Eur. J. Biochem.* 232:718–725; U.S. Pat. No. 5,047,335; International patent application publication number WO 98/06835). However, it is recognized in this invention that the mere insertion of one or more transferases into cells of interest does not ensure sialylation, as there are generally insufficient levels of the donor (CMP-SA) and the acceptor substrates, particularly GalGlcNAcMan-R.

The methods of the present invention permit manipulation of glycoprotein production in cells of interest by enhancing the production of donor nucleotide sugar substrate (CMP-SA) and optionally, by introducing and expressing sialyltransferase and/or acceptor substrates. By "cells of interest" is intended any cells in which the endogenous CMP-SA levels are not sufficient for the production of a desired level of sialylated glycoprotein in that cell. The cell of interest can be any eukaryotic or prokaryotic cell. Cells of interest include, for example, insect cells, fungal cells, yeast cells, bacterial cells, plant cells, mammalian cells, and the like. Human cells and cell lines are also included in the cells of interest and may be utilized according to the methods of the present invention to, for example, manipulate sialylated glycoproteins in human cells and/or cell lines, such as, for example, kidney, liver, and the like. By "desired level" is intended that the quantity of a biochemical comprised by the cell of interest is altered subsequent to subjecting the cell to the methods of the invention. In this manner, the invention comprises manipulating levels of CMP-SA and/or sialylated glycoprotein in the cell of interest. In a preferred embodiment of the invention, manipulating levels of CMP-SA and sialylated glycoprotein comprise increasing the levels to above endogenous levels. It is recognized that the increase can be from a non-detectable level to any detectable level; or the increase can be from a detected endogenous level to a higher level.

According to the present invention, production of the acceptor substrate is achieved by optionally screening a variety of cell lines for desirable processing enzymes, suppressing unfavorable cleavage reactions that generate truncated carbohydrates, and/or by enhancing expression of desired glycosyltransferase enzymes such as galactose transferase. Methods of enhancing expression of certain carbohydrate processing enzymes, including but not limited to, glycosyltransferases, are described in U.S. Pat. No. 5,047,335 and International patent application publication number WO 98/06835, the contents of which are herein incorporated by reference.

According to the present invention, production of the donor substrate, CMP-SA, may be achieved by adding key precursors such as N-acetylmannosamine (ManNAc), N-acetylglucosamine (GlcNAc) and glucosamine to cell growth media, by enhancing expression of limiting enzymes in CMP-SA production pathway in the cells, or any combination thereof.

For purposes of the present invention, by "enhancing expression" is intended to mean that the translated product of a nucleic acid encoding a desired protein is higher than the endogenous level of that protein in the host cell in which the nucleic acid is expressed. In a preferred embodiment of the invention, the biological activity of a desired carbohydrate processing enzyme is increased by enhancing expression of the enzyme.

For the purposes of the invention, by "suppressing activity" is intended to mean decreasing the biological activity of an enzyme. In this aspect, the invention encompasses reducing the endogenous expression of the enzyme protein, for example, by using antisense and/or ribozyme nucleic acid sequences corresponding to the amino acid sequences of the enzyme; gene knock-out mutagenesis; and/or by inhibiting the activity of the enzyme protein, for example, by using chemical inhibitors.

By "endogenous" is intended to mean the type and/or quantity of a biological function or a biochemical composition that is present in a naturally occurring or recombinant cell prior to manipulation of that cell according to the methods of the invention.

By "heterologous" is intended to mean the type and/or quantity of a biological function or a biochemical composition that is not present in a naturally occurring or recombinant cell prior to manipulation of that cell by the methods of the invention.

For purposes the present invention, by "a heterologous polypeptide or protein" is meant as a polypeptide or protein expressed (i.e. synthesized) in a cell species of interest that is different from the cell species in which the polypeptide or protein is normally expressed (i.e. expressed in nature).

Methods for determining endogenous and heterologous functions and compositions relevant to the invention are provided herein; and otherwise encompass those methods known in the art.

Generation of Acceptor Carbohydrate Substrate: GalGlcNAcMan-R

According to the methods of the present invention, production of the acceptor substrate glycan GalGlcNAcMan-R, is particularly desirable for the sialylation reaction of N-linked glycoproteins, moreover the terminal Gal is required. Thus, in one embodiment of the invention the cells of interest are manipulated (using techniques described herein or otherwise known in the art) to contain this substrate. For example, for insect cells which principally produce truncated carbohydrates terminating in Man or GlcNAc, such cells may routinely be manipulated to produce a significant fraction of complex oligosaccharides terminating in Gal. Three non limiting, non-exclusive approaches that may be routinely applied to produce a significant fraction of complex oligosaccharides terminating in Gal include: (1) developing screening assays to analyze a selection of insect cell lines for the presence of particular carbohydrate processing enzymes; (2) elevating production of Gal-terminated oligosaccharides by expressing specific enzymes relevant to carbohydrate processing pathways; and (3) suppressing carbohydrate processing pathways that produce truncated N-linked glycans which cannot serve as acceptors in downstream glycosyltransferase reactions.

Thus, in one embodiment, to produce GalGlcNAcMan-R acceptor substrates according to the methods of the invention, cell lines of interest are initially, and optionally, screened to identify cell lines with the desired endogenous carbohydrate production for subsequent metabolic manipulations. More particularly, the screening process includes characterizing cell lines for glycosyl transferase activity using techniques described herein or otherwise known in the art. Furthermore, it is recognized that any screened cell line could generate some paucimannosidic carbohydrates. Accordingly, the screening process also includes using techniques described herein or otherwise known in the art to characterize cell lines for particular glycosidase activity leading to production of paucimannosidic structures.

Thus, in another embodiment, for the production of the acceptor substrates, the invention encompasses utilizing methods described herein or otherwise known in the art to enhance the expression of one or more transferases. Such methods include, but are not limited to, methods that enhance expression of Gal T, GlcNAc-TI and -TII or any combination thereof; for example, as described in International patent application publication number WO 98/06835 and U.S. Pat. No. 5,047,335.

Thus, in another embodiment, concentrations of acceptor substrates are increased by using methods described herein or otherwise known in the art to suppress the activity of one or more endogenous glycosidases. By way of example, an endogenous glycosidase, the activity of which may be suppressed accoreding to the methods of the invention includes, but is not limited to, the hexosaminidase, N-acetylglucosaminidase (an enzyme that degrades the substrate required for oligosaccharide elongation).

Thus, the invention encompasses enhancing metabolic pathways that produce the desired acceptor carbohydrates and/or suppressing those pathways that produce truncated acceptors.

Characterizing Cell Lines Using Enzyme Screening Assay

The cell lines of interest produce different N-glycan structures. Thus, such cells can routinely be screened using techniques described herein or otherwise known in the art to determine the presence of carbohydrate processing enzymes of interest. In insect cells, for example, different insect cell lines produce very different N-glycan structures (Jarvis et al. (1995) *Virology* 212:500–511, Hsu et al. (1997) *J. Biol. Chem.* 272:9062–9070, Nishimura et al. (1996) *Bioorg. Med. Chem.* 4:91–96). However, only a few cell lines have been characterized, in part due to the lack of efficient screening assays. The present invention provides methods implementing fluorescence energy transfer and Europium fluorescence assays to screen a selection of different cells of interest, such as, for example, insect cell lines for the presence of critical carbohydrate processing enzymes.

Analytical bioassays described herein or otherwise known in the art are also provided according to the methods of the present invention to detect the presence of favorable carbohydrate processing enzymes, including, but not limited to, galactosyl transferase (Gal T), GlcNAc transferase I (GlcNAc T I), and sialyltransferase; and to detect undesirable enzymes including, but not limited to, N-acetylglucosaminidase.

Where the cells of interest are insect cells, it will be immediately apparent that substantial diversity exists among established insect cell lines due to the range of species and tissues from which these lines were derived. Many of these lines can routinely be infected by the baculovirus, *Autographa californica* nuclear polyhedrosis virus (AcMNPV), and used for the production of heterologous proteins. However, only a few cell lines are routinely used for recombinant protein production using techniques described herein or otherwise known in the art. These cell lines will be immediately apparent by one skilled in the art. It is recognized that any cell line can be screened for specific carbohydrate processing enzymes, and manipulated for the purposes of the present invention. Examples of such cell lines include, but are not limited to, insect cell lines, including but not limited to, *Spodoptera frugiperda* (e.g. Sf-9 or Sf-21 cells), *Trichoplusia ni* (*T. ni*), and *Estigmene acrea* (Ea4). *Spodoptera frugiperda* lines (Sf-9 or Sf-21) are the most widely used cell lines and a significant amount information is known about the oligosaccharide processing in these cells. *Trichoplusia ni* (e.g. High Five™ cells; Invitrogen Corp., Carlsbad, Calif., USA) cells have been shown to secrete high yields of heterologous proteins with attached hybrid and complex N-glycans (Davis et al. (1993) *In Vitro Cell. Dev. Biol.* 29:842–846). *Estigmena acrea* (Ea-4) have been used to generate hybrid and complex N-linked oligosaccharides terminating in GlcNAc and Gal residues (Oganah et al. (1996) *Bio/Technology* 14:197–202).

Drosophila Schneider S2 cell lines represent another insect cell line used for the production of heterologous proteins. Though these cells cannot be infected by the AcNPV expression vector, they are used for production of heterologous proteins via an alternative technology known in the art. These cell lines represent other insect cell line candidates whose glycosylation processing characteristics may be modified to include sialylation.

In insect cells, paucimannosidic structures are produced by a membrane-bound N-acetylglucosaminidase, which removes terminal GlcNAc residues from the alpha(1,3) arm of the trimannosyl core (Altmann et al. (1995) *J. Biol. Chem.* 270:17344–17349). This trimannosyl core structure lacks the proper termini required for conversion of side chains to sialylated complex structures; therefore, suppression of the N-acetylglucosaminidase activity can reduce or eliminate the formation of these undesired oligosaccharide structures, as illustrated in FIG. 17.

To reduce the N-acetylglucosaminidase activity in the target insect cell line(s), the invention provides vectors encoding N-acetylglucosaminidase or other glucosaminidase cDNAs in the antisense orientation and/or, vectors encoding ribozymes and/or, vectors containing sequences capable of "knocking out" the N-acetylglucosaminidase other glucosaminidase genes via homologous recombination. Expression plasmids described herein or otherwise known in the art are constructed using techniques known in the art to produce stably-transformed insect cells that constitutively express the antisense construct and/or ribozyme construct to suppress translation of N-acetylglucosaminidase other glucosaminidases or alternatively, to use homologous recombination techniques known in the art are to "knock-out" the N-acetylglucosaminidase other glucosaminidase genes. Particular sequences to be used in the antisense and/or ribozyme construction are described herein, for example, in Example 4. Techniques described herein or otherwise known in the art may be routinely applied to analyze N-linked oligosaccharide structures and to determine if N-glycan processing is altered and of the number of paucimannosidic structures in these cells is reduced.

Antisense technology can be used to control gene expression through antisense DNA or RNA or through triple-helix formation. Antisense techniques are discussed, for example, in Okano, J. Neurochem. 56: 560 (1991); Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, J., Neurochem. 56:560 (1991); Oligodeoxynucleotides as Antisense Inhibitors of Gene Expression, CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). The methods are based on binding of a polynucleotide to a complementary DNA or RNA. For example, the 5' coding portion of a polynucleotide that encodes the amino terminal portion of N-acetylglucosaminidase and/or other glucosaminidases may be used to design antisense RNA oligonucleotides of from about 10 to 40 base pairs in length. A DNA oligonucleotide is designed to be complementary to a region of the gene involved in transcription thereby preventing transcription and the production of N-acetylglucosaminidase and/or other glucosaminidases. The antisense RNA oligonucleotide hybridizes to the mRNA in vivo and blocks translation of the mRNA molecule into N-acetylglucosaminidase and/or other glucosaminidase polypeptides. The oligonucleotides described above can also be delivered to cells such that the antisense RNA or DNA may be expressed in vivo to inhibit production of N-acetylglucosaminidase and/or other glucosaminidases.

In one embodiment, the N-acetylglucosaminidase and/or other glucosaminidase antisense nucleic acids of the invention are produced intracellularly by transcription from an exogenous sequence. For example, a vector or a portion thereof, is transcribed, producing an antisense nucleic acid (RNA) of the invention. Such a vector would contain a sequence encoding a N-acetylglucosaminidase and/or other glucosaminidase antisense nucleic acids. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in insect, yeast, mammalian, and plant cells. Expression of the sequences encoding N-acetylglucosaminidase and/or other glucosaminidases, or fragments thereof, can be by any promoter known in the art to act in insect, yeast, mammalian, and plant cells. Such promoters can be inducible or constitutive. Such promoters include, but are not limited to, the baculovirus polyhedrin promoter (Luckow et al. (1993) *Curr. Opin. Biotech.* 4:564–572, Luckow et al. (1995)), the SV40 early promoter region (Bernoist and Chambon, Nature 29:304–310 (1981), the promoter contained in the 3' long terminal repeat of Rous sarcoma virus (Yamamoto et al., Cell 22:787–797 (1980), the herpes thymidine promoter (Wagner et al., Proc. Natl. Acad. Sci. U.S.A. 78:1441–1445 (1981), the regulatory sequences of the metallothionein gene (Brinster, et al., Nature 296:39–42 (1982)), etc.

The antisense nucleic acids of the invention comprise sequences complementary to at least a portion of an RNA transcript of N-acetylglucosaminidase and/or other glucosaminidase genes. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded N-acetylglucosaminidase and/or other glucosaminidase antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a N-acetylglucosaminidase and/or other glucosaminidase RNAs it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333–335. Thus, oligonucleotides complementary to either the 5'- or 3'-non-translated, non-coding regions of N-acetylglucosaminidase and/or other glucosaminidases, could be used in an antisense approach to inhibit translation of endogenous N-acetylglucosaminidase and/or other glucosaminidase mRNAs. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of N-acetylglucosaminidase and/or other glucosaminidase mRNAs, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), agents facilitating transport across the cell membrane (see, e.g., Letsinger et al., 1989, Proc. Natl. Acad. Sci. U.S.A. 86:6553–6556; Lemaitre et al., Proc. Natl. Acad. Sci. 84:648–652 (1987); PCT Publication No. WO88/09810, published Dec. 15, 1988), or hybridization-triggered cleavage agents (See, e.g., Krol et al., BioTechniques 6:958–976 (1988)) or intercalating agents. (See, e.g., Zon, Pharm. Res. 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an alpha-anomeric oligonucleotide. An alpha -anomeric oligonucleotide forms specific double-stranded hybrids with complementary RNA in which, contrary to the usual beta-units, the strands run parallel to each other (Gautier et al., Nucl. Acids Res. 15:6625–6641 (1987)). The oligonucleotide is a 2-0-methylribonucleotide (Inoue et al., Nucl. Acids Res. 15:6131–6148 (1987)), or a chimeric RNA-DNA analogue (Inoue et al., FEBS Lett. 215:327–330 (1997)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448–7451 (1988)), etc.

While antisense nucleotides complementary to the N-acetylglucosaminidase and/or other glucosaminidase coding region sequences could be used, those complementary to the transcribed untranslated region are most preferred.

Potential N-acetylglucosaminidase or other glucosaminidase activity suppressors according to the invention also include catalytic RNA, or a ribozyme (See, e.g., PCT International Publication WO 90/11364, published Oct. 4, 1990; Sarver et al, Science 247:1222–1225 (1990). While ribozymes that cleave mRNA at site specific recognition sequences can be used to destroy N-acetylglucosaminidase and/or other glucosaminidase mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature 334:585–591 (1988). Preferably, the ribozyme is engineered so that the cleavage recognition site is located near the 5' end of the N-acetylglucosaminidase and/or other glucosaminidase mRNAs; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express N-acetylglucosaminidase and/or other glucosaminidases in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous N-acetylglucosaminidase and/or other glucosaminidase messages and inhibit translation. Since ribozymes unlike antisense molecules, are catalytic, a lower intracellular concentration is required for efficiency.

Endogenous gene expression can also be reduced by inactivating or "knocking out" the N-acetylglucosaminidase and/or other glucosaminidase gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention, or a completely unrelated DNA sequence (such as for example, a sialic acid synthetase) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). The contents of each of the documents recited in this paragraph is herein incorporated by reference in its entirety.

The use of chemical inhibitors is also within the scope of the present invention, in addition to, or as an alternative to, the antisense approach, and/or the ribozyme approach, and/ or the gene "knock-out" approach, as means for suppressing glucosaminidase activity in insect cell cultures. Chemical inhibitors that may be used to suppress glucosaminidase activity include, but are not limited to, 2-acetamido- 1,2,5-trideoxy-1,5 amino-D-glucitol can limit the N-acetylglucosaminidase activity in insect cells (Legler et al. (1991) Biochim. Biophys. Acta 1080:80–95, Wagner et al. (1996) J. Virology 70:4103–4109). In addition, a number of other N-acetylglucosaminidase inhibitors may also be used according to the present invention, including, but not limited to, nagastatin (with a $K_I$ value in the $10^{-8}$ range) and GlcNAc-oxime ($K_I$ in 0.45–22 mM) which are commercially, publicly, or otherwise available for the purposes of the present invention (Nishimura et al. (1996) Bioorg. Med. Chem. 4:91–96, Aoyagi et al. (1992) J. Antibiotics 45:1404–1408).

The chemical inhibitors mentioned above do not distinguish between lysosomal N-acetylglucosaminidase and the target membrane-bound N-acetylglucosaminidase activity in the secretory compartment. Thus, a more specific inhibitor, based on the substrate structure, is provided to serve not merely as a competitive inhibitor, but also as an affinity labeling reagent. The chemical structure for two possible chemical compounds with specificity for inhibiting membrane-bound glucosaminidase one or both of which may be used according to the present invention, are shown in FIG. 19. Subsequent to expression and purification of the N-acetylglucosaminidase, the effectiveness of these inhibitors may be tested and compared in in vitro and/or in vivo trials using techniques described herein or otherwise known in the art. As above, these chemical inhibitors are then used in addition to, or as an alternative to, antisense suppression, ribozyme suppression, and/or gene knock-out mutagenesis, of glucosaminidase activity in insect cells.

Figure 20:
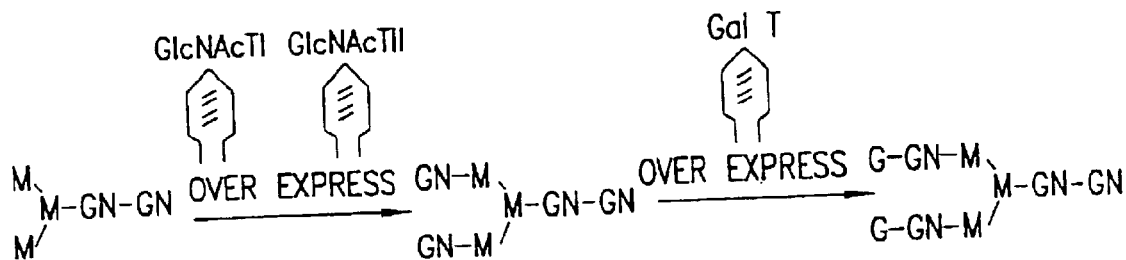
FIG. 20 schematically depicts that the overexpression of various glycosyltransferases leads to greater production of oligosaccharide acceptor substrates.

It is recognized that the suppression of glucosaminidase activity alone may not lead to production of the desired acceptor carbohydrate, if the enzymes responsible for generating structures terminating in Gal are lacking in particular cell lines. Thus, according to the methods of the present invention, Gal T activity in insect cells can be increased significantly by using techniques described described herein or otherwise known in the art to express a heterologous gene using a baculovirus construct containing nucleic acid sequences encoding Gal T or a fragment or variant thereof, or by stably transforming the cells with a gene coding for Gal T or a fragment or variant thereof. If N-glycan analysis indicates that lower than a desired level of the acceptor substrates are present even following glucosaminidase suppression, techniques described herein or otherwise known in the art may be applied to express glycosyltransferase enzymes as needed in insect cells to produce a larger fraction of the desired acceptor structures. FIG. 20 depicts that the overexpression of various glycosyltransferases leads to greater production of acceptor substrates.

Alternatively, the expression of glycosyltransferases will serve to limit generation of paucimannosidic structures by generating unacceptable glucosaminidase substrates terminating in Gal, or by competing against the glucosaminidase reaction (Wagner et al., Glycobiology 6:165–175 (1996)).

Figure 21:
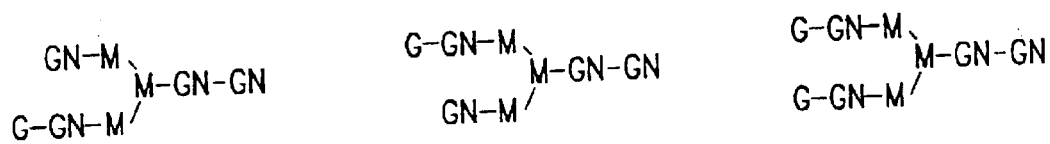
FIG. 21 depicts three possible N-glycan acceptor structures which include the terminal Gal (G) acceptor residue required for subsequent sialylation.

Thus, the invention comprises expression of glycosyltransferases combined with, or as an alternative to, suppression of N-acetylglucosaminidase activity in selected insect cell lines to produce desired quantities of carbohydrates containing the correct Gal (G) acceptor substrate for sialylation. FIG. 21 illustrates, without limitation, three examples of acceptor N-glycan structures that comprise the terminal Gal acceptor residue required for subsequent sialylation. Other desired carbohydrates structures with a branch terminating Gal are also possible and are encompassed by the invention.

Baculovirus expression vectors containing the coding sequence for GlcNAc-TI and -TII, and Gal T or fragments or variants thereof, and stable transfectants overexpressing GlcNAc-TI and GlcNAc-TII, and Gal T, or fragments or variants thereof are known, can be routinely generated using techniques known in the art, and are commercially, publicly, or otherwise available for the purposes of this invention. (See Jarvis et al. (1996) Nature Biotech. 14:1288–1292; Hollister et al. (1998) Glycobiology 8: 473–480; the contents of which are herein incorporated by reference). In addition, stable transfectants expressing GlcNAc-TI and GlcNAc-TII can be routinely generated using techniques known in the art, if overexpression proves desirable.

Production and Delivery of the Donor Substrate: CMP-Sialic Acid (CMP-SA)

For production of the donor substrate, CMP-SA, the invention provides methods and compositions comprising expression of limiting enzymes in the CMP-SA production pathway; in addition, or as an alternative to, the feeding of precursor substrates.

Figure 22:
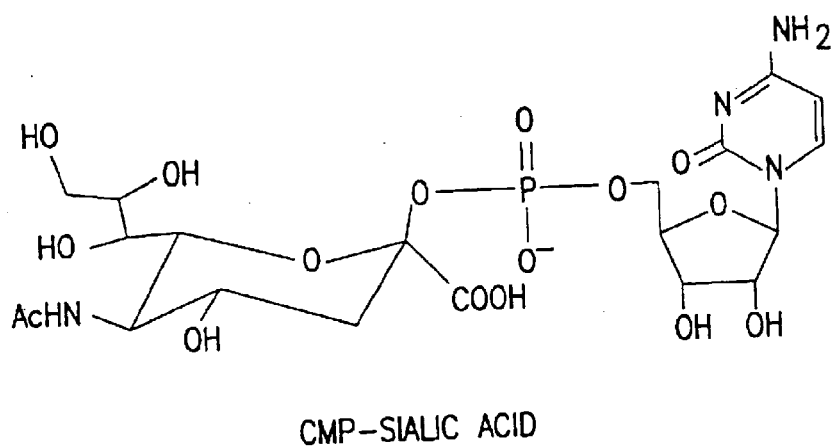
FIG. 22 depicts a structure of CMP-sialic acid (CMP-SA).

To produce sialylated N-linked glycoproteins, the donor substrate, CMP-sialic acid (CMP-SA), must be synthesized. The structure of CMP-SA is shown in FIG. 22. CMP-SA can be enzymatically synthesized from glucose or other simple sugars, glutamine, and nucleotides in mammalian cells and *E. coli* using the metabolic pathways shown in FIG. 5, and as described in Ferwerda et al. (1983) *Biochem. J.* 216:87–92; Mahmoudian et al. (1997) *Enzyme and Microbial Technology* 20:393–400; Schachter et al. (1973) *Metabolic Conjugation and Metabolic Hydrolysis* (New York Academic Press) 2–135.

Figure 16B:
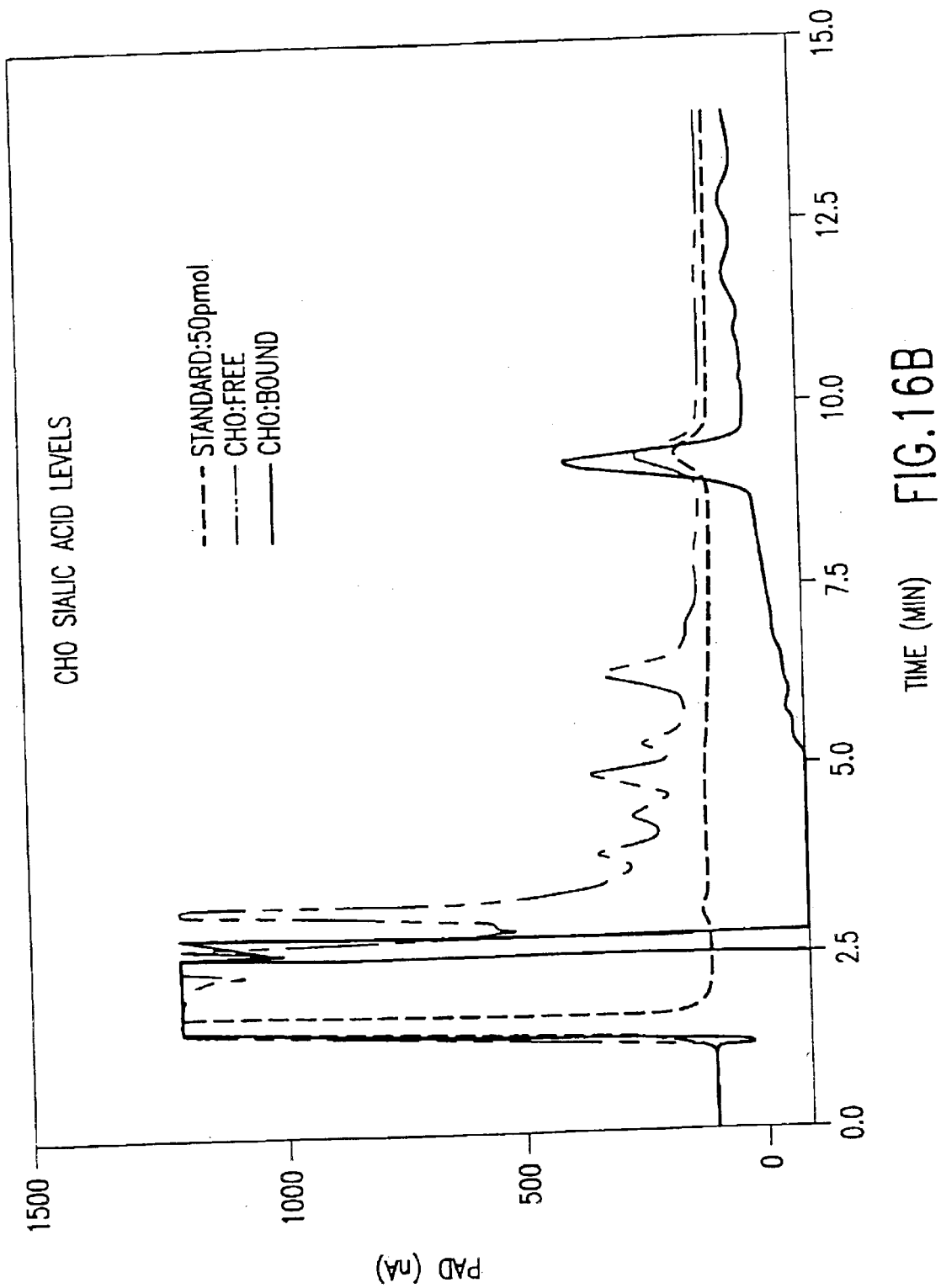
FIG. 16 depicts a chromatogram of sialic acid levels in SF9 insect cells and CHO (chinese hamster ovary) cells. In the panel labeled "Sf-9 Free Sialic Acid Levels" the known sialic acid standard elutes just prior to 10 minutes, while no corresponding sialic acid peak can be detected (above background levels) in Sf-9 cells. In the panel labeled "CHO sialic acid levels" the sialic acid standard elutes at approximately 9 minutes, while bound and free (released by acid hydrolysis) sialic acid peaks are observed at similar elution positions.

In some mammalian tissues and cell lines, the production and delivery of CMP-SA limits the sialylation capacity of these cells (Gu et al. (1997) *Improvement of the interferon-gamma sialylation in Chinese hamster ovary cell culture by feeding N-acetylmannosamine*). This problem is likely to be amplified in insect cells since negligible sialic acid levels are detected in *Trichoplusia ni* insect cells as compared to levels in Chinese Hamster Ovary (CHO) mammalian cells (FIG. 16). Furthermore, negligible CMP-SA was observed in Sf-9 and Ea-4 insect cells when compared to CHO cells (Hooker et al. (1997) *Monitoring the Glycosylation Pathway of Recombinant Human Interferon-Gamma Produced by Animal Cells,* European Workshop on Animal Cell Engineering, Costa Brava, Spain; and Jenkins (1998) *Restructuring the Carbohydrates of Recombinant Glycoproteins,* Cell Culture Engineering VI, San Diego, Calif.). These findings are relevant in light of the previously published observation that polysialic acid can be detected in Drosophila embryos (Roth et al. (1992) *Science* 256:673–675) and the observation of sialylated glycoproteins produced by other insect cells (Davidson et al. (1990) *Biochemistry* 29:5584–5590).

Figure 5:
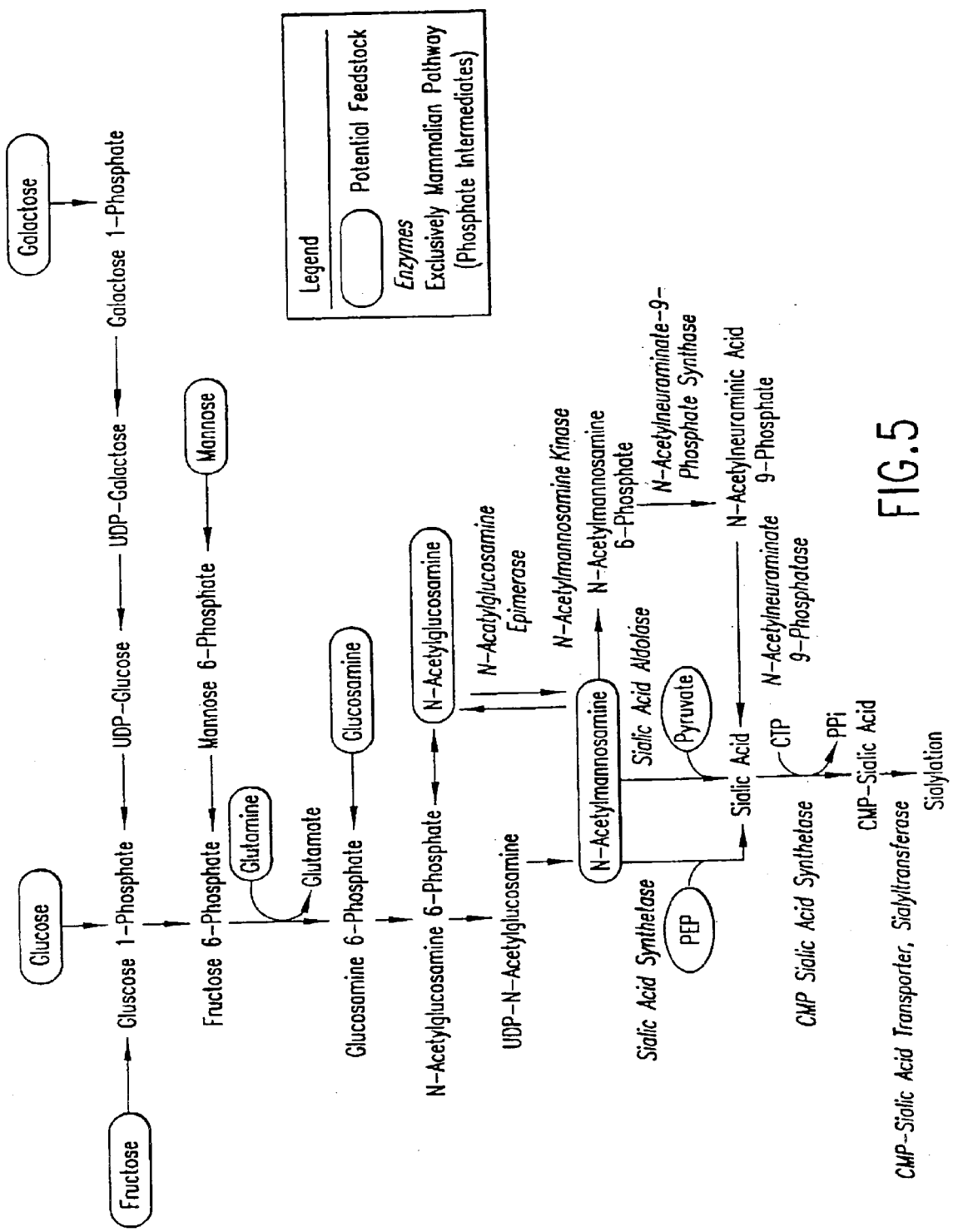
FIG. 5 depicts the nucleotide sugar production pathways in mammalian and *E. coli* cells leading to sialylation.

Production of sialic acid (SA), more specifically N-acetylneuraminic acid (NeuAc), from the precursor substrate ManNAc can proceed through three alternative pathways shown in FIG. 5. The principal pathway for the production of SA in *E. coli* and other bacteria utilizes the phosphoenylpyruvate (PEP) and ManNAc to produce sialic acids in the presence of sialic acid synthetase (Vann et al. (1997) *Glycobiology* 7:697–701). A second pathway, observed in bacteria and mammals, involves the reversible conversion by aldolase (also named N-acetylneuraminate lyase) of ManNAc and pyruvate to sialic acid (Schachter et al. (1973) *Metabolic Conjugation and metabolic Hydrolysis* (New York Academic Press) 2–135, Lilley et al. (1992) *Prot. Expr. and Pur.* 3:434–440). The aldolation reaction equilibrates toward ManNAc but can be manipulated to favor the production of sialic acid by the addition of excess ManNAc or pyruvate in vitro (Mahmoudian et al. (1997) *Enzyme and Microbial Technology* 20:393–400). The third pathway, observed only in mammalian tissue, begins with the ATP driven phosphorylation of ManNAc, and is followed by the enzymatic conversion of phosphorylated ManNAc to a phosphorylated form of sialic acid, from which the phosphate is removed in a subsequent step (van Rinsum et al. (1983) *Biochem. J.* 210:21–28, Schachter et al. (1973) *Metabolic Conjugation and metabolic Hydrolysis* (New York Academic Press) 2–135).

According to one embodiment of the invention, to overcome intracellular limitations of CMP-SA in mammalian cells, feeding of alternative precursor substrates may be applied to eliminate or reduce the need to produce CMP-SA from simple sugars (see Example 6). Since CMP-SA and its direct precursor, SA, are not permeable to cell membranes (Bennetts et al. (1981) *J. Cell. Biol.* 88:1–15), these substrates cannot be added to the culture medium for uptake by the cell. However, other precursors, including N-acetylmannosamine (ManNAc), glucosamine, and N-acetylglucosamine (GlcNAc) when added to the culture medium are absorbed into mammalian cells (see Example 6). See, for example, Gu et al. (1997) *Improvement of the interferon-gamma sialylation in Chinese hamster ovary cell culture by feeding N-acetylmannosamine,* Zanghi et al. (1997) *European Workshop on Animal Cell Engineering,* Ferwerda et al. (1983) *Biochem. J.* 216:87–92, Kohn et al. (1962) *J. Biol. Chem.* 237:304–308, Thomas et al. (1985) *Biochim. Biophys. Acta* 846:37–43, Bennetts et al. (1981) *J. Cell. Biol.* 88:1–15. The substrates are then enzymatically converted to CMP-SA and incorporated into homologous and heterologous glycoproteins (Gu et al. (1997) *Improvement of the interferon-gamma sialylation in Chinese hamster ovary cell culture by feeding N-acetylmannosamine,* Ferwerda et al. (1983) *Biochem. J.* 216:87–92, Kohn et al. (1962) *J. Biol. Chem.* 237:304–308, Bennetts et al. (1981) *J. Cell. Biol.* 88:1–15).

To be incorporated into oligosaccharides, sialic acid and cytidine triphosphate (CTP) must be converted to CMP-SA by the enzyme, CMP-sialic acid (CMP-SA) synthetase (Schachter et al. (1973) *Metabolic Conjugation and metabolic Hydrolysis* (New York Academic Press) 2–135):

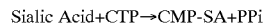

Sialic Acid+CTP→CMP-SA+PPi

This enzyme has been cloned and sequenced from *E. coli* and used for the in vitro production of CMP-SA, as described in Zapata et al. (1989) *J. Biol. Chem.* 264:14769–14774, Kittleman et al. (1995) *Appl. Microbiol. Biotechnol.* 44:59–67, Ichikawa et al. (1992) *Anal. Biochem.* 202:215–238, Shames et al. (1991) *Glycobiology* 1:187–191; the contents of which are herein incorporated by reference).

In eukaryotes, the activated sugar nucleotide, CMP-SA, must be transported into the Golgi lumen for sialylation to proceed (Deutscher et al. (1984) *Cell* 39:295–299). Transport through the trans-Golgi membrane is facilitated by the CMP-SA transporter protein, which was identified by complementation cloning into sialylation deficient CHO cells (Eckhardt et al. (1996) *Proc. Natl. Acad. Sci. USA* 93:7572–7576). This mammalian gene has also been cloned and expressed in a functional form in the heterologous host, *S. cerevisiae* (Bernisone et al. (1997) *J. Biol. Chem.* 272:12616–12619).

In addition to feeding of external precursor substrates such as ManNAc, GlcNAc, or glucosamine to increase CMP-SA levels, a supplementary approach in which CMP-SA transporter genes are introduced and expressed using routine recombinant DNA techniques may also be employed according to the methods of the present invention. These techniques are optionally combined with ManNAc, GlcNAc, or glucosamine feeding strategies described above, to maximize CMP-SA production.

Conversion of GlcNAc or Glucosamine to ManNAc

Figure 23:
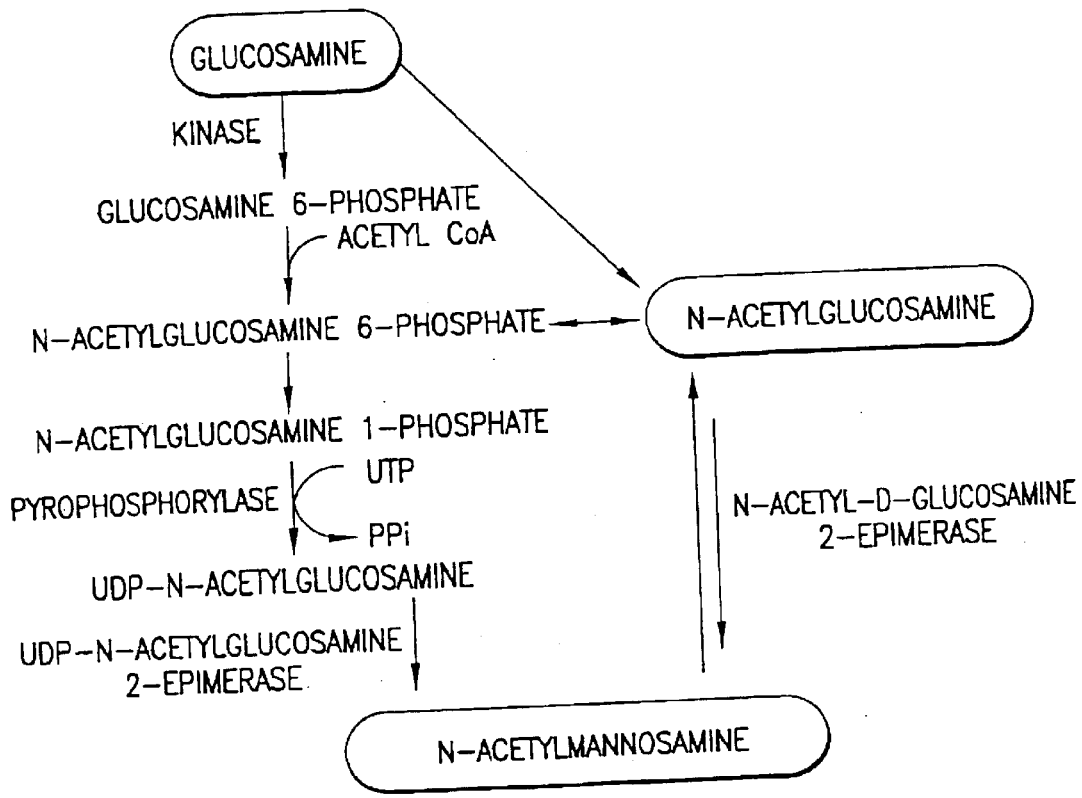
FIG. 23 depicts a metabolic pathway for ManNAc (N-acetylmannosamine) from glucosamine and N-acetylglucosamine (GlcNAc).

Also according to the methods of the present invention, where the utilization of GlcNAc or glucosamine is preferred and ManNAc is not generated naturally in insect cells, ManNAc can be produced chemically using sodium hydroxide (Mahmoudian et al. (1997) *Enzyme and Microbial Technology* 20:393–400). Alternatively, the enzymes that convert these substrates to ManNAc or fragments or variants of these enzymes, can be expressed in insect cells using techniques described herein or otherwise known in the art. The production of ManNAc from GlcNAc and glucosamine proceeds through the metabolic pathway shown in FIG. 23.

Two approaches are provided to accomplish this conversion: (a) direct epimerization of GlcNAc; or (b) conversion of GlcNAc or glucosamine to UDP-N-acetylglucosamine (UDP-GlcNAc), and then ManNAc. According to one embodiment of the invention, approach (a) is achieved using the gene encoding a GlcNAc-2-epimerase isolated from pig kidney, or fragments or variants thereof, to directly convert GlcNAc to ManNAc (See Maru et al. (1996) *J. Biol. Chem.* 271:16294–16299; the contents of which are herein incorporated by reference). Additionally, the sequence for a homologue of this enzyme can be routinely obtained from bioinformatics databases, and cloned into baculovirus vectors, or stably integrated into insect cells using techniques described herein or otherwise known in the art.

Alternatively, approach (b) requires insertion of the gene to convert UDP-GlcNAc to ManNAc. Engineering the production of UDP-GlcNAc from glucosamine or GlcNAc is likely not required since most insect cells comprise metabolic pathways to synthesize UDP-GlcNAc; as indicated by the presence of GlcNAc-containing oligosaccharides. According to one embodiment of the invention, the gene encoding a rat bifunctional enzyme coding for conversion of UDP-GlcNAc to ManNAc and ManNAc to ManNAc-6-P, or fragments or variants thereof is used to engineer the production of UDP-GlcNAc using techniques described herein or otherwise known in the art (Stasche et al. (1997) *J. Biol. Chem.* 272:24319–24324, the contents which are herein incorporated by reference). In a specific embodiment, the segment of this enzyme responsible for conversion of UDP-GlNAc to ManNAc may be expressed independently in insect cells using techniques known in the art to produce ManNAc rather than ManNAc-6-P.

Conversion of ManNAc to SA

Figure 24:
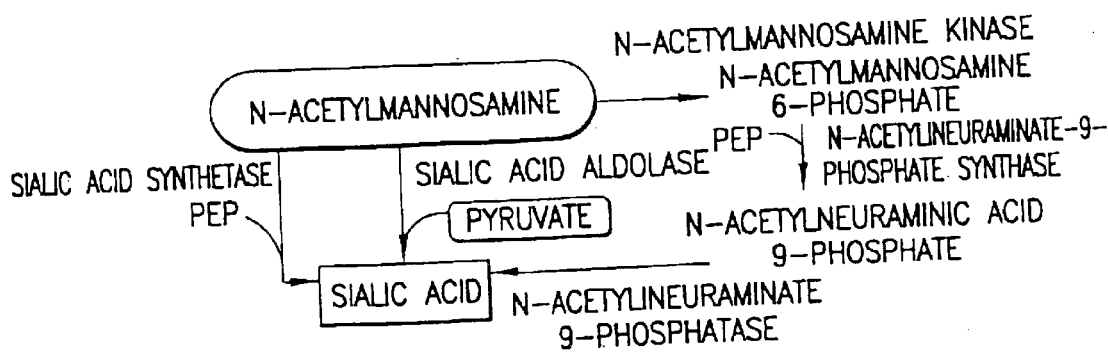
FIG. 24 depicts a ManNAc (N-acetylmannosamine) to sialic acid metabolic pathway.

Once ManNAc is generated, it is converted to SA according to the methods of the invention. There are three possible metabolic pathways for the conversion of ManNAc to SA in bacteria and mammals, as shown in FIG. 24. Negligible SA levels have previously been observed in insect cells (in the absence of exogenous supplementation of ManNAc to the culture media).

The conversion of ManNAc and PEP to SA using sialic acid synthetase is the predominant pathway for SA production in *E. coli* (Vann et al. (1997) *Glycobiology* 7:697–701). The *E. coli* sialic acid (SA) synthetase gene NeuB (SEQ ID NO:7 and 8) has been cloned and sequenced and is commercially, publicly, and/or otherwise available for the purposes of the present invention. Additionally, as disclosed herein, the human sialic acid synthetase gene has also been cloned (cDNA clone HA5AA37), sequenced, and deposited with the American Type Culture Collection ("ATCC") on Feb. 24, 2000 and was given the ATCC Deposit Number PTA-1410. (The ATCC is located at 10801 University Boulevard, Manassas, Va. 20110–2209, USA. ATCC deposits were made pursuant to the terms of the Budapest Treaty on the international recognition of the deposit of microorganisms for purposes of patent procedure.) Thus, for enhancing expression of SA synthetase according to certain embodiments of the invention, the nucleic acid compositions encoding a SA synthetase such as, for example, an *E. coli* and/or human sialic acid synthetase and/or a fragment or variant thereof, may be inserted into a host expression vector or into the host genome using techniques described herein or otherwise known in the art. According to the methods of the invention, the production of SA can also be achieved from ManNAc and pyruvate using an aldolase, such as, for example, bacterial aldolase (Mahmoudian et al. (1997) *Enzyme and Microbial Technology* 20:393–400), or a human aldolase (as described herein) or fragment or variant thereof. The human aldolase gene has been cloned (cDNA clone HDPAK85), sequenced, and deposited with the American Type Culture Collection ("ATCC") on Feb. 24, 2000 and was given the ATCC Deposit Number PTA-1410. Thus, the aldolase enzyme is considered as an alternative for converting ManNAc to SA. For enhancing expression of aldolase, the aldolase sequences can be amplified directly from *E. coli* and human DNA using primers and PCR amplification as described in Mahmoudian et al. (Mahmoudian et al. (1997) *Enzyme and Microbial Technology* 20:393–400); the contents of which are herein incorporated by reference) and herein, and using techniques described herein or otherwise known in the art to enhance expression of aldolase, or a fragment or variant thereof. Since the aldolase reaction is reversible, high levels of added ManNAc and pyruvate, may be used according to the methods of the invention to drive this reversible reaction in the direction of the product SA (Mahmoudian et al. (1997) *Enzyme and Microbial Technology* 20:393–400).

In addition to the pathways which convert ManNAc to SA present in both prokaryotes and eukaryotes, an exclusively eukaryotic pathway may also employed according to the methods of the invention to convert ManNAc to SA through the phosphate intermediates ManNAc-6-phosphate and SA-9-phosphate. It is recognized that the mammalian enzymes (synthetase and phosphatase) responsible for converting ManNAc to SA through phosphate intermediates can be utilized for engineering this eukaryotic pathway into insect cells.

Conversion of SA to CMP-SA

Figure 25:
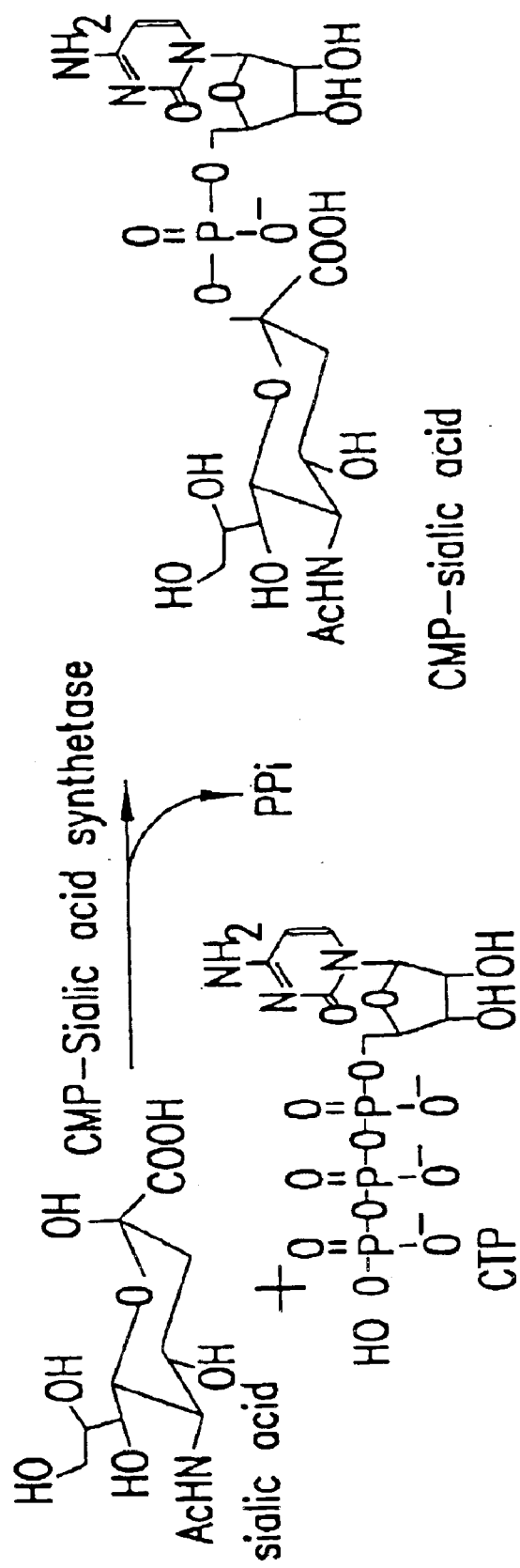
FIG. 25 depicts the formation of CMP-sialic acid (CMP-SA) catalyzed by CMP-SA synthetase.

The methods of the invention also encompass the use of CMP-SA synthetase to enzymatically converts SA to CMP-SA (see, e.g., the reaction shown in FIG. 25). However, insect cells, such as, for example, Sf9 insect cells, have negligible endogenous CMP-SA synthetase activity. Evidence of limited CMP-SA synthetase in insect cells is also demonstrated by increased SA levels found following substrate feeding and genetic manipulation without a concomitant increase in CMP-SA.

Thus, specific embodiments of the invention provide methods for enhancing the expression of CMP-SA synthetase, and/or fragments or variants thereof. Bacterial CMP-SA synthetase has been cloned and sequenced as described in Zapata et al. (1989) *J. Biol. Chem.* 264:14769–14774; the contents of which are herein incorporated by reference. Additionally, as described herein the gene encoding human CMP-SA synthetase has also been cloned (cDNA clone HWLLM34), sequenced and deposited with the American Type Culture Collection ("ATCC") on Feb. 24, 2000 and was given the ATCC Deposit Number PTA-1410. Thus, in specific embodiments, the methods of the present invention provide for enhancing expression of bacterial or human CMP-SA synthetase or fragments, or variants thereof, in cells of interest, such as, for example, in insect cells, using techniques described herein, or otherwise known in the art.

Golgi Transport of CMP-SA

CMP-SA must be delivered into the Golgi apparatus in order for sialylation to occur, and this transport process depends on the presence of the CMP-SA transporter protein (Deutscher et al. (1984) *Cell* 39:295–299). To determine if CMP-SA synthesized in insect cells is efficiently transported into the proper cellular compartment, insect cell vesicles are prepared and transport of CMP-SA is measured as described in (Bernisone et al. (1997) *J. Biol. Chem.* 272:12616–12619) and/or using techniques otherwise known in the art. Where the native enzymatic transport is lower than desired, a transporter enzyme is cloned and expressed in insect cells using the known mammalian gene sequence (as described in Bernisone et al. (1997) *J. Biol. Chem.* 272:12616–12619, Eckhardt et al. (1996) *Proc. Natl. Acad. Sci. USA* 93:7572–7576; the contents of which are herein incorporated by reference) and/or sequences otherwise known in the art. Corresponding sequences are available from bioinformatics databases for the purposes of this invention. Localization of the protein to the Golgi is evaluated using an antibody generated against the heterologous protein using techniques known in the art in concert with commercially available fluorescent probes that identify the Golgi apparatus.

Expression cloning of multiple transcripts (for example, transcripts encoding CMP-SA pathway enzymes, glycosyl transferases, and ribozymes or anti-sense RNAs to suppress hexosaminidases) in a single cell line using techniques known in the art may be required to bring about the desired sialylation reactions and/or to optimize these reactions. Alternatively, co-infection of cells with multiple viruses using techniques known in the art can also be used to simultaneously produce multiple recombinant transcripts. In addition, plasmids that incorporate multiple foreign genes including some under the control of the early promoter IE1 are commercially, publicly, or otherwise available for the purposes of the invention, and can be used to create baculovirus constructs. The present invention encompasses using any of these techniques. The invention also encompasses using the above mentioned types of vectors to enable expression of desired carbohydrate processing enzymes in baculovirus infected insect cells prior to production of a heterologous glycoprotein of interest under control of the very late polyhedrin promoter. In this manner, once the desired polypeptide is synthesized essential N-glycan processing enzymes can facilitate N-glycan processing once the glycoprotein of interest.

Alternatively, genes for some of the enzymes may be incorporated directly into the insect cell genome using vectors known in the art, such as, for example, vectors similar to those described in (Jarvis et al. (1990) *Bio/Technology* 8:950–955, Jarvis et al. (1995) *Baculovirus Expr. Protocols* ed. 39:187–202). Genomic integration eliminates the need to infect the cells with a large number of viral constructs. These constructs for genomic integration contain one or more early viral promoters, including AcMNPV IE1 and 39K, which provide constitutive expression in transfected insect cells (Jarvis et al. (1990) Bio/Technology 8:950–955). In addition, a sequential transformation strategy may routinely be developed for producing stable transformants that constitutively express up to four different heterologous genes simultaneously. These vectors and transformation techniques are provided for the purposes of this invention. In this manner, incorporation of plasmids containing heterologous genes into the insect cell genome combined with baculovirus infection integrates the metabolic pathways leading to efficient acceptor and donor substrate production in insect cells.

Generation of N-Linked Sialylated Glycoproteins

The final step in the generation of sialylated glycoproteins or glycolipids in mammalian cells is the enzymatic transfer of sialic acid from the donor substrate, CMP-SA, onto an acceptor substrate in the Golgi apparatus; a reaction which is catalyzed by sialyltransferase. The sialic acid (SA) residues occurring in N-linked glycoproteins are alpha-linked to the 3 or 6 position of the GalGlcNAc sugars (Tsuji, S. (1996) *J. Biochem.* 120:1–13). The SA alpha2-3GalGlcNAc linkage is found in heterologous glycoproteins expressed by CHO and human cells and the SA alpha2-6GalGlcNAc linkage is found in many human glycoproteins (Goochee et al. (1991) *Bio/technology* 9:1347–1355). The alpha2-3- and/or alpha2-6-sialyltransferase genes along with a number of other sialyltransferase genes have been cloned, sequenced and expressed as active heterologous proteins as described in Lee et al. (1989) *J. Biol. Chem.* 264:13848–13855, Ichikawa et al. (1992) *Anal. Biochem.* 202:215–238, Tsuji, S. (1996) *J. Biochem.* 120:1–13; U.S. Pat. No. 5,047,335, the contents of which are herein incorporated by reference. Any one or more of these genes, as well as fragments, and/or variants thereof may be introduced and expressed in cells of interest using techniques described herein or otherwise known in the art, and may be used according to the methods of the present invention to enhance the enzymatic transfer of sialic acid from the donor substrate.

For generating N-Linked sialylated glycoproteins in insect cells, once the donor (CMP-SA) and acceptor (GalGlcNAc-R) substrates are produced as described above, the methods of the invention further comprise expression of a sialyltransferase or fragment or variant thereof, in the cells. The completion of the sialylation reaction can be verified by elucidating the N-glycan structures attached to a desired glycoprotein using techniques described herein or otherwise known in the art. It is recognized that evaluation of N-glycans attachments may also suggest additional metabolic engineering strategies that can further enhance the level of sialylation in insect cells.

It is observed that unmodified *T. ni* insect cell lysates failed to generate any sialylated compounds when incubated with the substrate, LacMU, and the nucleotide sugar, CMP-SA. Thus, it is concluded that these cells comprise negligible native sialyltransferase activity. However, infection of insect cells with a baculovirus containing alpha2,3 sialyltransferase provided significant enzymatic conversion of LacMU and CMP-SA to sialylLacMU. For the purposes of the invention, heterologous sialyltransferase can be expressed using techniques described herein or otherwise known in the art either by co-infection with a virus coding for sialyltransferase, or fragment, or variant thereof, or by using stable transfectants expressing the enzyme. In addition to the 2,3 sialyltransferase baculovirus constructs, baculovirus vectors comprising sequences coding for alpha2,6 sialyltransferase and/or fragments or variants thereof as well as stably transformed insect cells stably expressing both gal T and sialyltransferase are commercially, or publicly available, and/or may routinely be generated using techniques described herein or otherwise known in the art. Evaluation of sialyltransferase activity is determined using the FRET or HPLC assays described herein and/or using other assays known in the art. Localization of the sialyltransferase to the Golgi is accomplished using anti-sialyltransferase antibodies commercially, publicly, or otherwise available for the purpose of this invention in concert with Golgi specific marker proteins.

For the purposes of enhancing carbohydrate processing enzymes of the invention, suppressing activity of endogenous N-acetylglucosaminidase, expressing heterologous proteins in the cells of the invention, and constructing vectors for the purposes of the invention; genetic engineering methods are known to those of ordinary skill in the art. For example, see Schneider, A. et al., (1998) *Mol. Gen. Genet.* 257:308–318. Where the invention encompasses utilizing baculovirus based expression, such methods are known in the art, for example, as described in O'Riley et al. (1992) *Baculovirus Expression Vectors*, W. H. Freeman and Company, New York 1992.

For the purposes of enhancing carbohydrate processing enzymes of the invention, suppressing activity of endogenous N-acetylglucosaminidase, expressing heterologous proteins in the cells of the invention, and constructing vectors as described herein, known sequences can be utilized in the methods of the invention, including but not limited to the sequences described in GenSeq accession No. Z11234 and Z11235 for two human galactosyltransferases (see also U.S. Pat. No. 5,955,282; the contents of which are herein incorporated by reference); and/or in Genbank accession No. D83766 for GlcNAc-2-epimerase, Y07744 for the bifunctional rate liver enzyme capable of catalyzing conversion of UDP-GlcNAc to ManNAc, J05023 for *E. coli* CMP-SA synthetase, AJ006215 for murine CMP-SA synthetase, Z71268 for murine CMP-SA transporter, X03345 for *E. coli* aldolase, U05248 for *E. coli* SA synthetase, X17247 for human 2,6 sialyltransferase, L29553 for human 2,3 sialyltransferase, M13214 for bovine galactosyltransferase, L77081 for human GlcNAc T-I, U15128 or L36537 for human GlcNAc T-II, D87969 for human CMP-SA transporter, and S95936 for human transferrin; and fragments or variants of the enzymes that display one or more of the biological activities of the enzymes (such biological activities may routinely be assayed using techniques described herein or otherwise known in the art). The sequences described above are readily accessible using the provided accession number in the NCBI Entrez database, known to the person of ordinary skill in the art.

Thus, one aspect of the invention provides for use of isolated nucleic acid molecules comprising polynucleotides having nucleotide sequences selected from the group consisting of: (a) nucleotide sequences encoding a biologically active fragment or variant of the polypeptide having the amino acid sequence described in GenSeq accession No. Z11234 and Z11235 for two human galactosyltransferases; and/or in Genbank accession No. D83766 for GlcNAc-2-epimerase, Y07744 for the bifunctional rate liver enzyme capable of catalyzing conversion of UDP-GlcNAc to ManNAc, J05023 for *E. coli* CMP-SA synthetase, AJ006215 for murine CMP-SA synthetase, Z71268 for murine CMP-SA transporter, X03345 for *E. coli* aldolase, U05248 for *E. coli* SA synthetase, X17247 for human 2,6 sialyltransferase, L29553 for human 2,3 sialyltransferase, M13214 for bovine galactosyltransferase, L77081 for human GlcNAc T-I, U15128 or L36537 for human GlcNAc T-II, D87969 for human CMP-SA transporter, and/or S95936 for human transferrin; (b) nucleotide sequences encoding an antigenic fragment of the polypeptide having the amino acid sequence described in GenSeq accession No. Z11234 and Z11235 for two human galactosyltransferases (see also U.S. Pat. No. 5,955,282; the contents of which are herein incorporated by reference); and/or in Genbank accession No. D83766 for GlcNAc-2-epimerase, Y07744 for the bifunctional rate liver enzyme capable of catalyzing conversion of UDP-GlcNAc to ManNAc, J05023 for *E. coli* CMP-SA synthetase, AJ006215 for murine CMP-SA synthetase, Z71268 for murine CMP-SA transporter, X03345 for*E. coli* aldolase, U05248 for *E. coli* SA synthetase, X17247 for human 2,6 sialyltransferase, L29553 for human 2,3 sialyltransferase, M13214 for bovine galactosyltransferase, L77081 for human GlcNAc T-I, U15128 or L36537 for human GlcNAc T-II, D87969 for human CMP-SA transporter, and/or S95936 for human transferrin; and (c) nucleotide sequences complementary to any of the nucleotide sequences in (a) or (b), above. Polypeptides encoded by such nucleic acids may also be used according to the methods of the present invention. Further embodiments of the invention include use of isolated nucleic acid molecules that comprise a polynucleotide having a nucleotide sequence at least 80%, 85%, or 90% identical, and more preferably at least 95%, 97%, 98% or 99% identical, to any of the above nucleotide sequences, or a polynucleotide which hybridizes under stringent hybridization conditions to a polynucleotide that is complementary to any of the above nucleotide sequences. This polynucleotide which hybridizes does not hybridize under stringent hybridization conditions to a polynucleotide having a nucleotide sequence consisting of only A residues or of only T residues. Polypeptides encoded by such nucleic acids may also be used according to the methods of the present invention. Preferably, the nucleic acid sequences (including fragments or variants) that may be used according to the methods of the present invention encode a polypeptide having a biological activity. Such biological activity may routinely be assayed using techniques described herein or otherwise known in the art.

In addition to the sequences described above, the nucleotide sequences and amino acid sequences disclosed in FIGS. 27–32, and fragments and variants of these sequences may also be used according to the methods of the invention.

In one embodiment, specific enzyme polypeptides comprise the amino acid sequences shown in FIGS. 28, 30 and 32; or otherwise described herein. However, the invention also encompasses sequence variants of the polypeptide sequences shown in FIGS. 28, 30 and 32.

In a specific embodiment, one, two, three, four, five or more human polynucleotide sequences, or fragments, or variants thereof, and/or the polypeptides encoded thereby, are used according to the methods of the present invention to convert ManNAc to SA (see Example 6). Such polynucleotide and polypeptide sequences include, but are not limited to, sequences corresponding to human aldolase (SEQ ID NO:1 and SEQ ID NO:2), human CMP-SA synthetase (SEQ ID NO:3 and SEQ ID NO:4), and human SA synthetase (SEQ ID NO:5 and SEQ ID NO:6); see also FIGS. 27–32. Thus, in certain embodiments the methods of present invention include the use of one or more novel isolated nucleic acid molecules comprising polynucleotides encoding polypeptides important to intracellular carbohydrate processing in humans. Such polynucleotide sequences include those disclosed in the figures and/or Sequence Listing and/or encoded by the human cDNA plasmids (Human CMP-Sialic Acid Synthetase, cDNA clone HWLLM34; Human Sialic Acid Synthetase, cDNA clone HA5AA37; and Human Aldolase cDNA clone HDPAK85) deposited with the American Type Culture Collection (ATCC) on Feb. 24, 2000 and receiving accession numbers PTA-1410. The present invention further includes the use of polypeptides encoded by these polynucleotides. The present invention also provides for use of isolated nucleic acid molecules encoding fragments and variants of these polypeptides, and for the polypeptides encoded by these nucleic acids.

Thus, one aspect of the invention provides for use of isolated nucleic acid molecules comprising polynucleotides having nucleotide sequences selected from the group consisting of: (a) nucleotide sequences encoding human aldolase having the amino acid sequences as shown in SEQ ID NO:2; (b) nucleotide sequences encoding a biologically active fragment of the human aldolase polypeptide having the amino acid sequence shown in SEQ ID NO:2; (c) nucleotide sequences encoding an antigenic fragment of the human aldolase polypeptide having the amino acid sequence shown in SEQ ID NO:2; (d) nucleotide sequences encoding the human aldolase polypeptide comprising the complete amino acid sequence encoded by the plasmid contained in the ATCC Deposit; (e) nucleotide sequences encoding a biologically active fragment of the human aldolase polypeptide having the amino acid sequence encoded by the plasmid contained in the ATCC Deposit; (f) a nucleotide sequence encoding an antigenic fragment of the human aldolase polypeptide having the amino acid sequence encoded by the plasmid contained in the ATCC Deposit; and (g) nucleotide sequences complementary to any of the nucleotide sequences in (a) through (f), above. Polypeptides encoded by such nucleic acids may also be used according to the methods of the present invention. Further embodiments of the invention include use of isolated nucleic acid molecules that comprise a polynucleotide having a nucleotide sequence at least 80%, 85%, or 90% identical, and more preferably at least 95%, 97%, 98% or 99% identical, to any of the nucleotide sequences in (a), (b), (c), (d), (e), (f), or (g), above, or a polynucleotide which hybridizes under stringent hybridization conditions to a polynucleotide in (a), (b), (c), (d), (e), (f), or (g), above. This polynucleotide which hybridizes does not hybridize under stringent hybridization conditions to a polynucleotide having a nucleotide sequence consisting of only A residues or of only T residues. Polypeptides encoded by such nucleic acids may also be used according to the methods of the present invention.

Another aspect of the invention provides for use of isolated nucleic acid molecules comprising polynucleotides having nucleotide sequences selected from the group consisting of: (a) nucleotide sequences encoding human CMP-SA synthetase having the amino acid sequences as shown in SEQ ID NO:4; (b) nucleotide sequences encoding a biologically active fragment of human CMP-SA synthetase polypeptide having the amino acid sequence shown in SEQ ID NO:4; (c) nucleotide sequences encoding an antigenic fragment of the human CMP-SA synthetase polypeptide having the amino acid sequence shown in SEQ ID NO:4; (d) nucleotide sequences encoding the human CMP-SA synthetase polypeptide comprising the complete amino acid sequence encoded by the plasmid contained in the ATCC Deposit; (e) nucleotide sequences encoding a biologically active fragment of the human CMP-SA synthetase polypeptide having the amino acid sequence encoded by the plasmid contained in the ATCC Deposit; (f) a nucleotide sequence encoding an antigenic fragment of the human CMP-SA synthetase polypeptide having the amino acid sequence encoded by the plasmid contained in the ATCC Deposit; and (g) nucleotide sequences complementary to any of the nucleotide sequences in (a) through (f), above. Polypeptides encoded by such nucleic acids may also be used according to the methods of the present invention. Further embodiments of the invention include use of isolated nucleic acid molecules that comprise a polynucleotide having a nucleotide sequence at least 80%, 85%, or 90% identical, and more preferably at least 95%, 97%, 98% or 99% identical, to any of the nucleotide sequences in (a), (b), (c), (d), (e), (f), or (g) above, or a polynucleotide which hybridizes under stringent hybridization conditions to a polynucleotide in (a), (b), (c), (d), (e), (f), or (g), above. This polynucleotide which hybridizes does not hybridize under stringent hybridization conditions to a polynucleotide having a nucleotide sequence consisting of only A residues or of only T residues. Polypeptides encoded by such nucleic acids may also be used according to the methods of the present invention.

Another aspect of the invention provides for use of isolated nucleic acid molecules comprising polynucleotides having nucleotide sequences selected from the group consisting of: (a) nucleotide sequences encoding human SA synthetase having the amino acid sequences as shown in SEQ ID NO:6; (b) nucleotide sequences encoding a biologically active fragment of the human SA synthetase polypeptide having the amino acid sequence shown in SEQ ID NO:6; (c) nucleotide sequences encoding an antigenic fragment of the human SA synthetase polypeptide having the amino acid sequence shown in SEQ ID NO:6; (d) nucleotide sequences encoding the human SA synthetase polypeptide comprising the complete amino acid sequence encoded by the plasmid contained in the ATCC Deposit; (e) nucleotide sequences encoding a biologically active fragment of the human SA synthetase polypeptide having the amino acid sequence encoded by the plasmid contained in the ATCC Deposit; (f) a nucleotide sequence encoding an antigenic fragment of the human SA synthetase polypeptide having the amino acid sequence encoded by the plasmid contained in the ATCC Deposit; and (g) nucleotide sequences complementary to any of the nucleotide sequences in (a) through (f), above. Polypeptides encoded by such nucleic acids may also be used according to the methods of the present invention. Further embodiments of the invention include use of isolated nucleic acid molecules that comprise a polynucleotide having a nucleotide sequence at least 80%, 85%, or 90% identical, and more preferably at least 95%, 97%, 98% or 99% identical, to any of the nucleotide sequences in (a), (b), (c), (d), (e), (f), or (g) above, or a polynucleotide which hybridizes under stringent hybridization conditions to a polynucleotide in (a), (b), (c), (d), (e), (f), or (g), above. This polynucleotide which hybridizes does not hybridize under stringent hybridization conditions to a polynucleotide having a nucleotide sequence consisting of only A residues or of only T residues. Polypeptides encoded by such nucleic acids may also be used according to the methods of the present invention.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the described polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, such as, for example, that shown of SEQ ID NO:1, the ORF (open reading frame), or any fragment as described herein.

As a practical matter, whether any particular nucleic acid molecule or polypeptide is at least, for example, 80%, 85%, 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237–245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/ alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least, for example, 80%, 85%, 90%, 95%, 96%, 97%, 98% or 99% identical to, for example, the amino acid sequences of SEQ ID NO:2 or to the amino acid sequence encoded by the cDNA contained in a deposited clone can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. 6:237–245(1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

In another embodiment of the invention, to determine the percent homology of two amino acid sequences, or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As used herein, amino acid or nucleic acid "homology" is equivalent to amino acid or nucleic acid "identity". The percent homology between the two sequences is a function of the number of identical positions shared by the sequences (i.e., percent homology equals the number of identical positions/total number of positions times 100).

Variants of above described sequences include a substantially homologous protein encoded by the same genetic locus in an organism, i.e., an allelic variant. Variants also encompass proteins derived from other genetic loci in an organism, but having substantial homology to the proteins of FIGS. 27–32, or otherwise described herein. Variants also include proteins substantially homologous to the protein but derived from another organism, i.e., an ortholog. Variants also include proteins that are substantially homologous to the proteins that are produced by chemical synthesis. Variants also include proteins that are substantially homologous to the proteins that are produced by recombinant methods. As used herein, two proteins (or a region of the proteins) are substantially homologous when the amino acid sequences are at least about 55–60%, typically at least about 70–75%, more typically at least about 80–85%, and most typically at least about 90–95% or more homologous. A substantially homologous amino acid sequence, according to the present invention, will be encoded by a nucleic acid sequence hybridizing to the nucleic acid sequence, or portion thereof, of the sequence shown in FIGS. 27, 28, 31 or otherwise described herein under stringent conditions as more fully described below.

Orthologs, homologs, and allelic variants that are encompassed by the invention and that may be used according to the methods of the invention can be identified using methods well known in the art. These variants comprise a nucleotide sequence encoding a protein that is at least about 55%, typically at least about 70–75%, more typically at least about 80–85%, and most typically at least about 90–95% or more homologous to the nucleotide sequence shown in FIGS. 27, 29, 31, or otherwise described herein, or a fragment of this sequence. Such nucleic acid molecules can readily be identified as being able to hybridize under stringent conditions, to the nucleotide sequence shown in FIGS. 27, 29, 31, or complementary sequence thereto, or otherwise described herein, or a fragment of the sequence. It is understood that stringent hybridization does not indicate substantial homology where it is due to general homology, such as poly A sequences, or sequences common to all or most proteins in an organism or class of proteins.

The invention also encompasses polypeptides having a lower degree of identity but having sufficient similarity so as to perform one or more of the same functions performed by the enzyme polypeptides described herein. Similarity is determined by conserved amino acid substitution. Such substitutions are those that substitute a given amino acid in a polypeptide by another amino acid of like characteristics (see Table 1). Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr. Guidance concerning which amino acid changes are likely to be phenotypically silent are found in Bowie et al., Science 247:1306–1310 (1990).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Both identity and similarity can be readily calculated (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). Preferred computer program methods to determine identify and similarity between two sequences include, but are not limited to, GCG program package (Devereux, J. (1984) *Nuc. Acids Res.* 12(1):387), BLASTP, BLASTN, FASTA (Atschul, S. F. (1990) *J. Molec. Biol.* 215:403).

A variant polypeptide can differ in amino acid sequence by one or more substitutions, deletions, insertions, inversions, fusions, and truncations or a combination of any of these.

Variant polypeptides can be fully functional or can lack function in one or more activities. Thus, in the present case, variations can affect the function, for example, of one or more of the modules, domains, or functional subregions of the enzyme polypeptides of the invention. Preferably, polypeptide variants and fragments have the described activities routinely assayed via bio assays described herein or otherwise known in the art.

Fully functional variants typically contain only conservative variation or variation in non-critical residues or in non-critical regions. Functional variants can also contain substitution of similar amino acids, which result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region. As indicated, variants can be naturally-occurring or can be made by recombinant means or chemical synthesis to provide useful and novel characteristics for the polypeptide.

Amino acids that are essential for function can be identified by methods known in the art, such as site-directed mutagenesis or alanine-scanning mutagenesis (Cunningham et al., Science 244:1081–1085 (1989)). The latter procedure introduces single alanine mutations at every residue in the molecule. The resulting mutant molecules are then tested for biological activity. Sites that are critical can also be determined by structural analysis such as crystallization, nuclear magnetic resonance or photoaffinity labeling (Smith et al., J. Mol. Biol. 224:899–904 (1992); de Vos et al. Science 255:306–312 (1992)).

The invention further encompasses variant polynucleotides, and fragments thereof, that differ from the nucleotide sequence, such as, for example, those shown in FIGS. 27, 29, 31 or otherwise described herein, due to degeneracy of the genetic code and thus encode the same protein as that encoded by the nucleotide sequence shown in FIGS. 27, 29, 31 or otherwise described herein.

The invention also provides nucleic acid molecules encoding the variant polypeptides described herein. Such polynucleotides may be naturally occurring, such as allelic variants (same locus), homologs (different locus), and orthologs (different organism), or may be constructed by recombinant DNA methods or by chemical synthesis. Such non-naturally occurring variants may be made by mutagenesis techniques, including those applied to polynucleotides, cells, or organisms. Accordingly, as discussed above, the variants can contain nucleotide substitutions, deletions, inversions and insertions.

Variation can occur in either or both the coding and non-coding regions. The variations can produce both conservative and non-conservative amino acid substitutions.

"Polynucleotides" or "nucleic acids" that may be used according to the methods of the invention also include those polynucleotides capable of hybridizing, under stringent hybridization conditions, to sequences contained in SEQ ID NO:1, the complement thereof, or a cDNA within the deposited plasmids. As used herein, the term "hybridizes under stringent conditions" is intended to describe conditions for hybridization and washing under which nucleotide sequences encoding a receptor at least 55% homologous to each other typically remain hybridized to each other. The conditions can be such that sequences at least about 65%, at least about 70%, or at least about 75% or more homologous to each other typically remain hybridized to each other. Such stringent conditions are known to those skilled in the art and can be found in Current Protocols in Molecular Biology, John Wiley & Sons, N.Y. (1989), 6.3.1–6.3.6. One example of stringent hybridization conditions are hybridization in 6×sodium chloride/sodium citrate (SSC) at about 45 degrees C., followed by one or more washes in 0.2×SSC, 0.1% SDS at 50–65 degrees C.

Also contemplated for use according to the methods of the invention are nucleic acid molecules that hybridize to a polynucleotide disclosed herein under lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20× SSPE=3M NaCl; 0.2M NaH$_2$PO$_4$; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo-dT as a primer).

In one embodiment, an isolated nucleic acid molecule that hybridizes under stringent conditions to a sequence disclosed herein, or the complement thereof, such as, for example, the sequence of FIGS. 27, 29, 31, corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

The present invention also encompasses recombinant vectors, which include the isolated nucleic acid molecules and polynucleotides that may be used according to the methods of the present invention, and to host cells containing the recombinant vectors and/or nucleic acid molecules, as well as to methods of making such vectors and host cells and for using them for production of glycosylation enzyme by recombinant techniques. Polypeptides produced by such methods are also provided.

The invention encompasses utilizing vectors for the maintenance (cloning vectors) or vectors for expression (expression vectors) of the desired polynucleotides encoding the carbohydrate processing of the invention, or those encoding proteins to be sialylated by the methods of the invention and/or by expression of the proteins the cells of the invention. The vectors can function in prokaryotic or eukaryotic cells or in both (shuttle vectors).

In one embodiment, one or more of the polynucleotide sequences used according to the methods of the invention are inserted into commercially, publicly, or otherwise available baculovirus expression vectors for enhanced expression of the corresponding enzyme. In another non-exclusive embodiment, one ore more of the polynucleotides used according to the methods of the invention are inserted into other viral vectors or for generation of stable insect cell lines. Techniques known in the art, such as, for example, HPAEC and HPLC techniques, may be routinely used to evaluate the enzymatic activity of these enzymes from both eukaryotic and bacterial sources to determine which source is best for generating SA in insect cells.

Generally, expression vectors contain cis-acting regulatory regions that are operably linked in the vector to the polynucleotide to be expressed, or other relevant polynucleotides such that transcription of the polynucleotides is allowed in a host cell. The polynucleotides can be introduced into the host cell with a separate polynucleotide capable of affecting transcription. Thus, the second polynucleotide may provide a trans-acting factor interacting with the cis-regulatory control region to allow transcription of the polynucleotides from the vector. Alternatively, a trans-acting factor may be supplied by the host cell. Finally, a trans-acting factor can be produced from the vector itself.

It is understood, however, that in some embodiments, transcription of the polynucleotides can occur in a cell-free system.

The regulatory sequence to which the polynucleotides described herein can be operably linked include, for example, promoters for directing mRNA transcription. These promoters include, but are not limited to, baculovirus promoters including, but not limited to, 1E0, 1E1, 1E2, 39k, 35k, egt, ME53, ORF 142, PE38, p6.9, capsid, gp64 polyhedrin, p10, basic and core; and insect cell promoters including, but not limited to, *Drosophila* actin, metallothionine, and the like. Where the host cell is not an insect cell, such promoters include, but are not limited to, the left promoter from bacteriophage lambda, the lac, TRP, and TAC promoters from *E. coli*, promoters from *Actinomycetes*, including *Nocardia*, and *Streptomyces*.

Promoters may be isolated, if they have not already been isolated, by standard promoter identification and trapping methods known in the art, see, for example, in Sambrook et al., *Molecular Cloning: A Laboratory Manual* 2nd. ed., Cold Spring Harbor Laboratory Press, Cold Spring Harbor, N.Y., (1989).

It would be understood by a person of ordinary skill in the art that the choice of promoter would depend upon the choice of host cell. Similarly, the choice of host cell will depend upon the use of the host cell. Accordingly, host cells can be used for simply amplifying, but not expressing, the nucleic acid. However, host cells can also be used to produce desirable amounts of the desired polypeptide. In this embodiment, the host cell is simply used to express the protein per se. For example, amounts of the protein could be produced that enable its purification and subsequent use, for example, in a cell free system. In this case, the promoter is compatible with the host cell. Host cells can be chosen from virtually any of the known host cells that are manipulated by the methods of the invention to produce the desired glycosylation patterns. These could include mammalian, bacterial, yeast, filamentous fungi, or plant cells.

In addition to control regions that promote transcription, expression vectors may also include regions that modulate transcription, such as repressor binding sites and enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., cited above.

Depending on the choice of a host cell, a variety of expression vectors can be used to express the polynucleotide. Such vectors include chromosomal, episomal, and particularly virus-derived vectors, for example, AcMNPV, OpMNPV, BmNPV, HzMNPV, and RoMNPV. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The polynucleotides can be inserted into the vector nucleic acid using techniques known in the art. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

Specific expression vectors are described herein for the purposes of the invention; for example, AcMNPV. Other expression vectors listed herein are not intended to be limiting, and are merely provided by way of example. The person of ordinary skill in the art would be aware of other vectors suitable for maintenance, propagation, or expression of the polynucleotides described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989. Any cell type or expression system can be used for the purposes of the invention including but not limited to, for example, baculovirus systems (O'Riley et al. (1992) *Baculovirus Expression Vectors*, W. H. Freeman and Company, New York 1992) and *Drosophila*-derived systems (Johansen et al. (1989) *Genes Dev* 3(6):882–889).

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the polynucleotide sequences described herein, including both coding and non-coding regions. Expression of this antisense RNA is subject to each of the parameters described above in relation to expression of the sense RNA (regulatory sequences, constitutive or inducible expression, tissue-specific expression).

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Where secretion of the polypeptide is desired, appropriate secretion signals known in the art are incorporated into the vector using techniques known in the art. The signal sequence can be endogenous to the polypeptides or heterologous to these polypeptides.

Where the polypeptide is not secreted into the medium, the desired protein can be isolated from the host cell by techniques known in the art, such as, for example, standard disruption procedures, including freeze thaw, sonication, mechanical disruption, use of lysing agents and the like. The polypeptide can then be recovered and purified by well-known purification methods including, but not limited to, ammonium sulfate precipitation, acid extraction, anion or cationic exchange chromatography, phosphocellulose chromatography, hydrophobic-interaction chromatography, affinity chromatography, hydroxylapatite chromatography, lectin chromatography, and high performance liquid chromatography.

Figure 18A:
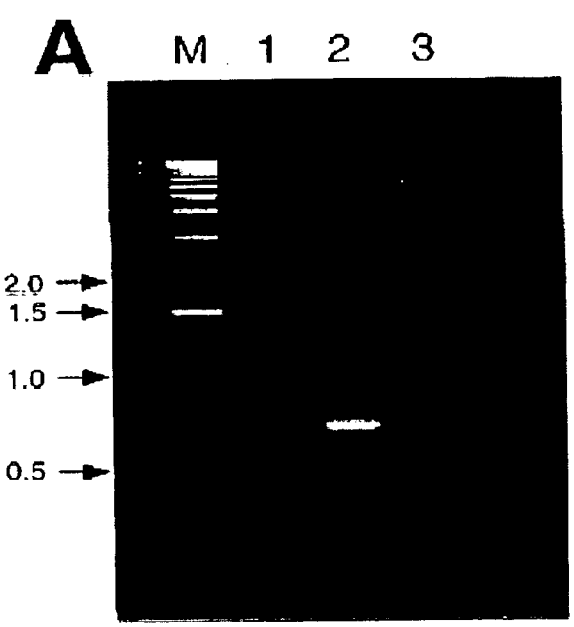
FIG. 18 depicts ethidium bromide-stained agarose gels following electrophoresis of PCR amplification products from Sf9 genomic DNA or High Five™ (Invitrogen Corp., Carlsbad, Calif., USA) cell cDNA templates using degenerate primers corresponding to three different regions conserved within N-acetylglucosaminidases.
Figure 18B:
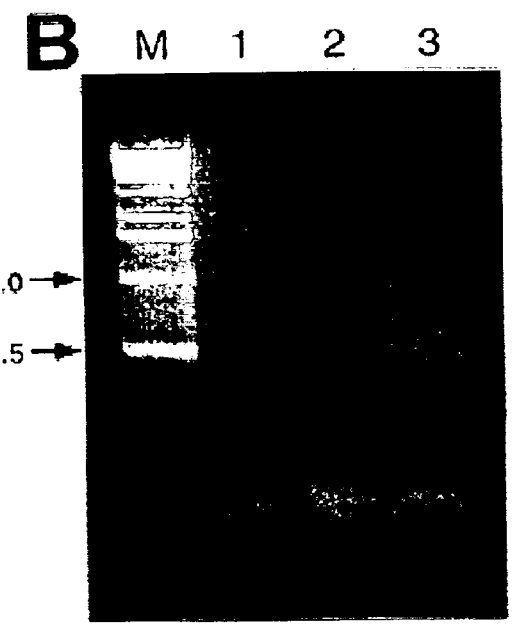

Furthermore, for suppressing activity of endogenous N-acetylglucosaminidase, the invention encompasses utilizing the sequences deduced from the fragment identified in FIG. 18, and described in Example 4. More particularly, in this aspect, the invention comprises utilization of the glucosaminidase nucleotide sequences which are produced by using primers, such as, for example, those primer combinations described in Example 4. These nucleotide sequences may be used in the construction and expression of anti-sense RNA, ribozymes, or homologous recombination (gene "knock-out") constructs, using methods readily available to those skilled in the art, to reduce or eliminate in vivo glucosaminidase activity.

Cell lines produced by the methods of the invention can be tested by expressing a model recombinant glycoprotein in such cell lines and assessing the N-glycans attached therein using techniques described herein or otherwise known in the art. The assessment can be done, for example, by 3-dimensional HPLC techniques. In the Examples of the invention, human transferrin is used as a model target glycoprotein, since this glycoprotein is sialylated in humans and extensive oligosaccharide structural information for the protein is available (Montreuil et al. (1997) *Glycoproteins II* Ed. 203–242). In this manner, cell lines with superior processing characteristics are identified. Such a cell line can then be evaluated for its growth rate, product yields, and capacity to grow in suspension culture (Lindsay et al. (1992) *Biotech. and Bioeng.* 39:614–618, Reuveny et al. (1992) *Ann. NY Acad. Sci.* 665:320, Reuveny et al. (1993) *Appl. Microbiol. Biotechnol.* 38:619–623, Reuveny et al. (1993) *Biotechnol. Bioeng.* 42:235–239).

The invention encompasses expressing heterologous proteins in the cells of the invention and/or according to the methods of the invention for any purpose benefiting from such expression. Such a purpose includes, but is not limited to, increasing the in vivo circulatory half life of a protein; producing a desired quantity of the protein; increasing the biological function of the protein including, but not limited to, enzyme activity, receptor activity, binding capacity, antigenicity, therapeutic property, capacity as a vaccine or a diagnostic tool, and the like. Such proteins may be naturally occurring chemically synthesized or recombinant proteins. Examples of proteins that benefit from the heterologous expression of the invention include, but are not limited to, transferrin, plasminogen, $Na^+$, $K^+$-ATPase, thyrotropin, tissue plasminogen activator, erythropoietin, interleukins, and interferons. Other examples of such proteins include, but are not limited to, those described in International patent application publication number WO 98/06835, the contents of which are herein incorporated by reference.

In one embodiment, proteins that benefit from the heterologous expression of the invention are mammalian proteins. In this aspect, mammals include but are not limited to, cats, dogs, rats, mice, cows, pigs, non-human primates, and humans.

It is recognized that the heterologous expression of the invention not only encompasses proteins that are sialylated in their native source; but also those that are not sialylated as such, and benefit from the expression in the cells of and/or according to the methods of the invention.

It is recognized that proteins that are not sialylated in their native source, can be altered by known genetic engineering methods so that the heterologous expression of the protein according to the invention will result in sialylation of the protein. Such methods include, but are not limited to, the genetic engineering methods described herein. In this aspect, it is further recognized that altering the proteins could encompass engineering into the protein targeting signals to ensure targeting of the proteins to the ER and Golgi apparatus for sialylation, where such signals are needed.

It is also recognized that the cells of the invention contain proteins, which are not sialylated prior to manipulation of the cells according to the methods of the invention, but are sialylated subsequent to the manipulation. In this manner, the invention also encompasses proteins that have amino acid sequences that are endogenous to the cells of the invention, but are sialylated as a result manipulation of the cells according to the methods of the invention.

It is recognized that the analysis of the N-glycans produced according to the methods of the invention may suggest additional strategies to further enhance the sialylation of glycoproteins in insect cells. If the production of Gal containing carbohydrate acceptor structures is low relative to those containing GlcNAc, then the levels of Gal transferase expression are increased by integrating multiple copies of this gene into the insect cell genome or by expressing Gal T under a stronger promoter using techniques described herein or otherwise known in the art. Additionally, or alternatively, substrate feeding strategies are used to enhance the levels of UDP-Gal for this carbohydrate processing reaction. In contrast, if the fraction of carbohydrate structures terminating in Gal is high and the fraction with terminal SA is low, then sialyltransferase or CMP-SA production is enhanced. Examination of sialyltransferase activity using techniques described herein or otherwise known in the art, such as, for example, FRET or HPLC and CMP-SA levels using HPAEC, is used to determine which step is the metabolic limiting step to sialylation. These metabolic limitations are overcome by increasing expression of specific enzymes or by altering substrate feeding strategies or a combination thereof.

Assays

Having generally described the invention, the same will be more readily understood by reference to the following assays and examples, which are provided by way of illustration and are not intended as limiting.

Analytical bioassays are implemented to evaluate enzymatic activities in the N-glycosylation pathway of insect cells. In order to screen a larger selection of insect cells for particular oligosaccharide processing enzymes, bioassays in which multiple samples can be analyzed simultaneously are advantageous. Consequently, bioassays based on fluorescence energy transfer (FRET) and time-resolved fluorometry of europium (Eu) are designed to screen native and recombinant insect cell lines for carbohydrate processing enzymes in a format that can handle multiple samples.

Fluorescence assays are especially useful in detecting limiting steps in carbohydrate processing due to their sensitivity and specificity. FRET and Eu assays detect enzymatic activities at levels as low as $10^{-14}$ M, which is greater than the sensitivity obtained with $^{125}I$. In addition, the use of substrates modified with fluorophores enables the measurement of one specific enzyme activity in an insect cell lysate, and multiple samples can be analyzed simultaneously in a microtiter plate configuration used in an appropriate fluorometer. With these assays, insect cell lines are rapidly screened for the presence of processing enzymes including Gal, GlcNAc, and sialic acid transferases to identify limiting enzymes in N-glycosylation in native and recombinant cells.

Fluorescence Energy Transfer (FRET) Assays

Glycosyl transferase activity assays are based on the principle of fluorescence energy transfer (FRET), which has been used to study glycopeptide conformation (Rice et al.

(1991) *Biochemistry* 30:6646–6655) and to develop endotype glycosidase assays (Lee et al. (1995) *Anal. Biochem.* 230:31–36).

Gal T Assay

Figure 12:
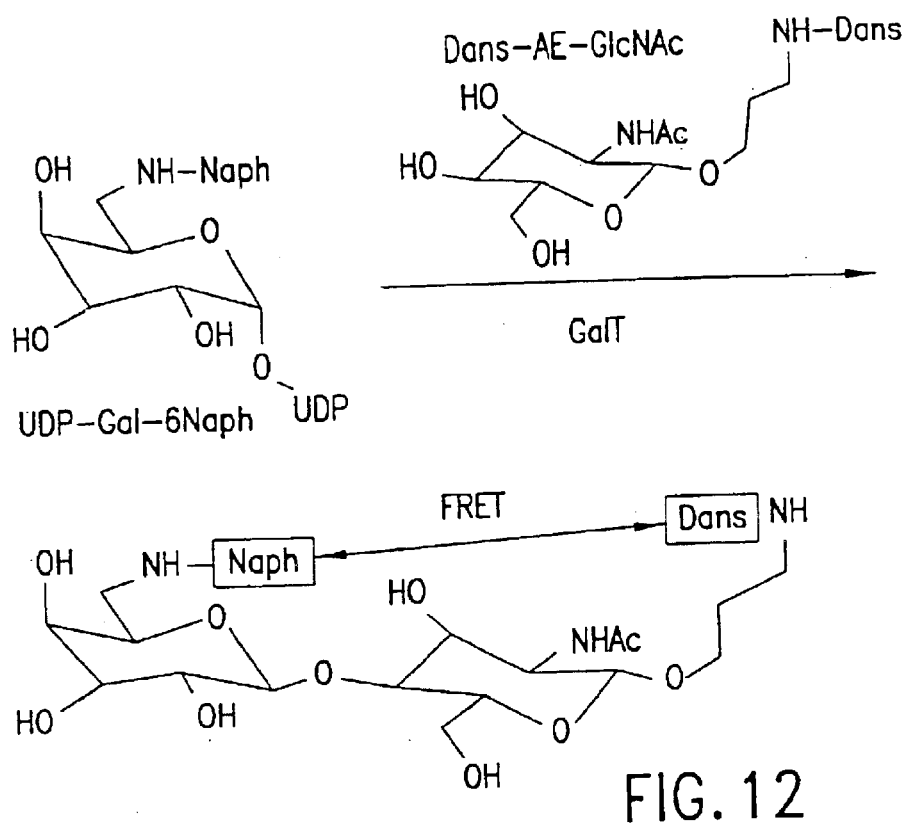
FIG. 12 depicts the product of reacting UDP-Gal-6-Naph with Dans-AE-GlcNAc in the presence of GalT.
Figure 13:
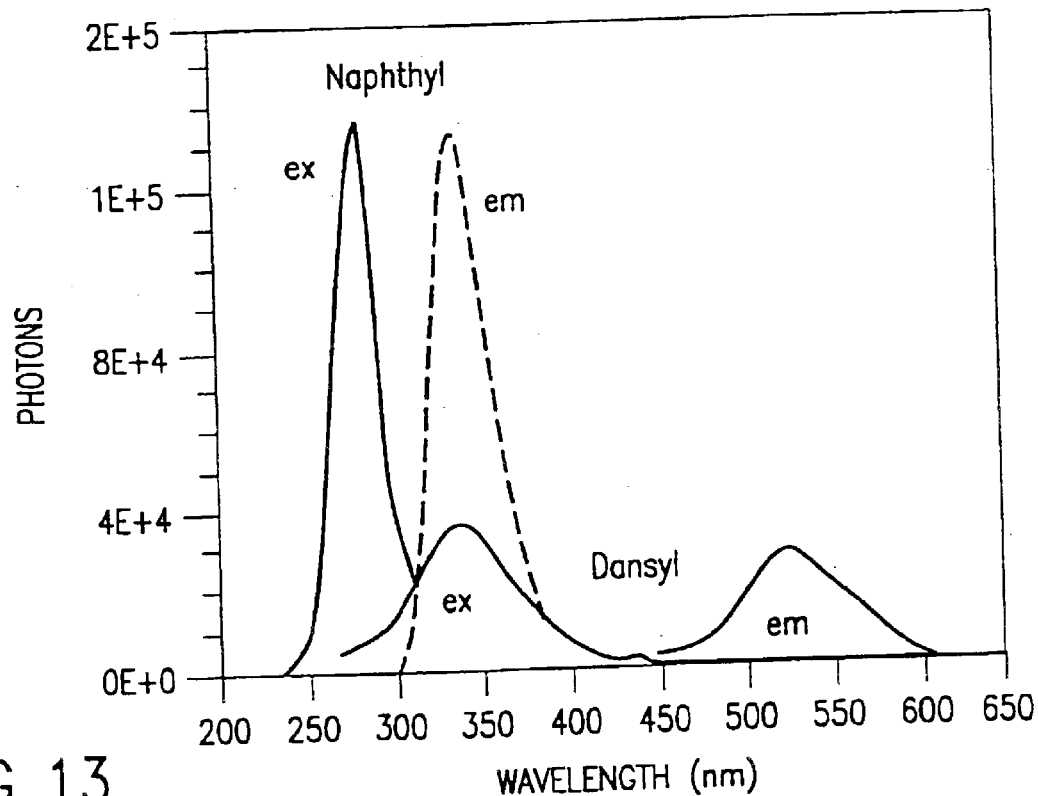
FIG. 13 depicts the distinguishing emission spectra of GalT assay reactants and products, as described in the "Experimental" section below. Irradiation of the naphthyl group in UDP-Gal-6-Naph at 260–290 nm ("ex") results in an emission peak at 320–370 nm ("em" dotted line) while irradiation of the Galactose-transferase reaction products at these same low wavelengths results in energy transfer to the dansyl group and an emission peak at 500–560 nm ("em" solid line).

The fluorescent compound, UDP-Gal-6-Naph, synthesized by consecutive reactions of galactose oxidase (generating 6-oxo compound) and reductive amination with naphthylamine, is found to be effective as a substrate for Gal transferase. When UDP-Gal-6-Naph is reacted with an acceptor carrying a dansyl group (Dans-AE-GlcNAc) in the presence of Gal-T, a product is created that can transfer energy (FIG. 12). While irradiation of the naphthyl group in UDP-Gal-6-Naph at 260–290 nm ("ex" in FIG. 13) results in the usual emission at 320–370 nm ("em" dotted line in FIG. 13), irradiation of the product at these same low wavelengths results in energy transfer to the dansyl group and emission at 500–560 nm ("em" solid line in FIG. 13). Assay sensitivity is as great as the fluorometer allows (pico- to femtomol range) and exceeds that of radioisotopes. In addition, multiple samples can be monitored simultaneously in the fluorometer, allowing a number of cell lines to be evaluated rapidly for Gal T activity.

Sialyltransferase Assay

Figure 14:
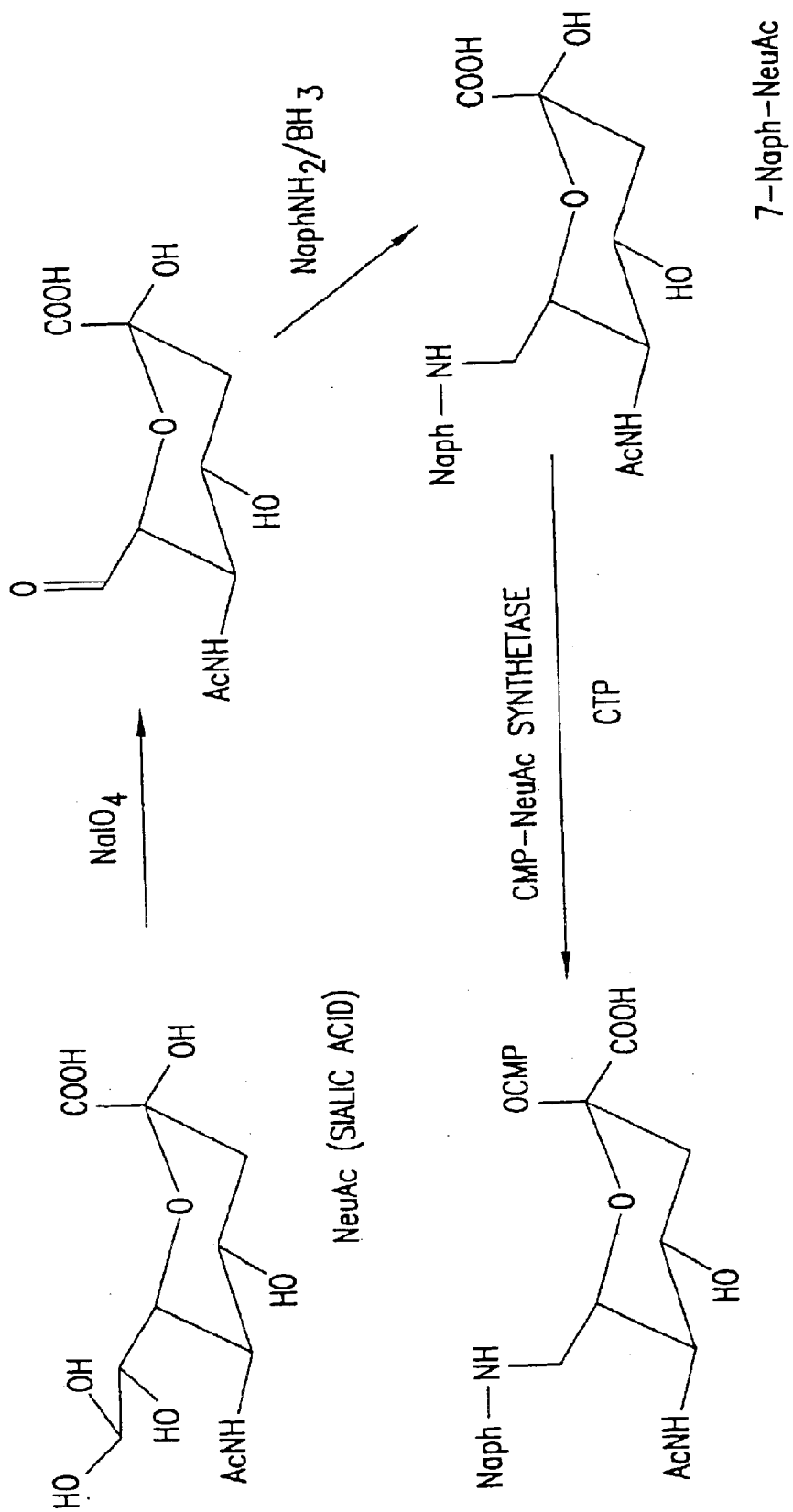
FIG. 14 depicts the oxidation reaction of sialic acid.

A sialyltransferase assay is designed using similar FRET technology described in the above example for Gal T. The 3-carbon tail (exocyclic chain) of sialic acid (in particular, its glycoside) can be readily oxidized with mild periodate to yield an aldehyde (FIG. 14). This intermediate is reductively aminated to generate a fluorescently tagged sialic acid (after removal of its aglycon), which is then modified to form a fluorescently modified CMP-sialic acid (See also Lee et al. (1994) *Anal. Biochem.* 216:358–364, Brossamer et al. (1994) *Methods Enzymol.* 247:153–177). The acceptor substrate is modified as described above to include the dansyl group. Then the FRET approach is used to measure either alpha(2,3) or alpha(2,6) sialyltransferase activity since these enzymes should utilize the modified CMP-SA as donor substrate to generate a product with altered fluorescent emission characteristics.

The choice of the fluorescent donor and acceptor pair can be flexible. The above examples are given using naphthyl-dansyl pairs, but other fluorescent combinations may be even more sensitive (Wu et al. (1994) *Anal. Biochem.* 250:260–262).

Europium ($Eu^{+}$) Fluorescence Assays

An example of the use of $Eu^{+3}$ fluorescence for the evaluation of Gal T activity is provided herein in the N-linked oligosaccharides from insect cells. The same techniques are used to develop enzymatic assay for transferases such as GlcNAc T1 and glycosidases such as N-acetylglucosaminidase. Further enhancements in sensitivity are obtained with the advent of the super-sensitive Eu-chelator, BHHT (4,4'-bis(1", 1", I", 2",2",3",3'-heptatluro-4",6"-hexanedione-6'-yl)-chlorosulfo-o--terphenyl) (Yuan et al. (1998) *Anal. Chem.* 70:596–601), which allows detection down to the lower fmol range.

GlcNac-TI Assay

Figure 15:
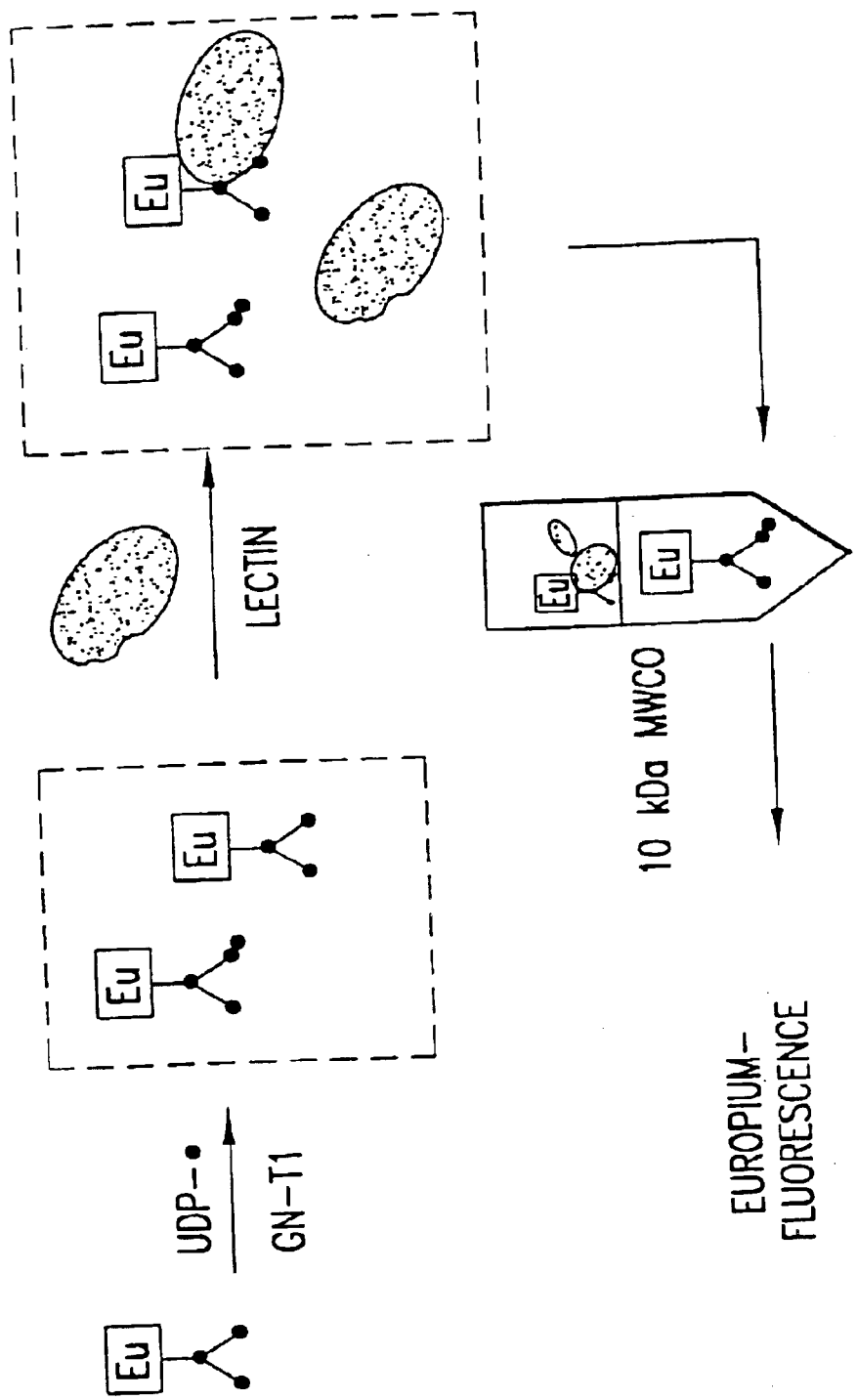
FIG. 15 schematically depicts a new GlcNAc T1 assay utilizing a synthetic 6-aminohexyl glycoside of the trimannosyl N-glycan core structure labeled with DTPA (Diethylenetriaminepentaacetic acid) and complexed with $Eu^{+3}$ (see "Experimental" section below). This substrate is incubated with insect cell lysates or positive controls containing GlcNAc T1 and UDP-GlcNAc. Chemical inhibitors are added to minimize background N-acetylglucosaminidase activity. After the reaction, an excess of Crocus lectin CVL (Misaki et al. (1997) *J. Biol. Chem.* 272:25455–25461), which specifically binds the trimannosyl core, is added. The amount of lectin required to bind all the trimannosyl glycoside (and hence all the $Eu^{+3}$ label) in the absence of any GlcNAc binding is predetermined. Following an ultrafiltration step, the glycoside modified with GlcNAc (not binding CVL) appears in the filtrate. Measurement of the $Eu^{+3}$ fluorescence in the filtrate reflects the level of GlcNAc T1 activity in the culture lysates.

A new GlcNAc-TI assay, illustrated in FIG. 15, utilizes a synthetic 6-aminohexyl glycoside of the trimannosyl N-glycan core structure labeled with DTPA (Diethylenetriaminepentaacetic acid) and complexed with $Eu^{+3}$. This substrate is then incubated with insect cell lysates or positive controls containing GlcNAc T1 and UDP-GlcNAc. Addition of chemical inhibitors are used to minimize background N-acetylglucosaminidase activity. After the reaction, an excess of Crocus lectin CVL (Misaki et al. (1997) *J. Biol. Chem.* 272:25455–25461), which specifically binds the trimannosyl core, is added. The amount of the lectin required to bind all the trimannosyl glycoside (and hence all the $Eu^{+3}$ label) in the absence of any GlcNAc binding is predetermined. The reacted mixture is then filtered through a 10,000 molecular weight cut off (MWCO) microfuge ultrafiltration cup. The glycoside modified with GlcNAc does not bind CVL and appears in the filtrate. Measurement of the $Eu^{+3}$ fluorescence in the filtrate reflects the level of GlcNAc T1 activity in the culture lysates.

N-Acetylglucosaminidase Assay

An assay for N-acetylglucosaminidase activity is developed using a different lectin, GS-II, which is specific for GlcNAc. The substrate is prepared by modification of the same trimannosyl core glycoside described above using in vitro purified GlcNAc T1, which results in addition of a GlcNAc_beta(1-2) residue to the Man_alpha(1-3) residue. Following incubation with insect cell lysates, enzymatic hydrolysis by N-acetylglucosaminidase removes GlcNAc from the substrate resulting in the tri-mannosyl core product. The product is not susceptible to lectin binding and thus escapes into the filtrate. Evaluation of $Eu^{+3}$ fluorescence in the filtrate provides a measure of the N-acetylglucosaminidase activity. Alternatively, enhanced binding of the Eu-bound trimannosyl core to the *Crocus* lectin described above can be used as another assay for N-acetylglucosaminidase activity.

Characterization of N-Linked Oligosaccharides from Insect Cells

Carbohydrate structure elucidation of the N-glycans of a recombinant glycoprotein, IgG, purified from *Trichoplusia ni* (High Five™ cells; Invitrogen Corp., Carlsbad, Calif., USA) has been undertaken (Davis et al. (1993) *In Vitro Cell. Dev. Biol.* 29:842–846; Hsu et al. (1997) *J. Biol. Chem.* 272:9062–9070). The recombinant glycoprotein, immunoglobulin G (IgG), was purified from both intracellular and extracellular (secreted) sources and all the attached N-glycans determined using three dimensional HPLC techniques. The composition of these structures provided insights into the carbohydrate processing pathways present in insect cells and allowed a comparison of intracellular and secreted N-glycan structures.

The *Trichoplusia ni* cells grown in serum free medium in suspension culture were infected with a baculovirus vector encoding a murine IgG (Summers et al. (1987) *A manual of methods for baculovirus vectors and insect cells culture procedures*). IgG includes an N-linked oligosaccharide attachment on each of the two heavy chains.

Heterologous IgG was purified from the culture supernatant and soluble cell lysates using a Protein A-Sepharose column. N-linked oligosaccharides were isolated following protease digestion of IgG and treatment with glycoamidase A to release the N-glycans. Oligosaccharides were then derivatized with 2-aminopyridine (PA) at the reducing ends to provide fluorogenic properties for detection.

Three-dimensional HPLC analysis, was performed to elucidate the N-linked oligosaccharide structures attached to the heavy chain of IgG (Tomiya et al. (1988) *Anal. Biochem.* 171:73–90, Takahashi et al. (1992) *Handbook of Endoglycosidases and Glycoamidases Ed.* 199–332). This technique separates oligosaccharides by three successive HPLC steps and enables the identification of structures by comparison of elution conditions with those of known standards.

A DEAE column was used to separate oligosaccharides on the basis of carbohydrate acidity (first dimension). None of the oligosaccharides retained on this column were found to include sialic acid. Treatment of the acidic fractions with neuraminidase from *Arthrobacter ureafaciens* (known to cleave all known sialic acid linkages) failed to release any sialic acid, and ODS-chromatography of the fractions revealed several minor components different from all known sialylated oligosaccharides.

Figure 6:
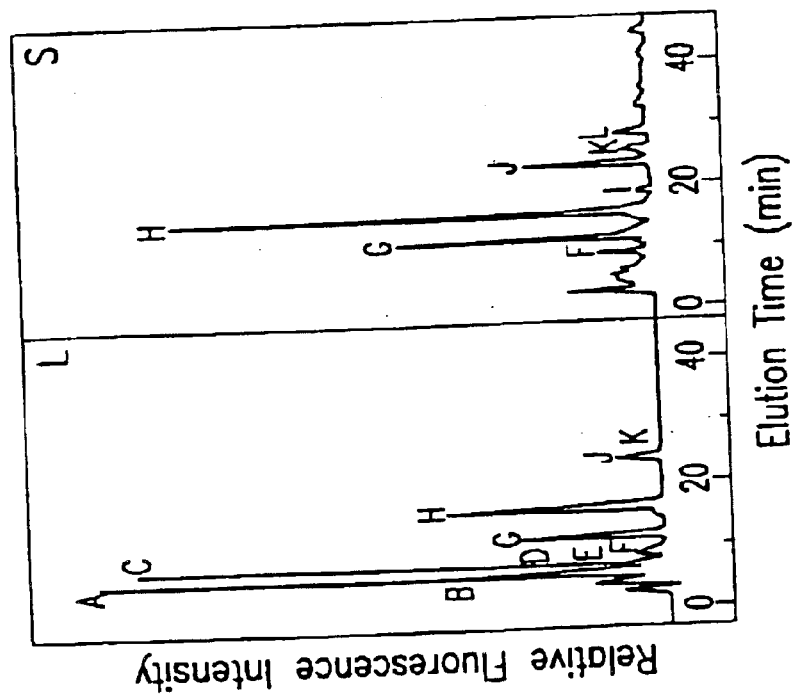
FIG. 6 depicts a chromatogram of labeled oligosaccharides separated by reverse phase High Performance Liquid Chromatography (HPLC) on an ODS-silica column. Using this technique, oligosaccharides are fractionated according to their carbohydrate structures. Panel "L" represents cell lysate fractions and panel "S" represents cell supernatant fractions.

The second dimension used reverse phase HPLC with an ODS-silica column to fractionate the labeled oligosaccharides according to carbohydrate structure. Supernatant (S) and lysate (L) IgGs oligosaccharides were separated into 6 and 10 fractions, respectively, labeled A–L in FIG. 6.

Separation in the third and final dimension was accomplished using an amide column to isolate oligosaccharides on the basis of molecular size. Peak B from the ODS column was separated into two separate oligosaccharide fractions, and peak H was separated into three separate oligosaccharide fractions on the amide-column.

After oligosaccharide purification, structures of unknown oligosaccharides were determined by comparing their positions on the 3-dimensional map with the positions of over 450 known oligosaccharides. Co-elution of an unknown sample with a known PA-oligosaccharide on the ODS and amide-silica columns was used to confirm the identity of an oligosaccharide. Digestion by glycosidases with specific cleavage sites (alpha-L-fucosidase, beta-galactosidase, beta-N-acetylglucosaminidase, and alpha-mannosidase) followed by reseparation provided further confirmation.

Figure 7:
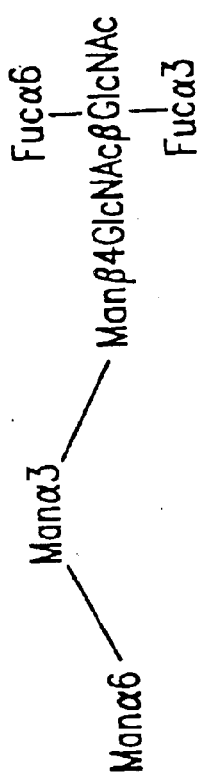
FIG. 7 depicts the structure of Oligosaccharide G.

All the oligosaccharides in the culture medium and cell lysates matched known carbohydrates except for oligosaccharide G. The structure of oligosaccharide G was elucidated by treatment of the N-glycan with alpha-L-fucosidase, known to digest Fuc_alpha1-6GlcNAc, followed by treatment with 13.5 M trifluoroacetic acid to remove the alpha1,3 linked fucose. The de-alpha1,6- and de-alpha1,3-fucosylated oligosaccharide G co-eluted with a known oligosaccharide, allowing the identification of G. The structure of oligosaccharide G is shown in FIG. 7.

The structure of oligosaccharide G was further confirmed by $^1$H-NMR and electrospray ionization (ESI) mass spectrometry (Hsu et al. (1997) *J. Biol. Chem.* 272:9062–9070). Thus, the combination of these techniques can be used to elucidate both known and unknown oligosaccharides.

Figure 8:
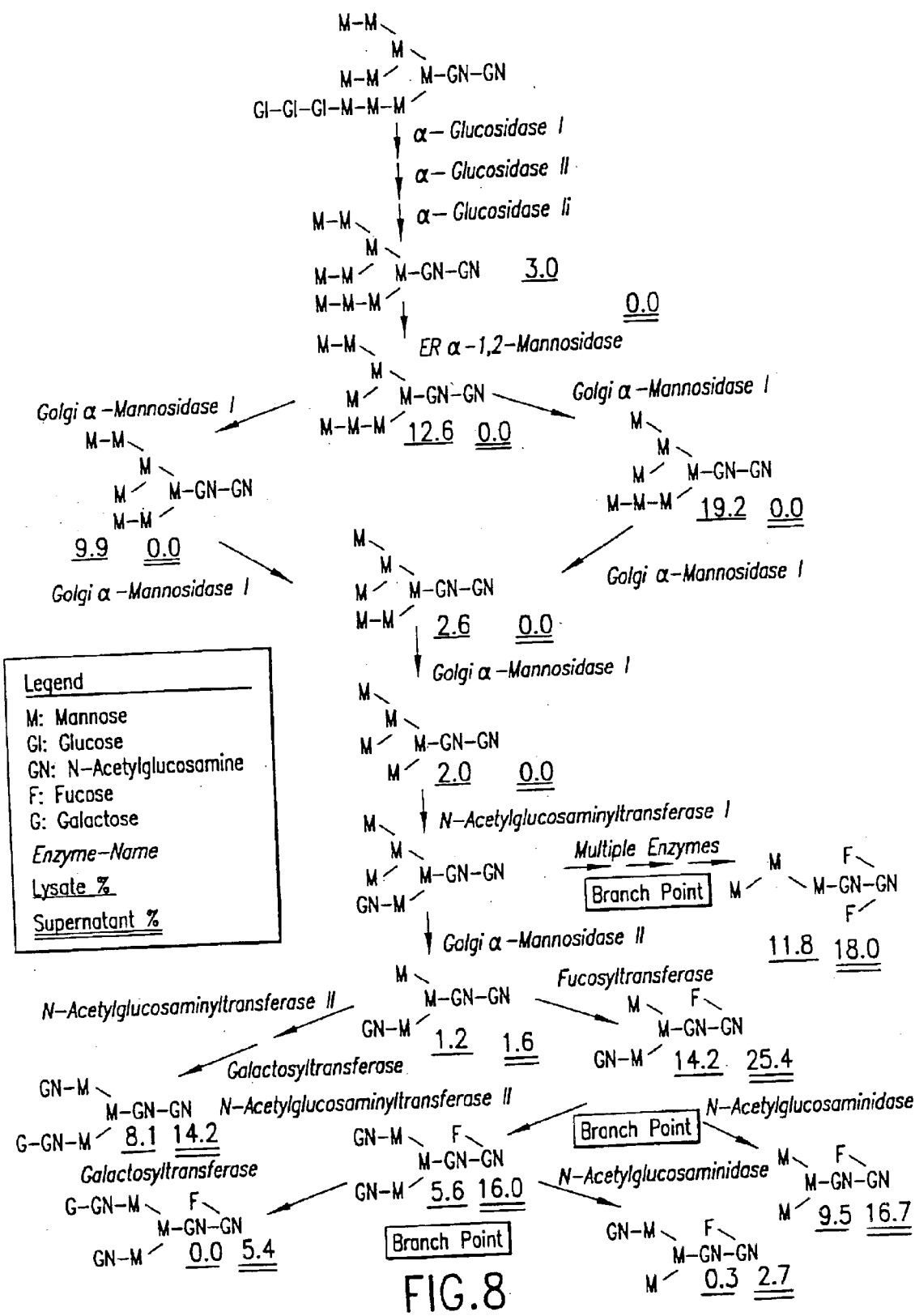
FIG. 8 depicts the glycosylation pathway in *Trichoplusia ni* insect cells (High Five™ cells; Invitrogen Corp., Carlsbad, Calif., USA).

The carbohydrates attached to IgG from the culture medium and intracellular lysate were identified and the levels present in each source were quantified. These structures were then used in conjunction with previous studies of oligosaccharide processing in insect cells (Altmann et al. (1996) *Trends in Glycoscience and Glycotechnology* 8:101–114) to generate a detailed map of N-linked oligosaccharide processing in *Trichoplitsia ni* insect cells. The pathway and the levels of the oligosaccharides from secreted and intracellular sources are detailed in FIG. 8.

The initial processing in the *T. ni* cells appears to be similar to the mammalian pathway, including trimming of the terminal glucose and mannose residues. The trimming process follows a linear pathway with the exception of two different forms of the Man$_7$GlcNAc$_2$ (M7GN, in FIG. 8 also observed in native insect glycoproteins (Altmann et al. (1996) *Trends in Glycoscience and Glycotechnology* 8:101–114) and IgG$_4$, from NS/0 cells (Ip et al. (1994) *Arch. Biochem. Biophys.* 308:387–399). The presence of these two Man$_7$ forms suggests the possible existence of an alternative processing pathway that yields Man$_7$GlcNAc$_2$ through the action of endo-alpha-mannosidase. Following cleavage of the mannose residues, GlcNAc (GN) is added to the alpha1,3 branch of Man$_5$GlcNAC$_2$ by GlcNAc TI (N-acetylglusosaminyltransferase I) (Altmann et al. (1996) *Trends in Glycoscience and Glycotechnology* 8:101–114). However, GlcNAc$_1$ Man$_5$GlcNAC$_2$ must be a short-lived intermediate quickly processed by alpha-Man II, since this structure was not detected in the *T. ni* cell lysate. At the GlcNAc$_1$, Man$_3$ GlcNAc$_2$ oligosaccharide, several branching steps in the N-glycan processing pathway are possible in insect cells. Complex glycoforms can be generated by the action of GlcNAc TII (N-acetylglucosaminyltransferase II) and Gal T (galactosyltransferase T) to provide oligosaccharides which include terminal GlcNAc (GN) and Gal (G) residues. None of the complex oligosaccharide structures included sialic acid indicating that sialylation is negligible or non-existent in these cells.

The production of these complex glycoforms must compete with an alternative processing pathway that is catalyzed by N-acetylglucosaminidase (Altmann et al. (1995) *J. Biol. Chem.* 270:17344–17349) (see Branch Points in FIG. 8), leading to the production of hybrid and paucimannosidic structures. While the complex-type N-glycans represent 35% of the total secreted glycoforms (supernatant % in FIG. 8), the majority of secreted N-glycans are either paucimannosidic (35%) or hybrid structures (30%). Furthermore, those complex structures with a branch terminating in Gal represent less than 20% of the total secreted glycoforms and no structures were observed with terminal Gal on both branches of the N-glycan.

In contrast to the secreted glycoforms, the intracellular N-glycans (lysate % in FIG. 8) obtained from insect cells include more than 50% high-mannose type structures. The fraction of intracellular complex oligosaccharides is less than 15% and only 8% include a terminal Gal residue. The high level of high-mannose structures from intracellular sources indicates significantly less oligosaccharide processing for most of the intracellular immunoglobulins. Many of these intracellular immunoglobulins may not reach the compartments in which carbohydrate trimming takes place (Jarvis et al. (1989) *Mol. Cell. Biol.* 9:214–223). High mannose glycoforms are also observed intracellularly for mammalian cells (Jenkins et al. (1998) *Cell Culture Engineering VI*).

EXAMPLES

Example 1

Evaluation of N-glycosylation Pathway Enzymes

The levels of N-linked oligosaccharide processing enzymes are measured using analytical assays to characterize carbohydrate processing in native and recombinant insect cells. These assays are used to compare the N-glycan processing capacity of different cell lines and to evaluate changes in processing and metabolite levels following metabolic engineering modifications.

Figure 9:
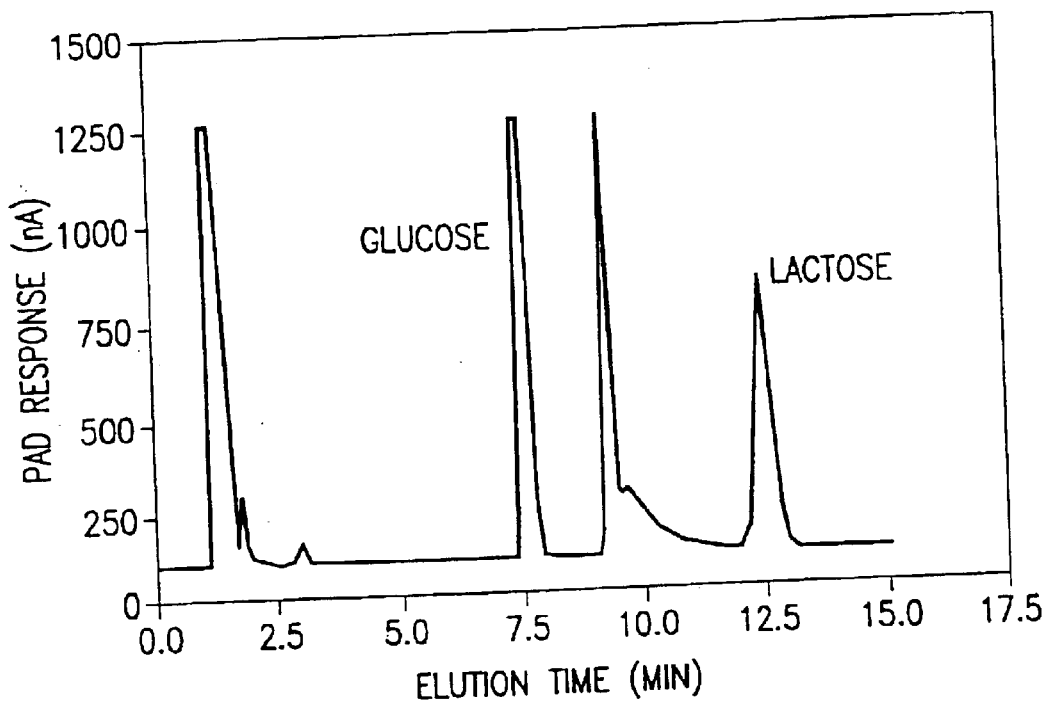
FIG. 9 depicts the chromatogram of a Galactose-transferase assay following High Performance Anion Exchange Chromatography (HPAEC), as described in the Examples and references cited therein.

High Performance Anion Exchange Chromatography (HPAEC) Assay for Galactose Transferase HPAEC is used in combination with pulsed amperometric detection (HPAEC-PAD) or conductivity to detect metabolite levels in the CMP-SA pathway and to evaluate N-linked oligosaccharide processing enzymes essentially as described by (Lee et al. (1990) *Anal. Biochem.* 34:953–957, Lee et al. (1996) *J. Chromatography A* 720:137–149). Shown in FIG. 9 is an example of the use of HPAEC-PAD for measuring Gal T activity by following the lactose formation reaction:

UDP–Gal+Glc GalT Lac+UDP

The peak labeled "Lac" indicates the formation of the product lactose (Lac). Many of the enzymes involved in N-glycosylation (e.g., aldolase, CMP-NeuAc synthetase, sialyltransferase) and metabolic intermediates (e.g., sialic acid, CMP-sialic acid, ManNAc, ManNAc-6-phosphate) in the CMP-SA production pathway are measured using this form of chromatography, essentially as described by Lee et al. (1990) *Anal. Biochem.* 34:953–957, Lee et al. (1996) *J. Chromatography A* 720:137–149, Hardy et al. (1988) *Anal. Biochem.* 170:54–62, Townsend et al. (1988) *Anal. Biochem.* 174:459–470, Kiang et al. (1997) *Anal. Biochem.* 245:97–101.

Figure 10:
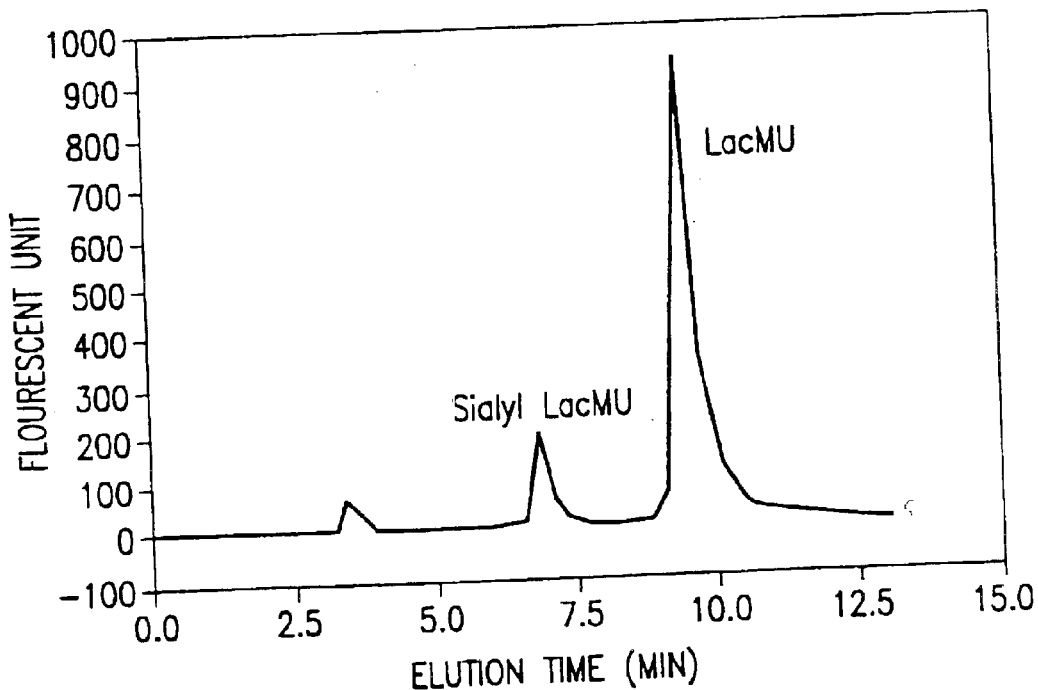
FIG. 10 depicts the chromatogram of a 2,3-Sialyltransferase assay following Reverse Phase-High Performance Liquid Chromatography (RP-HPLC), as described in the Examples.

Reverse Phase High Performance Liquid Chromatography (HPLC) for Sialyltransferase To detect native sialyltransferase enzyme activity, *Trichoplusia ni* lysates were incubated in the presence of exogenously added CMP-SA and the fluorescent substrate, 4-methylumbelliferyl lactoside (Lac-MU). Negligible conversion of the substrate was observed, indicating the absence of endogenous sialyltransferase activity. However, following infection of the insect cells with a baculovirus encoding human alpha2-3-sialyltransferase, conversion of Lac-MU to the product sialyl LacMU was observed in cell lysates using Reverse Phase HPLC and a fluorescence detector (FIG. 10). For higher sensitivity, Lac-PA (PA=2-aminopyridine) or Lac-ABA(ABA=o-aminobenzamide) are used as substrates. HPLC and HPAEC is used in conjunction with other fluorometric methods detailed in the procedures to analyze the metabolites and enzymatic activities in insect cells.

Dissociation Enhanced Lanthananide FluorommunoAssay (DELFIA) for GalT

Figure 11:
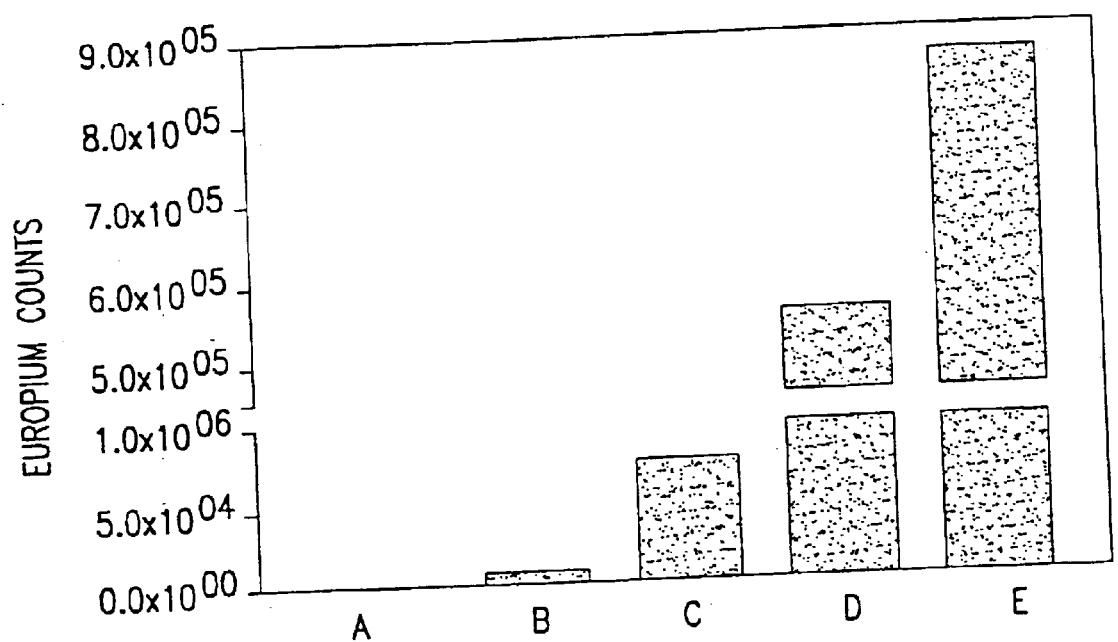
FIG. 11 depicts the results of a Galactose-transferase (Gal-T) assay of insect cell lysates performed using a Europium ($Eu^{+3}$)-labeled *Ricinus cummunis* lectin (RCA 120) probe; which specifically binds Gal or GalNAc oligosaccharide structures as described in the Examples. Each column represents the Gal-T activity in a given sample; Column (A) represents boiled *T. ni* cell lysates, Column (B) represents normal *T. ni* cell lysates, Column (C) represents activity in 0.5 mU of enzyme standard, Column (D) represents lysate from *T. ni* cells infected with a baculovirus coding for GalT, Column (E) represents lysates from Sf-9 cells stably transfected with the GalT gene.

The previous chromatography techniques have one limitation in that only one sample can be handled at a time. When samples from several cell lines must be assayed, a method such as DELFIA is advantageous since a multiwell fluorometer can simultaneously examine activities in many samples on a microtiter plate (Hemmila et al. (1984) *Anal. Biochem.* 137:335–343). The application of such a technique for the measurement of Gal T activity in several different insect cell lysates and controls is shown in FIG. 11. First, the wells of the microtiter plate are coated with the substrate GlcNAc-BSA (Stowell et al. (1993) *Meth. in Carb. Chem.* 9:178–181). After incubation with Gal T and UDP-Gal, the well is washed and the Gal residue newly attached to GlcNAc-BSA is measured with europium ($Eu^{+3}$)-labeled *Ricinus cummunis* lectin, which specifically binds Gal or GalNAc structures. The sensitivity of Eu fluorescence under appropriate conditions can reach the fmol range and match or eclipse that of radioiodides (Kawasaki et al. (1997) *Anal. Biochem.* 250:260–262).

FIG. 11 depicts GlcNAc-BSA in (A) Boiled lysate; (B) *T. ni*; (C) Standard enzyme, 0.5 mU; 0)) *T. ni* insect cells infected with a baculovirus coding for GalT (E) Sf-9 cells stably transfected with GalT gene. The increase in Gal T activity in untreated cell lysates (B in FIG. 11) relative to boiled lysates (A) indicates that *T. ni* cells have low but measurable endogenous Gal T activity. The Gal T activity level is increased significantly following infection with a baculovirus vector including a mammalian Gal T gene under the IE1 promoter or by using Sf-9 cells stably-transformed with the Gal T gene (cell lines are described in Jarvis et al. (1996) *Nature Biotech.* 14:1288–1292; and Hollister et al. (1998) *Glycobiology* 8:473–480).

The DELFIA method is not limited to Gal T measurement. This technique is used to evaluate the activity of any processing enzyme which generates carbohydrate structures containing binding sites for a specific lectin or carbohydrate-specific antibodies (Taki et al. (1994) *Anal. Biochem.* 219:104–108, Rabina et al. (1997) *Anal. Biochem.* 246:459–470).

Example 2

Enhancing SA Levels by Substrate Addition

Because the conventional substrates in insect cell media are not efficiently converted to CMP-SA in insect cells as demonstrated by the low levels of CMP-SA, alternative substrates are added to the culture medium. Because sialic acid and CMP-SA are not permeable to cell membranes (Bennetts et al. (1981) *J. Cell. Biol.* 88:1–15), they are not considered as appropriate substrates. However, other precursors in the CMP-SA pathway are incorporated into cells and considered as substrates for the generation of CMP-SA in insect cells.

Incorporation and Conversion of N-Acetylmannosamine (ManNAc)

ManNAc has been added to mammalian tissue and cell cultures and enzymatically converted to SA and CMP-SA (Ferwerda et al. (1983) *Biochem. J.* 216:87–92, Gu et al. (1997) *Improvement of the interferon-gamma sialylation in Chinese hamster ovary cell culture by feeding N-acetylmannosamine,* Thomas et al. (1985) *Biochim. Biophys. Acta* 846:37–43). Consequently, external feeding of ManNAc is examined as one strategy to enhance CMP-SA levels in insect cells. ManNAc is available commercially (Sigma Chemical Co.) or can be prepared chemically from the less expensive feedstock GlcNAc in vitro using sodium hydroxide (Mahmoudian et al. (1997) *Enzyme and Microbial Technology* 20:393–400). Initially, the levels of native cellular ManNAc, if any, is determined using HPAEC-PAD techniques (Lee et al. (1990) *Anal. Biochem.* 34:953–957, Lee et al. (1996) *J. Chromatography A* 720:137–149, Hardy et al. (1988) *Anal. Biochem.* 170:54–62, Townsend et al. (1988) *Anal. Biochem.* 174:459–470, Kiang et al. (1997) *Anal. Biochem.* 245:97–101). The ability to increase intracellular ManNAc levels is evaluated by adding ManNAc to cell culture media. Incorporation of exogenous ManNAc is quantified using unlabeled ManNAc if levels of native ManNAc are negligible, or $^{14}C$- or $^3H$-labeled ManNAc if significant levels of native ManNAc are present) (Bennetts et al. (1981) *J. Cell. Biol.* 88:1–15, Kriesel et al. (1988) *J. Biol. Chem.* 263:11736–11742). The levels of radioactive ManNAc and other metabolites are determined by collecting ManNAc peaks following HPAEC and measuring the radioactivity using scintillation countering.

To be effective as a substrate for sialylation, the ManNAc must be converted to SA and CMP-SA through intracellular pathways. This conversion is detected directly from externally added ManNAc by following an increase in internal SA and CMP-SA levels using HPAEC or thin layer chromatography (TLC) combined with liquid scintillation counting to detect the radiolabeled metabolites. HPAEC techniques have been used to quantify cellular pools of CMP-SA in as few as $6 \times 10^6$ mammalian cells (Fritsch et al. (1996) *Journal of Chromatography A* 727:223–230), and TLC has been used to evaluate conversion of $^{14}C$ labeled ManNAc to sialic acid in bacteria (Vann et al. (1997) *Glycobiology* 7:697–701). If the addition of ManNAc leads to a significant increase in the CMP-SA levels, a limiting step exists in the production of ManNAc from conventional insect cell media substrates. Different ManNAc feeding concentrations are tested and the effect on CMP-SA levels and insect cell viability evaluated to determine if there are any deleterious effects from feeding the ManNAc as substrate. Conversion of ManNAc to SA through the aldolase pathway requires pyruvate, and the addition of cytidine can enhance CMP-SA production from SA (Thomas et al. (1985) *Biochim. Biophys. Acta* 846:37–43). Thus, pyruvate and cytidine are optionally added to the medium to enhance conversion of ManNAc to CMP-SA (Tomita et al. (1995) *Biochim. Biophys. Acta* 1243:329–335, Thomas et al. (1985) *Biochim. Biophys. Acta* 846:37–43).

Alternative Substrates

Other precursors substrates such as N-acetylglucosamine (GlcNAc) and glucosamine are converted to SA and CMP-SA through the ManNAc pathway in eukaryotic cells (Pederson et al. (1992) *Cancer Res.* 52:3782–3786, Kohn et al. (1962) *J. Biol. Chem.* 237:304–308). The disposition of these alternative precursor substrates are monitored using HPAEC analysis using techniques known in the art and compared with ManNAc feeding strategies to determine which substrate provides for the most efficient production of CMP-SA, in particular insect cells.

Example 3

Purification and Cloning of CMP-SA Synthetase

A bioinformatics search of the cDNA libraries of HGS revealed a novel human CMP-sialic acid synthetase (CMP-SA synthetase, or CMP-SA) gene based on its homology with the *E. coli* DNA sequence. The bacterial enzyme includes a nucleotide binding site for CTP. This binding site contains a number of amino acids that are conserved among all known bacterial CMP-SAS enzymes (See Stoughton et al., *Biochem J* 15:397–402 (1999). The identity of the human cDNA as a CMP-SA synthetase gene was confirmed by the presence of significant homology within the binding motif:

```
                                         (SEQ ID NO: 17)
bacterial sequence: IIAIIPARSGSKGL (SEQ ID NO: 18)
identity/homology +
           A+I AR GSKG+human cDNA LAALILARGGSKGI
``` in isolating alpha-mannosidase cDNAs from Sf-9 cells (Jarvis et al. (1997) *Glycobiology* 7:113–127, Kawar et al. (1997) *Glycobiology* 7:433–443). Degenerate oligonucleotide primers are designed corresponding to regions of conserved amino acid sequence identified in all N-acetylglucosaminidases described thus far, from human to bacteria, including two lepidopteran insect enzymes (Zen et al. (1996) *Insect Biochem. Mol. Biol.* 26:435–444). These primers are used to amplify a fragment of the N-acetylglucosaminidase gene(s) from genomic DNA or cDNA of lepidopteran insect cell lines commercially, publicly, or otherwise available for the purposes of this invention. A putative N-acetylglucosaminidase gene fragment from Sf9 genomic DNA and from High Five™ cell (Invitrogen Corp., Carlsbad, Calif., USA) cDNA has been identified (FIG. 18). Similar techniques are used to isolate cDNAs from other insect cell lines of interest. The identification of cDNAs for the Sf9 or High Five™ N-acetylglucosaminidase facilitates the isolation of the gene in other insect cell lines.

FIG. 18 depicts PCR amplification of Sf9 genomic DNA (A) or High Five™cell cDNA (B) with degenerate primers corresponding to three different regions conserved within N-acetylglucosaminidases. These regions were designated 1, 2, and 3, from 5 to 3'. Lane 1 (sense primer 1 and antisense primer 2); Lanes 2 (sense primer 1 and antisense primer 3); Lanes 3 (sense primer 2 and antisense primer 3). M (size standards with sizes indicated in Kbp). The results show that specific fragments of N-acetylglucosaminidase genes were amplified from both DNAs (lanes A2 and B3). The specificity of the reactions is indicated by the fact that different primer pairs produced different amplification products from different templates. The primer sequences utilized in amplifying the putative N-acetylglucosaminidase gene were as follows:

```
Sense primer #1:     5'-T/C,T,I,C,A,C/T,T,G,G,C,A,C/T,A/T/C,T,I,G,T,I,G,A-3'      (SEQ ID NO:9)

Sense primer #2:     5'-G,A,G/A,A/T,T,A/C/T,G,A,C/T,I,I,I,C,C,I,G,G/C,I,C,A-3'    (SEQ ID NO:10)

Antisense primer #2: 5'-T,G,I,C/G,C,I,G,G,I,I,I,G/A,T,C,T/G/A,A,T/A,C/T,T,C-3'   (SEQ ID NO:11)

Antisense primer #3: 5'-A,C/A/G,C/T,T,C,G/A,T,C,I,C,C,I,C,C,I,I,I,G/A,T,G-3'     (SEQ ID NO:12)
```

This human homologue commercially, publicly, or otherwise available for the purposes of this invention is cloned and expressed in insect cells. The nucleotide and amino acid sequences of human CMP SA synthetase are shown in FIGS. 29 and 30 respectively. The characterization of CMP-SA synthetase, and the use of CMP-SAS, as well as sialic acid synthetase (SAS), in engineering the sialic acid metabolic pathway is described in greater detail in Example 7, below.

Example 4

Isolation and Inhibition of Glucosaminidase

It is recognized that insect cells could possess additional N-acetylglucosaminidase enzymes other than the enzyme responsible for generating low-mannose structures, so both recombinant DNA and biochemical approaches are implemented to isolate the target N-acetylglucosaminidase gene. PCR techniques are used to isolate fragments of N-acetylglucosaminidase genes by the same strategies used The PCR amplified fragments are cloned and sequenced using the chain termination method (Sanger et al. (1977) *Proc. Natl. Acad. Sci. USA* 74:5463–5467). The results are used to design exact-match oligonucleotide primers to isolate an N-acetylglucosaminidase clone(s) from existing Sf9 and/or High Five™ lambda ZAPII cDNA libraries by sibling selection and PCR (Jarvis et al. (1997) *Glycobiology* 7:113–127, Kawar et al. (1997) *Glycobiology* 7:433–443). The library is consecutively split into sub-pools that score positive in PCR screens until a positive sub-pool of approximately 2,000 clones is obtained. These clones are then screened by plaque hybridization (Benton et al. (1977) *Science* 196:180–182) using the cloned PCR fragment, and positive clones are identified and plaque purified. The cDNA(s) are then excised in vivo as a pbluescript-based subclone in *E. coli*.

Isolation of N-Acetylglucosaminidases Using Biochemical Techniques

Since insect cells may have multiple N-acetylglucosaminidases, a biochemical purification approach is also used to broaden the search for the cDNA encoding the target enzyme. A polyclonal antiserum against a *Manduca sexta* N-acetylglucosaminidase (Koga et al. (1983) *Manduca sexta Comparative Biochemistry and Physiology* 74:515–520) is used to examine Sf9 and High Five™ cells for cross-reactivity. This antiserum is used to probe for the N-acetylglucosaminidase during biochemical isolation techniques. In addition, specific assays for N-acetylglucosaminidase described earlier are used to monitor enzyme activity in isolated biochemical fractions.

The target N-acetylglucosaminidase is membrane bound, so it must be solubilized using a detergent such as Triton-X 100 prior to purification. Once solubilized, the enzyme is purified by a combination of gel filtration, ion exchange, and affinity chromatography. For affinity chromatography, the affinants 6-aminohexyl thio-N-acetylglucosaminide (Chipowsky et al. (1973) *Carbohydr. Res.* 31:339–346) or BSA modified with thio-N-acetylglucosaminide (Lee et al. (1976) *Biochemistry* 15:3956–3963) is tried first. If necessary, 6-aminohexyl a-D-[2-(thio-2-amino-2-deoxy-b-D-glucosaminyl)-mannopyranodside or other thio-oligosaccharides are synthesized and used as affinants. Affinity matrices are prepared using commercially available products.

Alternatively, the target enzyme is "anchored" to the membrane by a glycophosphoinositide. In such a case, a specific phospholipase C is used to release the active enzyme from the membrane, and the use of detergent for solubilization is avoided.

The purity of the enzyme is examined with SDS-PAGE and mass spectroscopy, and the activity of the enzyme characterized. Once the enzyme is sufficiently purified, its amino-terminal region is sequenced by conventional Edman degradation techniques, available commercially. If N-terminal blockage is encountered, the purified protein are digested, peptides purified, and these peptides are used to obtain internal amino acid sequences. The resulting sequence information is used to design degenerate oligonucleotide primers that are used, in turn, to isolate cDNAs as described above.

Expression of Glucosaminidase

Isolated full-length cDNAs are sequenced, compared to other N-acetylglucosaminidase cDNAs, and expressed using known polyhedrin-based baculovirus vectors. The overexpressed proteins are purified, their biochemical activities and substrate specificities characterized, and new polyclonal antisera is produced to establish the subcellular locations of the enzymes in insect cells. The locations are optionally identified by using the antisera in conjunction with secretory pathway markers, including Golgi and endoplasmic reticulum specific dyes and GFP-tagged N-glycan processing enzymes commercially, publicly, or otherwise available for the purposes of this invention. Evaluation of the N-glycan structures on secreted glycoproteins from insect cells overexpressing the glucosaminidase gene demonstrates the involvement of this enzyme in N-glycan processing as opposed to lysosomal degradation, a common activity for other glucosaminidases.

Example 5

Expression of the Model Glycoprotein Transferrin

Figure 26:
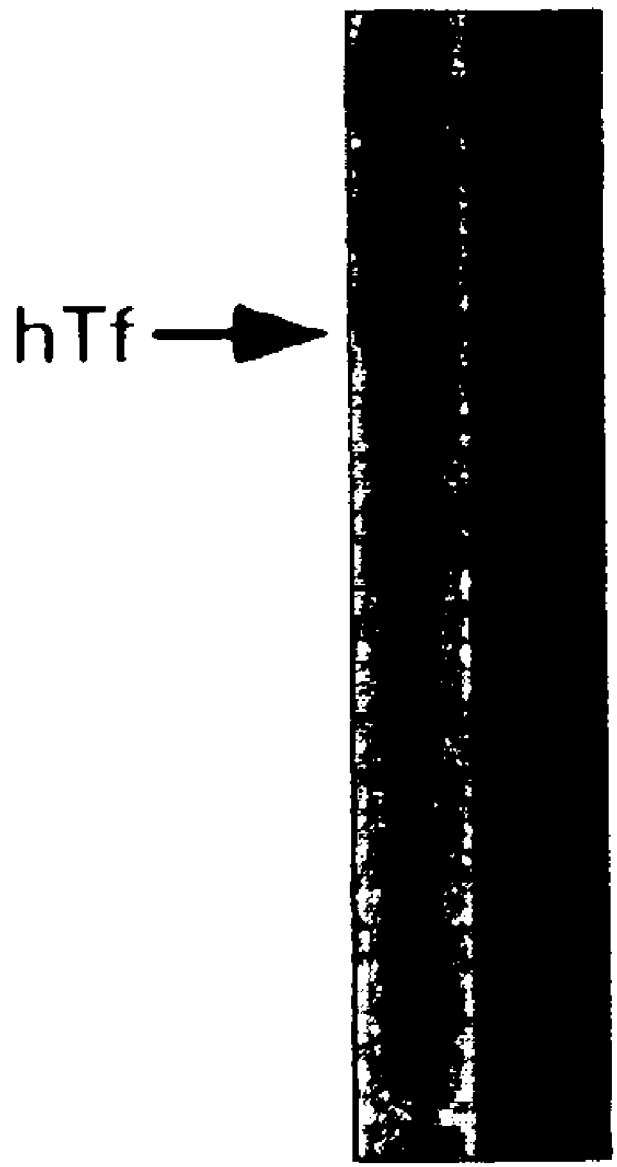
FIG. 26 depicts detection of purified (P) transferrin (hTf) or transferrin from unpurified insect cell lysates (M) following separation on an SDS-PAGE gel, as described the Examples.
Figure 34:
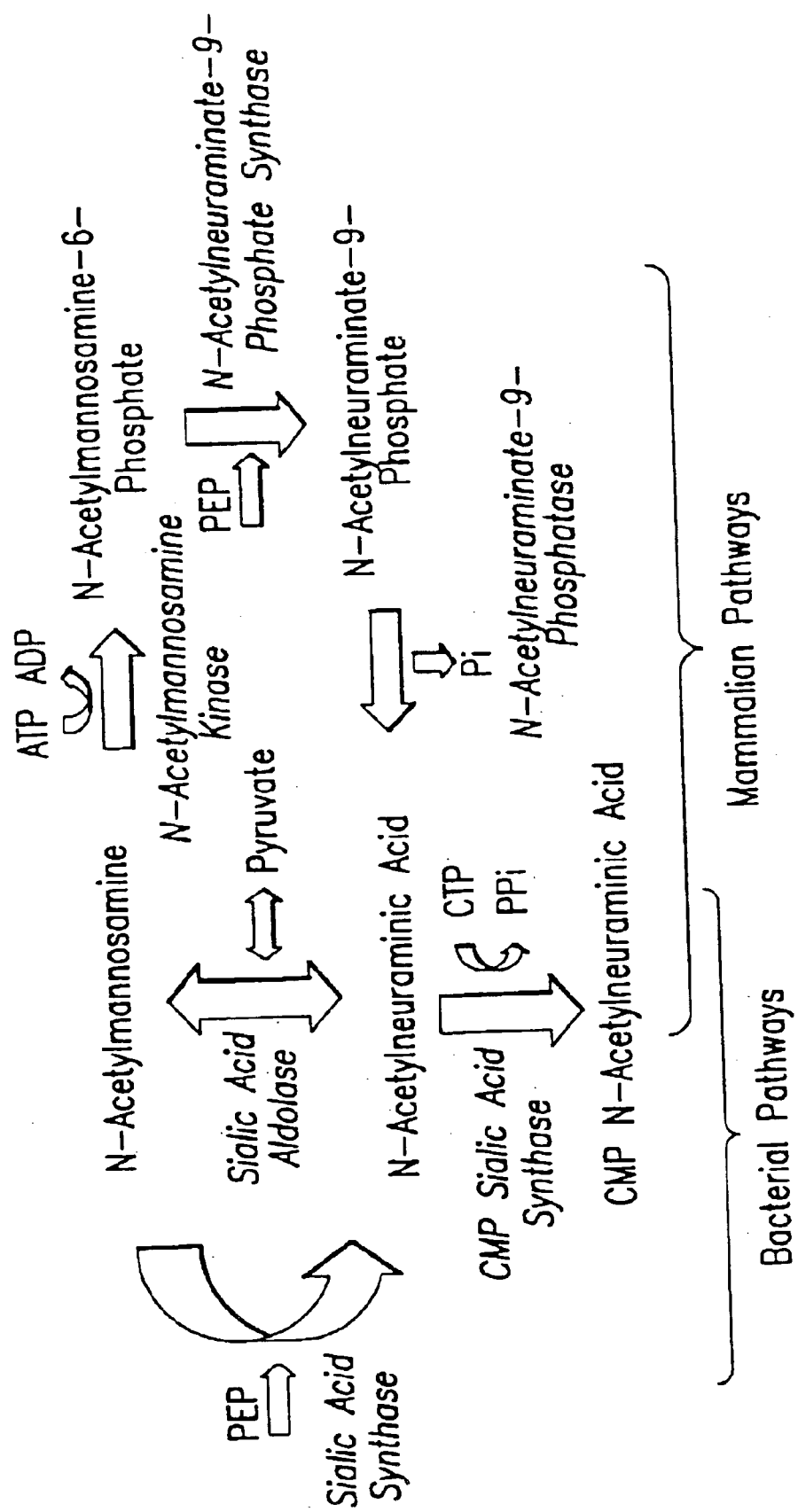
FIG. 34 depicts bacterial and mammalian sialic acid metabolic pathways.

The gene encoding human transferrin as described in Genbank accession No. S95936 is cloned into the baculovirus vector, expressed in multiple insect cell lines, and purified to homogeneity. FIG. 26 shows SDS-PAGE of transferrin from insect cells (M=unpurified lysates, P=purified protein). Similar techniques are used to express and purify this glycoprotein in the target cell line(s) of interest following manipulation of the glycosyltransferase and CMP-SA production pathways.

Once the transferrin is purified to homogeneity, the structures of the oligosaccharides which are N-linked at two sites of the transferrin are analyzed using 3-dimensional HPLC mapping techniques. Over 450 N-glycans have been mapped with this technique. For example, characterization of the N-linked oligosaccharides attached to the heavy chain of secreted and intracellular IgG is described. Confirmation of particular carbohydrate structures is provided by treating the oligosaccharides with glycosidases and re-eluting through the HPLC columns. Additional structural information on unknown oligosaccharides are obtained using mass spectrometry and NMR techniques previously used for analysis of IgG glycoforms (Hsu et al. (1997) *J. Biol. Chem.* 272:9062–9070).

These analytical techniques allow the identification and quantification of N-glycans to determine if a fraction of these structures are sialylated oligosaccharides. Sialylation is confirmed by treating the purified N-glycan with sialidase from *A. ureafaciens* and measuring the release of sialic acid using HPAEC-PAD.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Example 6

Cloning, Expression, and Characterization of the Human Sialic Acid Synthetase (SAS) Gene and Gene Product This example reports the cloning and characterization of a novel human gene having homology to the *Escherichia coli* sialic acid synthetase gene (neuB). This human gene is ubiquitously expressed and encodes a 40 kD enzyme which results in N-acetylneuraminic acid (Neu5Ac) and 2-keto-3-deoxy-D-glycero-D-galacto-nononic acid (KDN) production in insect cells upon recombinant baculovirus infection. In vitro the human enzyme uses N-acetylmannosamine-6-phosphate and mannose-6-phosphate as substrates to generate phosphorylated forms of Neu5Ac and KDN, respectively, but exhibits much higher activity toward the Neu5Ac phosphate product.

In order to identify genes involved in sialic acid biosynthesis in eukaryotes, homology searches of a human expressed sequence tag (EST) database were performed using the E. coli sialic acid synthetase gene. A cDNA of approximately 1 kb with a predicted open reading frame (ORF) of 359 amino acids was identified. Northern blot analysis indicated that the mRNA is ubiquitously expressed, and in vitro transcription and translation along with recombinant expression in insect cells demonstrated that the human sialic acid synthetase (SAS) gene encodes a 40 kD protein. SAS rescued an E. coli neuB mutant although less efficiently than neuB. Neu5Ac production in insect culture supplemented with ManNAc further supported the role of SAS in sialic acid biosynthesis. In addition to Neu5Ac, a second sialic acid, KDN, was generated suggesting that the human enzyme has broad substrate specificity. The human enzyme (SAS), unlike its E. coli homologue, uses phosphorylated substrates to generate phosphorylated sialic acids and thus likely represents the previously described sialic acid-9-phosphate synthetase of mammalian cells (Watson et al., J. Biol. Chem. 241, 5627–5636 (1966)).

Identification of a Human Sialic Acid Synthetase Gene

The E. coli sialic acid synthetase gene (Annunziato et al., J. Bacteriol. 177, 312–319 (1995)) was used to search the human EST database of Human Genome Sciences, Inc. (Rockville, Md.). One EST with significant homology to the neuB gene was found in a human liver cDNA library and used to identify a full length cDNA (FIG. 35A) with an ORF homologous to the bacterial synthetase over most of its length. The putative synthetase consisted of 359 amino acids (SEQ ID NO:6) while the neuB gene product contained 346 amino acids (SEQ ID NO:8). Alignment of the human against the bacterial enzyme demonstrated that significant differences were found primarily in the N-terminus (FIG. 35B). Overall, the two synthetases were found to be 36.1% identical and 56.1% similar at the amino acid level.

Figure 36A:
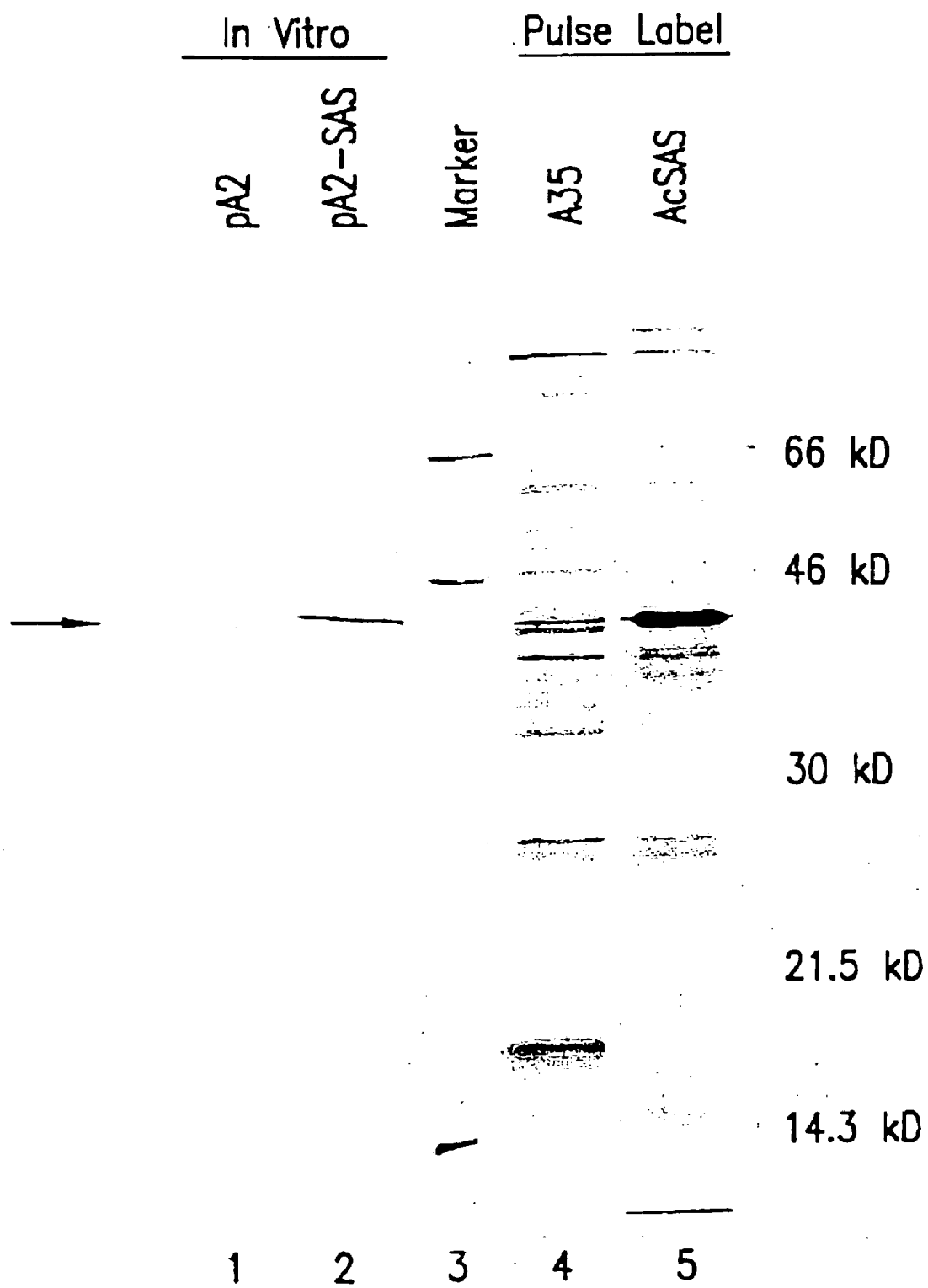
FIG. 36 (A) depicts an autoradiogram of human sialic acid synthetase gene products following gel electrophoresis. The lanes labeled "In Vitro" represent in vitro transcription and translation products of SAS cDNA (amplified via polymerase chain reaction (PCR)). Lane 1 ("pA2") depicts a negative control reaction in which pA2 plasmid (without the SAS cDNA) was PCR amplified, transcribed, translated, and radiolabeled. Lane 2 ("pA2-SAS") depicts a sample reaction in which pA2-SAS plasmid (containing the human SAS cDNA) was PCR amplified, transcribed, translated, and radiolabeled. Lane 3 ("Marker") depicts radiolabeled protein standards migrating at approximately 66, 46, 30, 21.5, and 14.3 kD. The lanes labeled "Pulse Label" show radioactive $^{35}$S pulse labeling of polypeptides from insect cells infected by virions not containing or containing the human SAS cDNA. Lane 4 ("A35") depicts a negative control reaction of radiolabled polypeptides from insect cells infected with virions not containing the SAS cDNA. Lane 5 ("AcSAS") depicts a sample reaction of radiolabeled polypeptides from insect cells infected with baculovirus containing the human SAS cDNA.
Figure 36B:
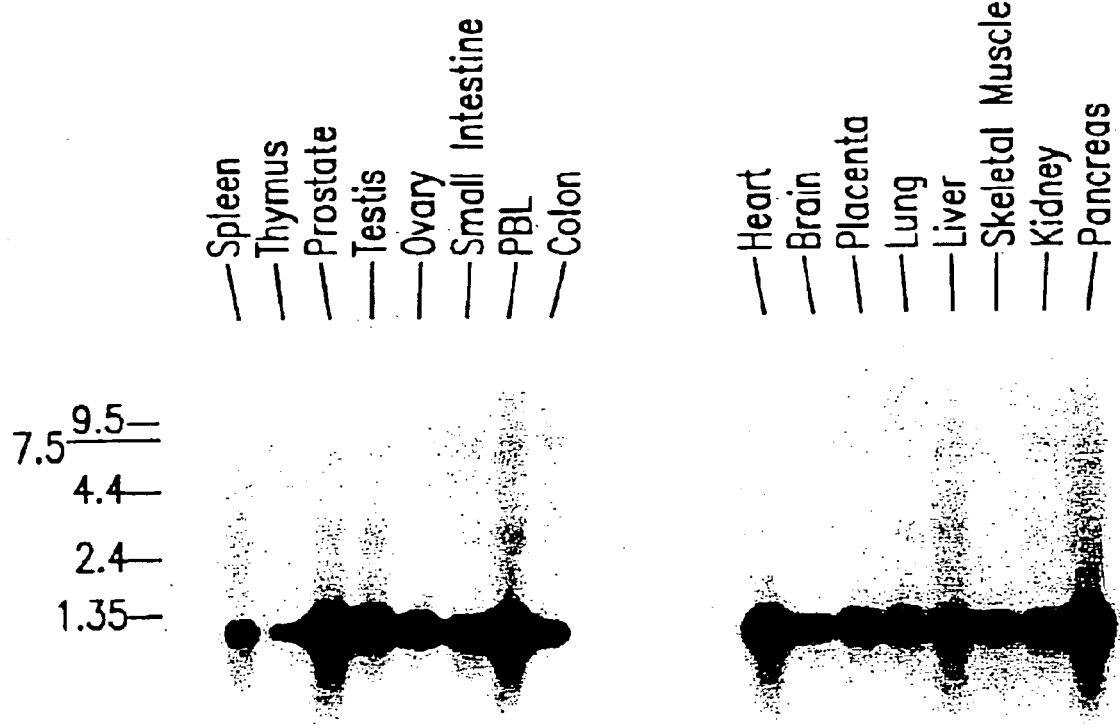

The product of a cDNA amplification with a T7 promoter was expressed by in vitro transcription and translation using rabbit reticulocyte lysates. The generation of an ~40 kD protein, consistent with a predicted molecular weight of 40.3 kD, confirmed the existence of an ORF (FIG. 36A, lane 2). The negative control, namely the vector without an insert, did not produce a protein product (FIG. 36A, lane 1). Northern blot analysis was performed on poly-A+ RNA blots representing a selection of human tissues (FIG. 36B). The full-length cDNA was radio-labeled and used as probe. A band of expected size, ~1.3 kb, was observed in all tissues tested suggesting that the putative synthetase is ubiquitously expressed.

Expression and Purification of Human Sialic Acid Synthetase

SAS was inserted into baculovirus under the polh promoter using lacZ as a positive selection marker. After transfection and viral titering, the resulting virus (AcSAS) was used to infect Spodoptera frugiperda (Sf-9) cells followed by pulse labeling. An ~40 kD band was observed in the Sf-9 lysates from cells infected by AcSAS (FIG. 36A, lane 5) and not in the mock infected control (FIG. 36A, lane 4). Furthermore, this band co-migrated with the protein produced in vitro. To verify SAS expression, the band was visualized in the non-nuclear fraction (Miyamoto et al., Mol. Cell. Biol. 5, 2860–2865 (1985)) after electrophoretic transfer to a ProBlott™ membrane and Ponceau S staining (data not shown) and excised for amino acid sequencing. The five N-terminal amino acids were identical to the second through sixth amino acids of the predicted protein (data not shown). Interestingly, the initiator methionine was also removed from the purified recombinant E. coli sialic acid synthetase (Vann et al., 1997).

In Vivo Activity of Human Sialic Acid Synthetase

Figure 37A:
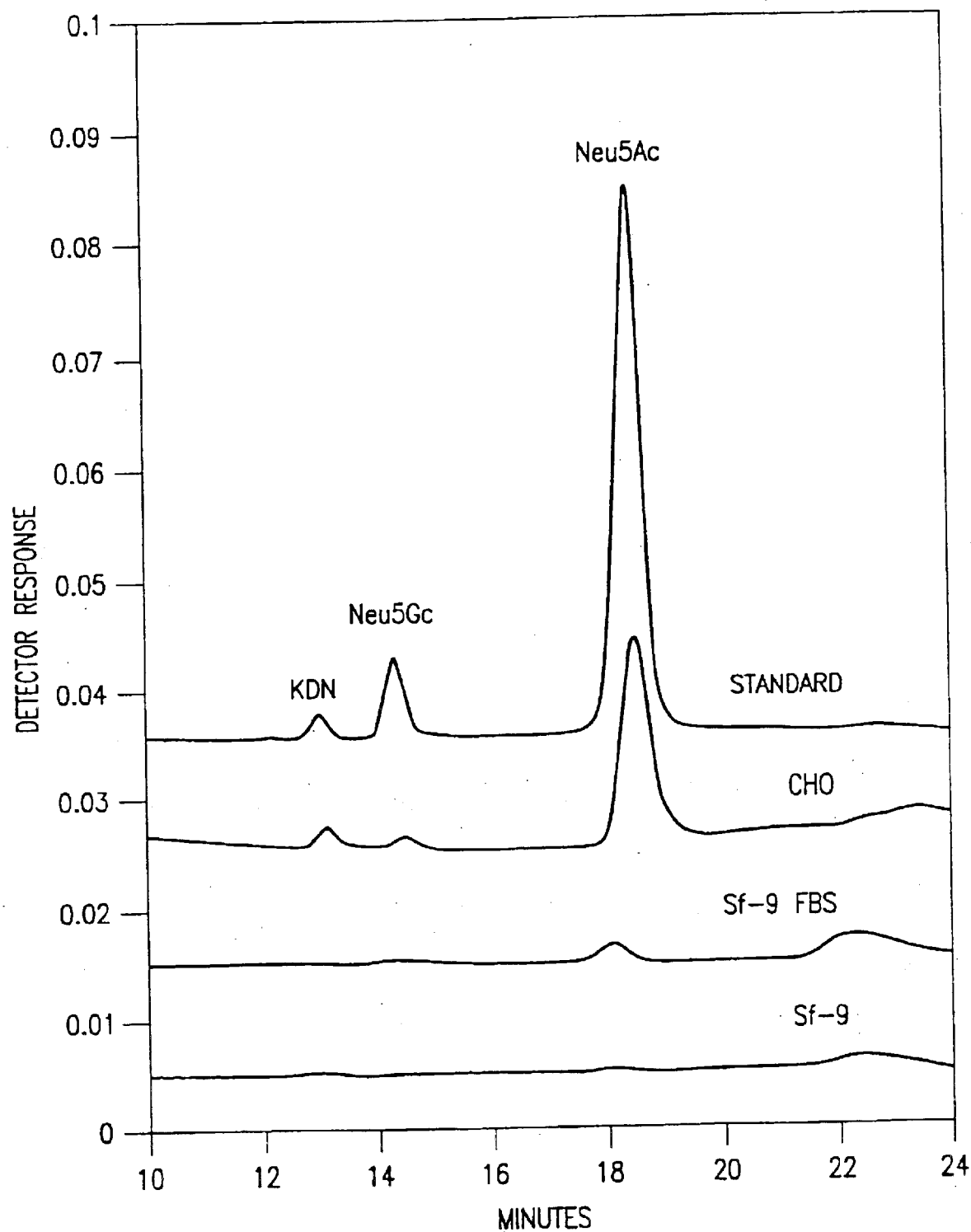
FIG. 37 depicts chromatograms indicating the in vivo sialic acid content of various cells as monitored following DMB derivitization and reverse phase HPLC separation.
FIG. 37(D) HPAEC (high performance anion-exchange chromatography) analysis of lysates from Sf-9 cells infected with AcSAS or A35 baculovirus with and without aldolase treatment. Samples were diluted prior to column loading to normalize sialic acid quantities based on original sample protein concentration. Neu5Ac standard is shown at 250 pmol and KDN standard is shown at 100 pmol.

Covalent labeling of sialic acids with the fluorescent reagent 1,2-diamino-4,5-methylene dioxybenzene dihydrochloride (DMB) allows very specific and sensitive sialic acid detection (Hara et al., Anal. Biochem. 179, 162–166 (1989); Manzi et al., Anal. Biochem. 188, 20–32 (1990)). The DMB reaction products are identified after separation by reverse phase HPLC chromatography. Using this technique, sialic acid standards were measured in quantities as low as 50 fmol (data not shown). Sialic acid levels of an insect cell line (Sf-9) and a mammalian cell line (Chinese hamster ovary, CHO) were compared (Table 2). The sialic acid content in cell lysates before and after filtration through a 10,000 MWCO membrane was determined by DMB labeling and HPLC separation. The native sialic acid levels in Sf-9 cells grown without fetal bovine serum (FBS) supplementation are substantially lower than the levels found in CHO cells (Table 2; FIG. 37A). To ensure that the low sialic acid content was not due to the absence of serum, the sialic acid content of insect cells cultured in 10% FBS was determined. Even with FBS addition, the Neu5Ac content of Sf-9 cells is nearly an order of magnitude lower than the content of CHO cells (Table 2). The origin of the sialic acid detected in insect cells, whether natively produced or the result of contamination from the media, is not clear since even serum free insect cell media contains significant levels of sialic acid (data not shown).

TABLE 2

Sialic Acid Content of CHO and Sf-9 Cell Lines

| | KDN (fmol/μg protein) | | Neu5Ac (fmol/μg protein) | |
|---|---|---|---|---|
| | +Filtration | −Filtration | +Filtration | −Filtration |
| Sf-9 | — | — | 20 | 30 |
| Sf-9 + FBS | — | — | 80 | 600 |
| CHO | 70 | 100 | 900 | 4,200 |

CHO and Sf-9 cells were grown to confluency in T-75 flasks. Cell lysates with and without 10,000 MWCO filtration were analyzed for sialic acid content following DMB derivatization and HPLC separation. Sialic acid levels have been normalized based on lysate protein content. Dashes indicate sialic acid was not detectable.

Figure 37B:
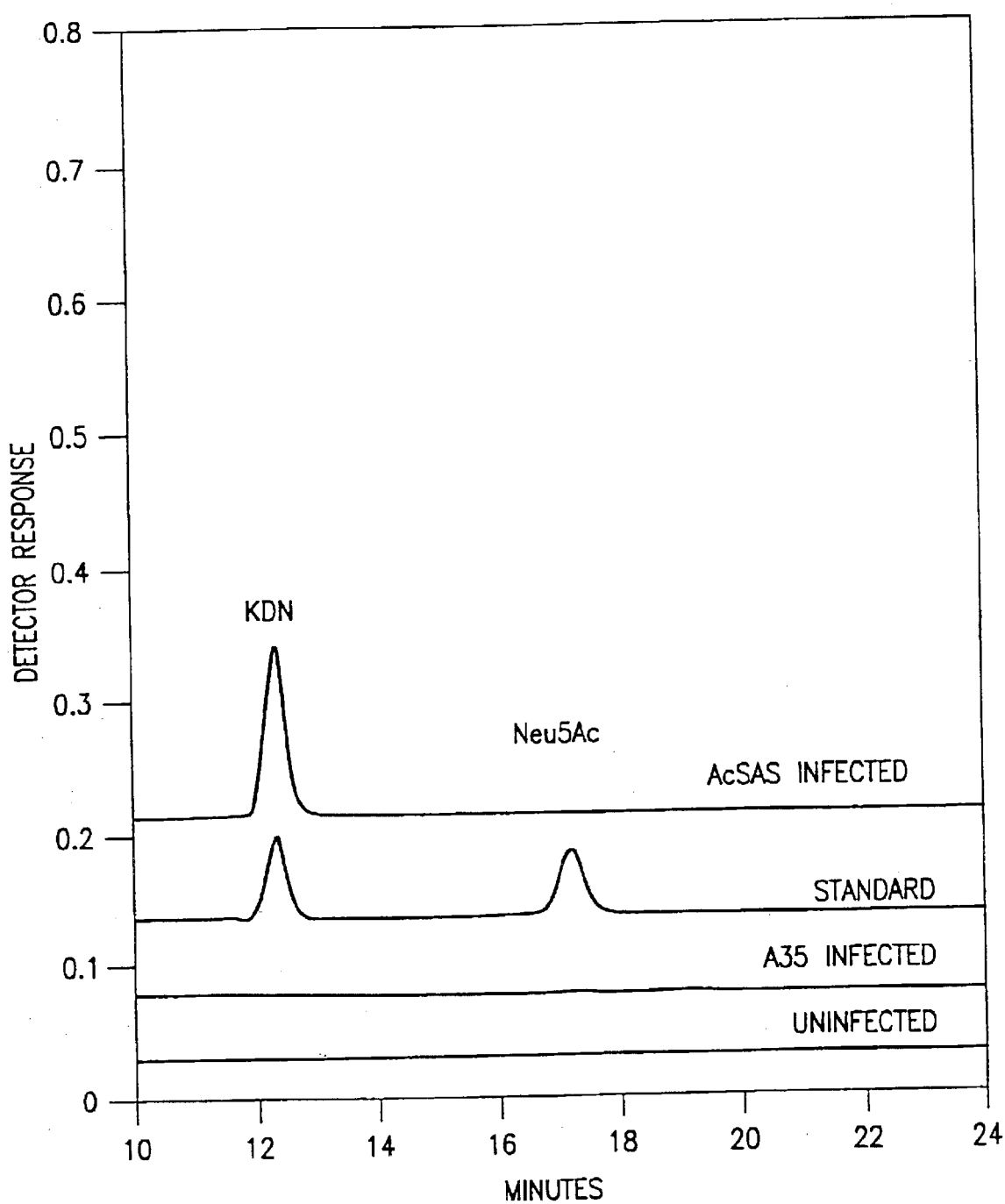

The lack of large sialic acid pools in Sf-9 cells grown in serum-free media facilitated the detection of sialic acids produced by recombinant enzymes. In order to examine the production of sialic acids from cells infected with recombinant virus, Sf-9 cells were infected with AcSAS and a negative control virus, A35. The A35 virus was generated by recombining a transfer vector without a gene inserted downstream of the polh promoter. Low levels of Neu5Ac were observed in lysates from insect cells infected by either virus (FIG. 37B) indicating additional Neu5Ac was not produced following the expression of SAS. However, a significant new peak was seen in AcSAS lysates at 12.5 min. that was not observed in A35 negative control lysates (FIG. 37B). Published chromatograms suggested the unknown early eluting peak could be N-glycolylneuraminic acid (Neu5Gc) or KDN (Inoue et al., 1998). The elution time of the unknown peak was the same as DMB-derivatized KDN standard (FIG. 37B) and co-chromatographed with authentic DMB-KDN (data not shown) confirming KDN generation in AcSAS infected Sf-9 cells. KDN was not detected in uninfected Sf-9 cells either with or without FBS supplementation (Table 2).

Figure 37C:
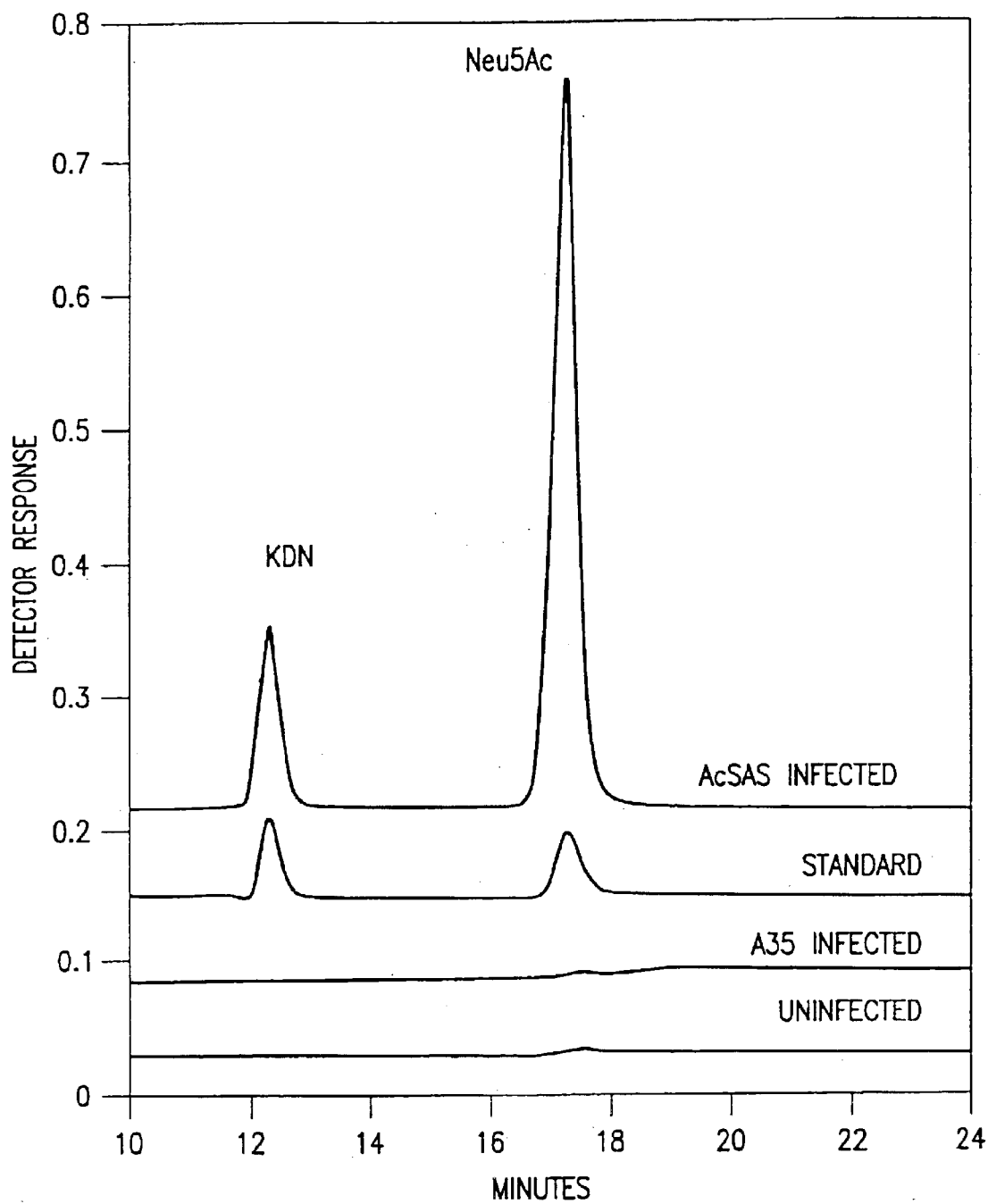

In a further attempt to demonstrate Neu5Ac synthetic functionality, the culture media was supplemented with ManNAc, the metabolic precursor of Neu5Ac. In addition to a DMB-KDN peak, a prominent peak eluting at 17.5 min. corresponding with that of the Neu5Ac standard was observed from the lysates of ManNAc supplemented Sf-9 cells infected with AcSAS (FIG. 37C). Neu5Ac quantities were more than 100 times lower in the uninfected lysates and even less in A35 infected lysates (Table 2).

Sialic acid levels were quantified in lysates of uninfected, A35 infected, and AcSAS infected Sf-9 cells grown in media with and without Man, mannosamine (ManN), or ManNAc supplementation (Table 3). In uninfected cells, Man feeding resulted in detection of KDN slightly above background, and ManNAc feeding marginally increased Neu5Ac levels in uninfected and A35 infected cells (Table 3). ManN supplementation had no effect on KDN levels but increased Neu5Ac levels (Table 3). The most significant changes in sialic acid levels occurred with AcSAS infection. AcSAS infection of Sf-9 cells led to large increases in KDN levels with slight enhancements upon Man or ManNAc supplementation. Both AcSAS infection and ManNAc feeding were required to obtain substantial Neu5Ac levels.

Figure 38A:
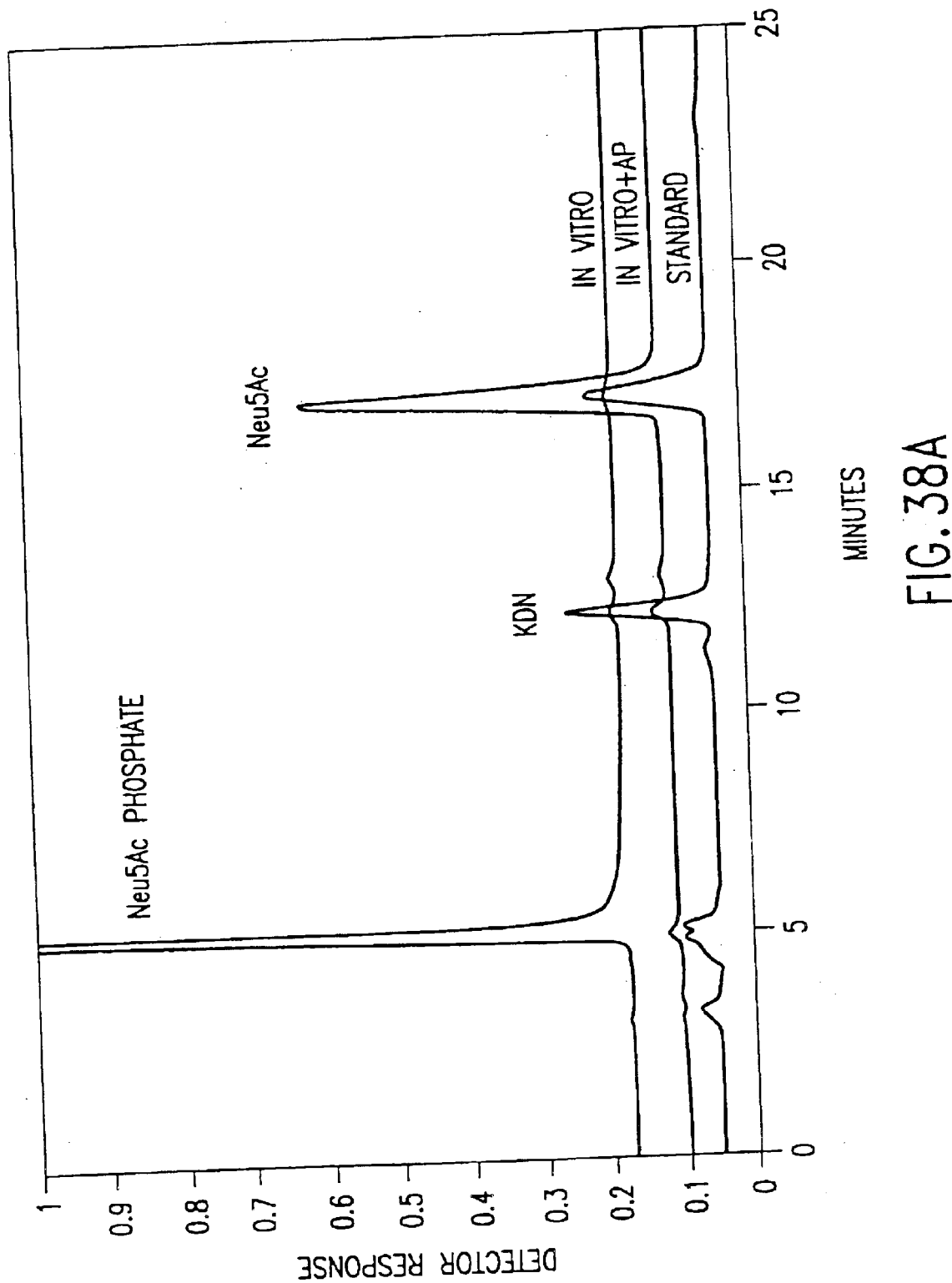
FIG. 38 depicts chromatograms of in vitro assays for sialic acid phosphorylation activity. Assays were performed with and without alkaline phosphatase (AP) treatment.
Figure 38B:
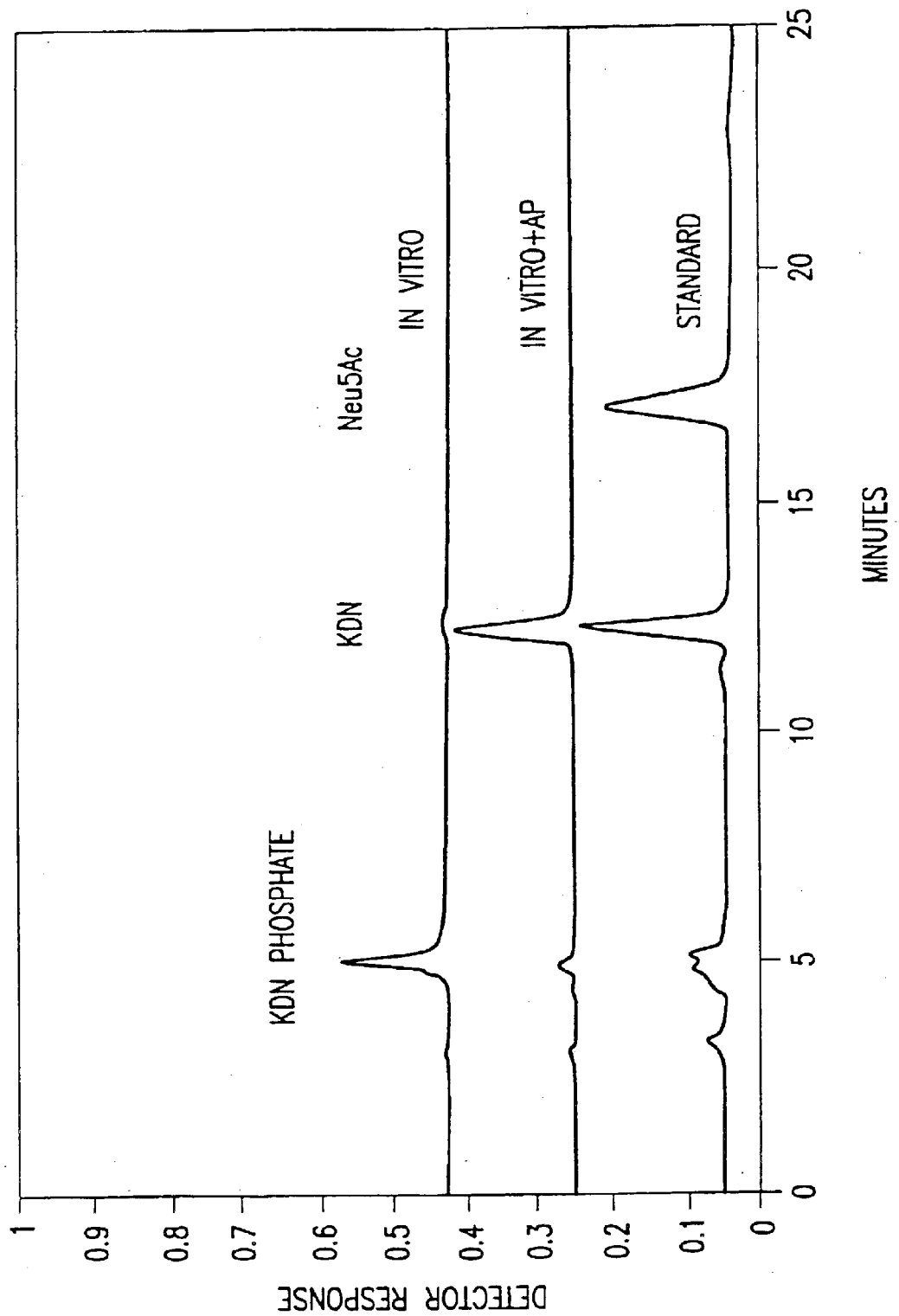

AcSAS infected cell lysates incubated with ManNAc-6-P and PEP produced a peak eluting at 5.5 min (FIG. 38A) consistent with phosphorylated sugars. In previous studies, phosphorylated KDN was detected as DMB-KDN after alkaline phosphatase (AP) treatment and DMB derivatization (Angata et al., *J. Biol. Chem.* 274, 22949–22956 (1999)). Similarly, the peak eluting at 5.5 min. was exchanged for one that eluted at the same time as authentic Neu5Ac following AP treatment (FIG. 38A). Likewise, an early eluting peak from the incubation mixture containing Man-6-P yielded a KDN peak after AP treatment (FIG. 38B). No sialic acid products were detected when A35 infected cell lysates were used in the equivalent assays or when Man or ManNAc were used as substrates (data not shown).

Assays were performed by incubating lysates with different substrate solution concentrations of Man-6-P and ManNAc-6-P in order to evaluate substrate preference. After incubation for a fixed time period, the samples were treated with AP, and DMB derivatives of Neu5Ac and KDN were quantified and compared (Table 4). When equimolar

TABLE 3

Sialic Acid Content of Sf-9 with Media Supplementation

| Feeding: | KDN (fmol/μg protein) | | | | Neu5Ac (fmol/μg protein) | | | |
|---|---|---|---|---|---|---|---|---|
| | None | Man | ManN | ManNAc | None | Man | ManN | ManNAc |
| No Infection | — | 20 | — | — | 30 | 20 | 60 | 140 |
| A35 | — | — | — | — | 80 | 80 | 100 | 120 |
| AcSAS | 5,300 | 7,600 | 5,200 | 6,300 | 50 | 40 | 200 | 27,000 |

Uninfected, A35 infected, and AcSAS infected Sf-9 cells were grown in unsupplemented media and media that was supplemented with 10 mM Man, ManN, or ManNAc. Cell lysates were analyzed for KDN and Neu5Ac content using DMB derivatization and HPLC separation. Sialic acid levels have been normalized based on lysate protein content. Dashes indicate sialic acid was not detectable.

Figure 37D:
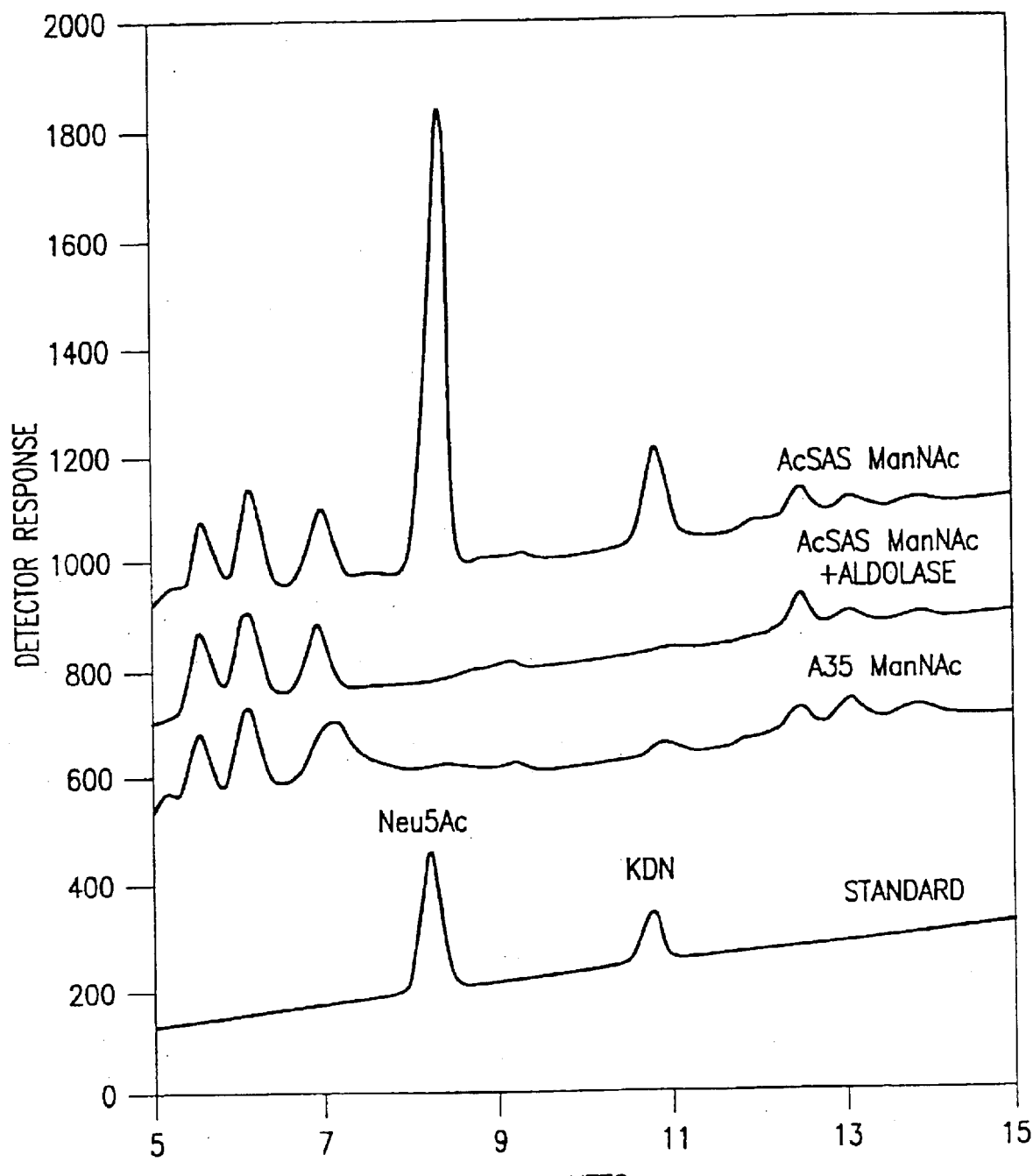

The presence of KDN and Neu5Ac in AcSAS lysates has been confirmed by high-performance anion-exchange chromatography (HPAEC) with a pulsed amperometric detector (FIG. 37D). When culture media is supplemented with ManNAc, peaks with elution times corresponding to authentic KDN and Neu5Ac standards are seen in AcSAS infected lysates that are absent in A35 infected lysates. Neu5Ac aldolase has been demonstrated previously to break Neu5Ac into ManNAc and pyruvic acid (Comb and Roseman, *J. Biol. Chem.* 235, 2529–2537 (1960)) and KDN into Man and pyruvic acid (Nadano et al., *J. Biol. Chem.* 261, 11550–11557 (1986)). KDN and Neu5Ac disappear from the AcSAS lysates after aldolase treatment (FIG. 37D). A similar disappearance of the sialic acid peaks following aldolase treatment was observed using DMB-labeling and HPLC analysis (data not shown).

In Vitro Activity of Human Sialic Acid Synthetase

The mammalian pathway for Neu5Ac synthesis uses a phosphate intermediate (Jourdian et al., *J. Biol. Chem.* 239, PC2714–PC2716 (1964); Kundig et al., *J. Biol. Chem.* 241, 5619–5626 (1966); Watson et al., *J. Biol. Chem.* 241, 5627–5636 (1966)) while the *E. coli* pathway directly converts ManNAc and PEP to Neu5Ac (Vann et al., *Glycobiology* 7, 697–701 (1997)). In order to determine which substrates are used by the human enzyme, in vitro assays were performed using lysates of infected Sf-9 cells and protein purified from the prokaryotic expression system. Lysates or purified protein plus PEP and MnCl$_2$ (Angata et al., *J. Biol. Chem.* 274, 22949–22956 (1999)) were incubated with Man, mannose-6-phosphate (Man-6-P), ManNAc, or ManNAc-6-P followed by DMB labeling and HPLC analysis.

amounts of substrates are used, Neu5Ac production is significantly favored over KDN especially at higher equimolar concentrations (10 and 20 mM) of the two substrates. Only when the substrate concentration of ManNAc-6-P is substantially lower than the Man-6-P levels are production levels of the two sialic acids comparable. When the ManNAc-6-P concentration is 1 mM and the Man-6-P level is 20 mM, the Neu5Ac:KDN production ratio approaches unity. Therefore, the enzyme prefers ManNAc-6-P over Man-6-P in the production of phosphorylated forms of Neu5Ac and KDN, respectively.

TABLE 4

Competitive Formation of Neu5Ac and KDN

| Concentration in Substrate Solution (mM) | | Final Concentration (pmol/μl) | | Neu5Ac/KDN |
|---|---|---|---|---|
| Man-6-P | ManNAc-6-P | KDN | Neu5Ac | Ratio |
| 1 | 1 | 8 | 33 | 4.2 |
| 5 | 1 | 19 | 47 | 2.5 |
| 10 | 1 | 33 | 53 | 1.6 |
| 20 | 1 | 56 | 60 | 1.1 |
| 5 | 5 | 14 | 190 | 14 |
| 10 | 10 | 18 | 440 | 24 |
| 20 | 20 | 16 | 820 | 51 |

TABLE 4-continued

Competitive Formation of Neu5Ac and KDN

| Concentration in Substrate Solution (mM) | | Final Concentration (pmol/µl) | | Neu5Ac/KDN Ratio |
|---|---|---|---|---|
| Man-6-P | ManNAc-6-P | KDN | Neu5Ac | |
| 20 | 5 | 40 | 300 | 7.6 |
| 20 | 10 | 18 | 470 | 25 |

Lysates from AcSAS infected Sf-9 cells were incubated with substrate solutions containing the indicated concentrations of Man-6-P and ManNAc-6-P. After incubation and AP treatment, samples were analyzed for KDN and Neu5Ac content using DMB derivatization and HPLC separation. Neu5Ac and KDN concentrations of the final solution (50 µl) and the Neu5Ac/KDN ratio are reported.

Discussion of Human Sialic Acid Synthetase Characterization

We have identified the sequence of a human sialic acid phosphate synthetase gene, SAS, whose protein product condenses ManNAc-6-P or Man-6-P with PEP to form Neu5Ac and KDN phosphates, respectively. To our knowledge, this is the first report of the cloning of a eukaryotic sialic acid phosphate synthetase gene. Despite the importance of sialic acids in many biological recognition phenomena, sialic acid phosphate synthetase genes have not been cloned because the enzymes they encode are unstable and difficult to purify (Watson et al., *J. Biol. Chem.* 241, 5627–5636 (1966); Angata et al., *J. Biol. Chem.* 274, 22949–22956 (1999)). Even the *E. coli* sialic acid synthetase enzyme, whose sequence is known, has low specific activity and is unstable (Vann et al., *Glycobiology* 7, 697–701 (1997)).

Consequently, a bioinformatics approach based on the *E. coli* synthetase sequence was used to identify a putative human gene 36% identical and 56% similar to neuB. In vitro transcription and translation verified an open reading frame which encoded a 359 amino acid protein. In addition, Northern blots revealed ubiquitous transcription of the human synthetase gene in a selection of human tissues. The wide distribution of SAS mRNA is consistent with the detection of sialic acids in many different mammalian tissues (Inoue and Inoue, *Sialobiology and Other Novel Forms of Glycosylation* (Osaka, Japan: Gakushin Publishing) pp.57–67 (1999)).

Using the baculovirus expression system, the 40 kD sialic acid phosphate synthetase enzyme, SAS, was expressed in cells. The use of Sf-9 cells which have little if any native sialic acid greatly facilitated the detection of sialic acids and the characterization of SAS. However, Neu5Ac was observed only when insect cells were infected with AcSAS and the cell culture media was supplemented with ManNAc, a sialic acid precursor. This ManNAc feeding requirement indicates that Sf-9 cells may lack sizeable ManNAc pools and synthetic pathways.

SAS was identified based on homology with neuB whose enzyme product directly forms Neu5Ac from ManNAc and PEP (Vann et al., *Glycobiology* 7, 697–701 (1997)). Furthermore, insect cells produce Neu5Ac following recombinant SAS expression and ManNAc supplementation. However, mammalian cells are known only to produce Neu5Ac from ManNAc through a three-step pathway with phosphorylated intermediates. Therefore, in vitro assays were performed to determine the substrate specificity of SAS. Both AcSAS infected insect cell lysates and protein purified from the prokaryotic expression system were assayed using ManNAc and ManNAc-6-P as possible substrates. A rapidly eluting DMB derivatized product, typical of a phosphorylated sialic acid, was observed only when ManNAc-6-P was used as the substrate. Furthermore, this peak disappears with the appearance of an unsubstituted DMB-Neu5Ac peak following AP treatment. SAS therefore condenses PEP and ManNAc-6-P to form a Neu5Ac phosphate product. Although the exact position of the phosphorylated carbon on the product has not yet been specified, SAS is likely the sialic acid phosphate synthetase enzyme of the previously described three-step mammalian pathway (Kundig et al., *J. Biol. Chem.* 241, 5619–5626 (1966); Watson et al., *J. Biol. Chem.* 241, 5627–5636 (1966); Jourdian et al., *J. Biol. Chem.* 239, PC2714–PC2716 (1964)). Despite little if any native pools of sialic acids, Sf-9 cells natively possess the ability to complete the three-step mammalian pathway when only the sialic acid phosphate synthetase gene is provided. Sf-9 cells have been shown to have substantial ManNAc kinase ability (Effertz et al., *J. Biol. Chem.* 274, 28771–28778 (1999)), and phosphatase activity has also been detected in insect cells (Sukhanova et al., *Genetika* 34, 1239–1242 (1998)).

The capacity to produce sialic acids in Sf-9 cells following AcSAS infection and ManNAc supplementation at levels even higher than those seen in a mammalian cell lines such as CHO may help overcome a major limitation of the baculovirus expression system. N-glycans of recombinant glycoproteins produced in insect cells lack significant levels of terminal sialic acid residues (Jarvis and Finn, *Virology* 212, 500–511 (1995); Ogonah et al., *Bio/Technology* 14, 197–202 (1996)). The lack of sialylation on human thyrotropin produced by the baculovirus expression system resulted in rapid in vivo thyrotropin clearance as compared to thyrotropin produced by a mammalian system (Grossmann et al., *Endocrinology* 138, 92–100 (1997)). Generation of significant sialic acid pools along with expression of other genes such as sialyltransferases may lead to production of significant levels of sialylated glycoproteins in insect cells.

Another interesting observation was the occurrence of a second DMB reactive peak in AcSAS infected Sf-9 lysates. This peak has been identified as KDN, a deaminated Neu5Ac. We subsequently demonstrated that the SAS enzyme generates KDN phosphate from Man-6-P and PEP in vitro. While Neu5Ac production in insect cells requires both AcSAS infection and ManNAc supplementation, only AcSAS infection is necessary for KDN synthesis. Therefore, significant substrate pools for the generation of KDN already exist in insect cells or are present in the media. In addition, mannose feeding increased KDN production even further. Interestingly, Man feeding of the uninfected insect cells increased KDN levels above background, and ManNAc feeding also led to higher Neu5Ac levels in uninfected cells. Therefore, insect cells may possess limited native sialic acid synthetic ability. Similar substrate supplementation results have been reported in mammalian cells, as cultivation in Man-rich or ManNAc-rich media enhanced the synthesis of native intracellular KDN and Neu5Ac, respectively (Angata et al., *Biochem. Biophys. Res. Commun.* 261, 326–331 (1999)).

This study is the first report of a eukaryotic gene encoding any enzyme with KDN synthetic ability. Recently, KDN enzymatic activity has been characterized in trout testis, a tissue high in KDN content. KDN is synthesized from Man in trout through a three-step pathway involving a synthetase with a Man-6-P substrate (Angata et al., *J. Biol. Chem.* 274, 22949–22956 (1999)). However, the fish synthetase enzyme, partially purified from trout testis, was approximately 80 kD as compared to the human enzyme of 40 kD.

Furthermore, KDN and Neu5Ac phosphate synthesis in trout were likely catalyzed by two separate synthetase activities (Angata et al., *J. Biol. Chem.* 274, 22949–22956 (1999)) while the current study indicates that both products were generated from a single human enzyme with broad substrate specificity.

Neu5Ac, usually bound to glycoconjugates, is the predominant sialic acid found in mammalian tissue, but KDN, primarily found free in the ethanol soluble fractions, has also been detected all human tissues examined so far (Inoue and Inoue, *Sialobiology and Other Novel Forms of Glycosylation* (Osaka, Japan: Gakushin Publishing, pp.57–67 (1999)). The ratio of Neu5Ac to KDN is on the order of 100:1 in blood cells and ovaries (Inoue et al., 1998), although this ratio may change during development and cancer. The levels of free KDN in newborn fetal cord red blood cells are higher than those of maternal red blood cells (Inoue et al., *J. Biol. Chem.* 273, 27199–27204 (1998)). Furthermore, a 4.2 fold increase in the ratio of free KDN to free Neu5Ac was observed in ovarian tumor cells as compared to normal cells, and the ratio appears to increase with the extent of invasion or malignancy for ovarian adenocarcinomas (Inoue et al., *J. Biol. Chem.* 273, 27199–27204 (1998)).

Because the KDN/Neu5Ac ratio has biological significance, we performed competitive in vitro assays with insect cell lysates using both ManNAc-6-P and Man-6-P as substrates. SAS demonstrated a preference for phosphorylated Neu5Ac over phosphorylated KDN synthesis in vitro, although the concentrations of the particular substrates relative to the enzyme level altered this production ratio. Thus changes in the ratios of free KDN to Neu5Ac observed in different developmental states and cancer tissue may reflect variability either in the levels of specific substrates or the amount of active enzyme present in vivo. The identification of the SAS genetic sequence and characterization of the enzyme it encodes should help further our understanding of sialic acid biosynthesis as well as the roles sialic acids play in development and disease states.

Figure 39:
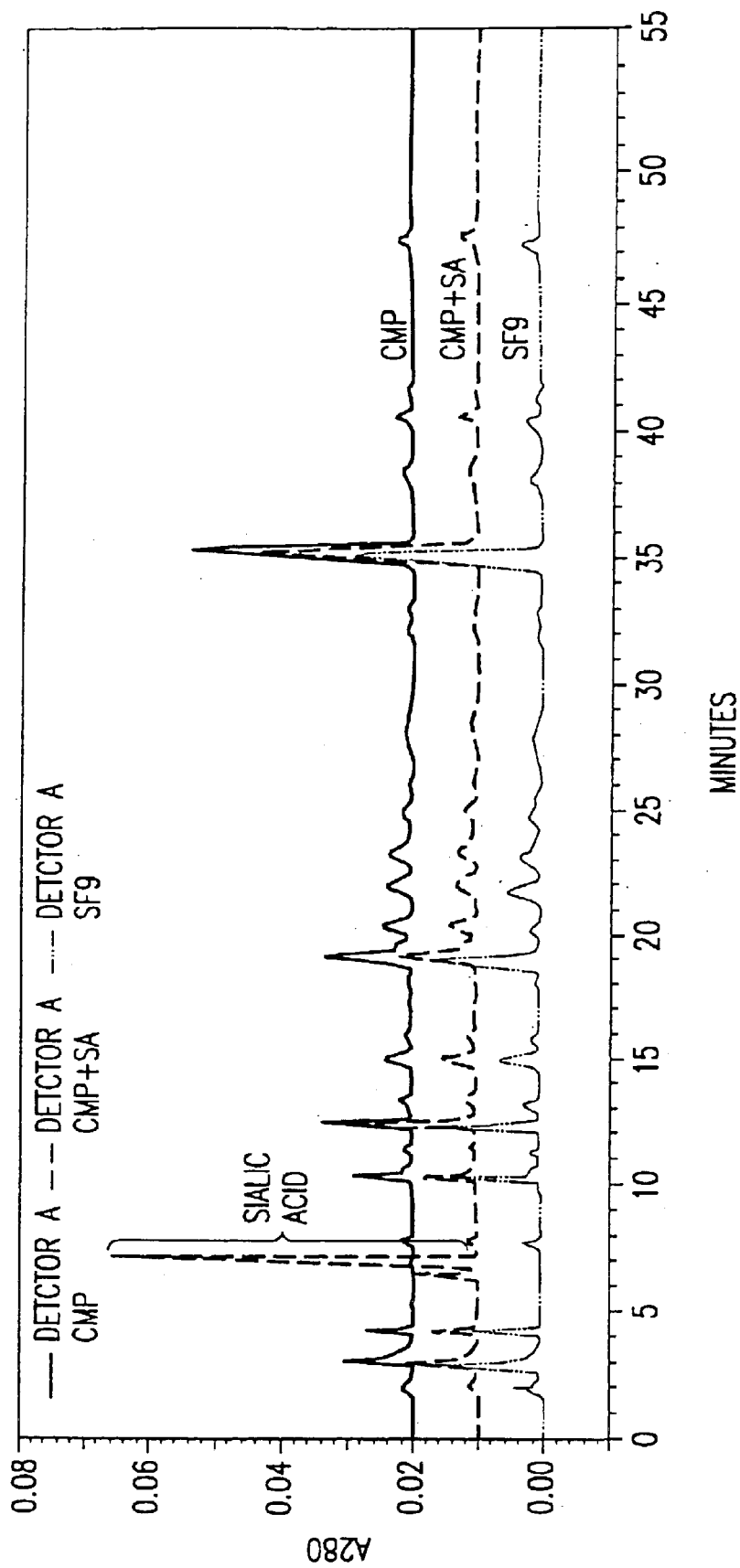
FIG. 39 depicts a chromatogram demonstrating production of sialylated nucleotides in SF-9 insect cells following infection with CMP-SA synthetase and SA synthetase containing baculoviruses. Sf-9 cells were grown in six well plates and infected with baculovirus containing CMP-SA synthase and supplemented with 10 mM ManNAc ("CMP" line), with baculovirus containing CMP-SA synthase and SA synthase plus 10 mM ManNAc supplementation ("CMP+ SA" line), or with no baculovirus and no ManNAc supplementation ("SF9" line).

In FIG. 39 the production of sialylated nucleotides in SF-9 insect cells following infection with human CMP-SA synthetase and SA synthetase containing baculoviruses is demonstrated. Sf-9 cells were grown in six well plates and infected with baculovirus containing CMP-SA synthase and supplemented with 10 mM ManNAc ("CMP" line), baculovirus containing CMP-SA synthase and SA synthase plus 10 mM ManNAc supplementation ("CMP+SA" line), or no baculovirus and no ManNAc supplementation ("SF9" line). The nucleotide sugars from lysed cells were extracted with 75% ethanol, dried, resuspended in water, and filtered through a 10,000 molecular weight cut-off membrane. Samples were then separated on a Dionex Carbopac PA-1 column using a Shimadzu VP series HPLC. Nucleotide sugars were detected based upon their absorbance at 280 nm, and CMP sialic acid standards were shown to elute at approximately 7 minutes. These results demonstrate the ability to produce the desired oligosaccharide products in insect cells via introduction and expression of sialyltransferase enzymes.

Materials and Method of Example 6
Gene Characterization

The *E. coli* neuB coding sequence was used to query the Human Genome Sciences (Rockville, Md.) cDNA database with BLAST software. One EST clone, HMKAK61, from a human (liver) cDNA library demonstrated significant homology to neuB and was chosen for further characterization. The tissue distribution profile was determined by Northern blot hybridization. Briefly, the cDNA was radio-labeled with [$^{32}$P]-dCTP using a RediPrime™II kit (Amersham/Pharmacia Biotech, Piscataway, N.J.) following the manufacturer's directions. Multiple tissue Northern blots containing poly-A+ RNA (Clontech, Palo Alto, Calif.) were pre-hybridized at 42° C. for 4 hours and then hybridized overnight with radio-labeled probe at $1\times10^6$ CPM/ml. The blots were sequentially washed twice for 15 min. at 42° C. and once for 20 min. at 65° C. in 0.1×SSC, 0.1% SDS and subsequently autoradiographed.

Baculovirus Cloning and Protein Expression

The full length ORF was amplified by PCR using the following primers. The forward primer, 5'-TGTAATACGACTCACTATAGGGCGGATCCGCCTCAT GCCGCTGGAGCTGG AGC (SEQ ID NO:13) contained a synthetic T7 promoter sequence (underlined), a BamHI site (italics), a KOZAK sequence (bold), and sequence corresponding to the first six codons of SAS. The minus strand primer, 5'-GTACGGTACCTTATTAAGACTT GATTTT TTTGCC (SEQ ID NO:14), contained an Asp 718 site (italics), two in-frame stop codons (underlined), and sequences representing the last six codons of SAS.

After amplification, the PCR product was digested with BamHI and Asp 718 (Roche, Indianapolis, Ind.) and the resulting fragment cloned into the corresponding sites of the baculovirus transfer vector, pA2. Following DNA sequence confirmation, the plasmid (pA2-SAS) was transfected into Sf-9 cells to generate the recombinant baculovirus AcSAS as previously described (Coleman et al., *Gene* 190, 163–171 (1997)). Amplified virus was used to infect cells, and the gene product was radio-labeled with [$^{35}$S]-Met and [$^{35}$S]-Cys. Bands corresponding to the gene product were visualized by SDS-PAGE and autoradiography. Alternatively, the PCR product was used as a template for in vitro transcription and translation using rabbit reticulocyte lysate (Promega, Madison, Wis.) in the presence of [$^{35}$S]-Met. Translation products were resolved by SDS-PAGE and visualized by autoradiography.

For protein production, Sf-9 cells were seeded in serum-free media at a density of $1\times10^6$ cells/ml in spinner flasks and infected at a multiplicity of infection of 1-2 with the recombinant virus. A detergent fractionation procedure was employed (Miyamoto et al., *Mol. Cell. Biol.* 5, 2860–2865 (1985)) to separate nuclear from non-nuclear fractions. Protein was resolved by SDS-PAGE, transferred to a ProBlott™ membrane (ABI, Foster City, Calif.), and visualized by Ponceau S staining. A prominent band at the expected MW of ~40 kD was visible and excised for protein microsequencing using an ABI-494 sequencer (PE Biosystems, Foster City, Calif.).-

Neu5Ac/KDN Detection

Sialic acid was measured by the procedure of Hara et al. (*Anal. Biochem.* 179, 162–166 (1989). Ten microliters of sample were treated with 200 μl DMB (Sigma Chemicals, St. Louis, Mo.) solution (7.0 mM DMB in 1.4 M acetic acid, 0.75 M β-mercaptoethanol, and 18 mM sodium hydrosulfite) at 50° C. for 2.5 hrs, from which 10 μl was used for HPLC analysis on a Shimadzu (Columbia, Md.) VP series HPLC using a Waters (Milford, Mass.) Spherisorb 5 μm ODS2 column. Peaks were detected using a Shimadzu RF-10AXL fluorescence detector with 448 nm emission and 373 nm excitation wavelengths. The mobile phase was an acetonitrile, methanol, and water mixture (9:7:84, v/v) with a flow rate of 0.7 ml/min. Response factors of Neu5Ac and KDN were established with authentic standards based on peak areas for quantifying sample sialic acid levels. Sialic acid content was normalized based on protein content measured with the Pierce (Rockford, Ill.) BCA assay kit and a Molecular Devices (Sunnyvale, Calif.) microplate reader.

Cell Culture and Sialic Acid Quantification

Sf-9 (ATCC, Manassas, Va.) cells were grown in Ex-Cell™ 405 media (JRH BioScience, Lenexa, Kans.) with and without 10% FBS at 27° C. CHO-K1 cells (ATCC, Manassas, Va.) were cultured at 37° C. in a humidified atmosphere with 5% $CO_2$ in Dulbecco's Modified Eagle Medium (Life Technologies, Rockville, Md.) supplemented with 10% FBS, 100 U/ml penicillin, 100 µg/ml streptomycin, 100 µM MEM essential amino acids, and 4 mM L-glutamine (Life Technologies, Rockville, Md.). Cells were grown to confluency in T-75 flasks, washed twice with PBS, and lysed in 0.05 M bicine, pH 8.5, with 1 mM DTT (Vann et al., *Glycobiology* 7, 697–701 (1997)) using a Tekmar Sonic Disruptor (Cincinnati, Ohio). For determination of sialic acid content, 10 µl of lysates with and without 10,000 MWCO microfiltration (Millipore, Bedford, Mass.) were analyzed by DMB derivatization as described above.

Sugar substrate feeding was studied by plating approximately $10^6$ Sf-9 cells on each well of a six well plate. Media was replaced with 2 ml fresh media supplemented with 10 mM sterile-filtered Man, ManN, or ManNAc. Cells were left uninfected or infected with 20 µl of the appropriate (A35 or AcSAS) amplified baculovirus stock. Cells were harvested at 80 hours post infection by separating the pellet from the media by centrifugation and washing twice with PBS. Cells were lysed and analyzed for sialic acid content as described above.

In Vitro Activity

In vitro activity assays were based on the procedure of Angata et al. (*J. Biol. Chem.* 274, 22949–22956 (1999)). Lysates were prepared from A35 and AcSAS infected and uninfected Sf-9 cells cultured in T-75 flasks with and without 10 mM ManNAc supplementation. After washing twice with PBS, cells were lysed on ice with 25 strokes of a tight-fitting Dounce homogenizer (Wheaton, Millville, N.J.) in 2.5 ml lysis buffer [50 mM HEPES pH=7.0 with 1 mM DTT, leupeptin (1 µg/ml), antipain (0.5 µg/ml), benzamidine-HCl (15.6 µg/ml), aprotinin (0.5 µg/ml), chymostatin (0.5 µg/ml), and 1 mM phenylmethylsulfonylfluoride]. 5 µl of substrate solution was incubated with either 20 µl insect cell lysate (30 min.) or purified *E. coli* protein (60 min.) at 37° C. The substrate solution contained 10 mM $MnCl_2$, 20 mM PEP, and either 5 mM ManNAc-6-P or 25 mM Man-6-P (Sigma, St. Louis, Mo.). ManNAc-6-P was prepared by acid hydrolysis of meningococcal Group A polysaccharide. The polysaccharide (15.5 mg) in 5.8 ml water was mixed with 770 mg of Dowex 50 H+ and heated for 1 hr. at 100° C. The filtered hydrolysate was dried in vacuo and the residue dissolved to give a solution of 50 mM ManNAc-6-P and stored frozen. Substrate solutions containing 25 mM Man and ManNAc were also used. Boiled samples were used as negative controls. Following incubation, all samples were boiled 3 min., centrifuged for 10 min. at 12,000 g, and split into two 10 µl aliquots. One aliquot was treated with 9 units of calf intestine alkaline phosphatase (Roche, Indianapolis, Ind.) along with 3 µl of accompanying buffer while the other aliquot was diluted with water and buffer. AP treated aliquots were incubated 4 hrs. at 37° C., and 10 µl of both AP treated and untreated samples were reacted with DMB as described above. 2 µl of the samples incubated with insect lysates and 10 µl of the samples incubated with bacterial protein were injected onto the HPLC for sialic acid analysis as described above.

For substrate competition experiments, Man-6-P and ManNAc-6-P concentrations in the substrate solution were varied from 1 to 20 mM. In vitro assays were run with Sf-9 lysates as described above. Samples were treated with 7 µl buffer and 18 units of AP, incubated for 4 hrs. at 37° C., and analyzed for sialic acid content. Samples containing more than 1 mM ManNAc-6-P in the substrate solution produced high levels of sialic acid and were diluted 1:5 before injection to avoid fluorescence detector signal saturation.

Analysis with Aldolase Using HPAEC

Sf-9 cells were grown in T-75 flasks and then infected with A35 or AcSAS or left uninfected in the presence or absence of 10 mM ManNAc. After 80 hrs., cells were washed twice in PBS and sonicated. Aliquots (200 µl) were filtered through 10,000 MWCO membranes, and 50 µl samples were treated with 12.5 µl aldolase solution [0.0055 U aldolase (ICN, Costa Mesa, Calif.), 1.4 mM NADH (Sigma, St. Louis, Mo.), 0.5 M HEPES pH 7.5, 0.7 U lactate dehydrogenase (Roche, Indianapolis, Ind.)] or left untreated and incubated at 37° C. for one hour (Lilley et al., 1992). Samples were analyzed by HPAEC with a Dionex (Sunnyvale, Calif.) BioLC system using a pulsed amperometric detector (PAD-II) on a Carbopac PA-1 column. The initial elution composition was 50% A (200 mM NaOH), 45% B (water), and 5% C (1M NaOAc, 200 mM NaOH) with a linear gradient to 50% A, 25% B, and 25% C at 20 min. A 6 min. 50% A and 50% C washing followed. Samples were normalized based on protein content by dilution with water, and 20 µl of each sample were analyzed. Ten µl of each sample were also derivatized with DMB and analyzed by HPLC as described above to confirm the elimination of sialic acids by aldolase treatment.

Example 7

Characterization of CMP-SAS and Its Use with SAS in Engineering the Sialic Acid Metabolic Pathway Recombinant glycoproteins are increasingly used as therapeutic agents, and post-translational modifications to these proteins can significantly affect their properties and value. N-glycosylation is a particularly important modification that can affect solubility, biological activity, and in vivo circulatory half-life[1]. Mammalian cell lines produce glycoproteins with complex-type glycan patterns typically terminating in sialic acid residues. While insect cells N-glycosylate secretory and membrane proteins, the final N-glycosylation pattern includes mostly high mannose or paucimannosidic (low mannose) structures[2,3]. Some oligosaccharides terminating in N-acetylglucosamine or galactose have also been observed[2,3]. Expression of recombinant galactosyltransferases has increased the relative amounts of galactose terminating N-glycans[4-6]. The differences between mammalian and insect glycosylation can have a significant impact on a protein's characteristics. For example, the in vitro activity of recombinant human thyrotropin expressed in insect cells was five times higher than that produced by Chinese hamster ovary cells (CHO), yet the in vivo activity of CHO thyrotropin was higher in mice[7]. The reason for this difference in activity was thought to be a more rapid clearance of the insect produced thyrotropin due to the absence of terminal sialic acid residues[7].

The sialylation of glycoproteins requires the metabolic generation of the sugar nucleotide cytidine monophosphosialic acid (CMP-SA) followed by the transfer of the sialic acid to an acceptor oligosaccharide in the Golgi apparatus by sialyltransferases. Previous studies indicate that insect cells have undetectable levels of the most common sialic acid nucleotide, CMP-N-acetylneuraminic acid (CMP-Neu5Ac)[8] as well as negligible levels of its metabolic precursor, Neu5Ac[9]. Since CMP-Neu5Ac and Neu5Ac are not easily incorporated into cells[10], alternative strategies should be considered for generating sufficient Neu5Ac and CMP-Neu5Ac for sialylation in insect cells. One approach is to engineer the necessary enzymatic pathways for CMP-SA synthesis. Unlike Neu5Ac or CMP-Neu5Ac, the precursor to Neu5Ac, N-acetylmannosamine (ManNAc)[10], and its analogs[11,12] are readily incorporated into cells. In fact, feeding of ManNAc in concert with the expression of the recently cloned sialic acid phosphate synthase gene generated large intracellular pools of Neu5Ac in insect cells[9]. In the case of mammalian cells, Neu5Ac is subsequently activated to the nucleotide sugar CMP-Neu5Ac by CMP-sialic acid synthase[13]. While the activity of CMP-SAS has been described since 1962[14], the gene has only recently been cloned in E. coli[15] and mouse[16].

Using homology searches based on the E. coli sequence (neuA), the novel human Cmp-Sas gene of the present invention was identified and cloned it into a transfer vector to produce the recombinant baculovirus (AcCMP-SAS). In order to determine if insect cells could be modified to generate CMP-SA pools, Sf-9 cells were co-infected with AcCMP-SAS and the baculovirus containing the recombinant human sialic acid phosphate synthase (AcSAS) of the present invention in the presence of ManNAc. The result was the production of large pools of intracellular CMP-Neu5Ac, overcoming a major limitation to the sialylation of glycoproteins in insect cells. Interestingly, another sugar nucleotide, CMP-2-keto-3-deoxy-D-glycero-D-galactonononic acid (CMP-KDN), was generated in insect cells following infection with AcSAS and AcCMP-SAS when not supplemented by ManNAc. The ability to generate either CMP-Neu5Ac or CMP-KDN in separate cell cultures presents the potential for generating glycoproteins with different sialic acid termini in insect cells.

Experimental Protocol of Example 7
Gene Identification, Characterization, Cloning, and Expression The E. coli neuA coding sequence was used to query the Human Genome Sciences, Inc., (Rockville, Md.) human cDNA database with BLAST software. One EST clone from a human prostate cell line demonstrated significant homology to neuA and was further characterized. The procedures used for Northern blotting, in vitro transcription and translation, and baculovirus cloning were the same as those described for work with ASA9. For PCR amplification, the forward primer, 5'-<u>TGTAATACGACTCACTATAGGGC</u>GGATCCGCCATCATGGACTCGGTGGAGAA GG, (SEQ ID NO: 15) contained a synthetic T7 promoter sequence (underlined), a BamHI site (italics), a KOZAK sequence (bold) and a sequence corresponding to the first six codons of Cmp-Sas. The reverse primer, 5'-GTACGGTACCTT ACTATTTTGGCSATGASATTATTAACTTTTTCC, (SEQ ID NO: 16) contained an Asp 718 site (italics), two in-frame stop codons (bold), and sequence representing the last six codons of Cmp-Sas.

Enzyme Localization

Protein localization was determined with the Pierce NE-PER™ kit and modifications of a previously published procedure[19]. T-175 flasks were plated with 16×10⁶ Sf-9 cells, and the media was replaced. Two flasks of cells were infected with A35, AcSAS, or AcCMP-SAS amplified viruses for approximately 60 h. Cells were washed twice with PBS and incubated in 3 ml of the described hypotonic buffer[19]. After centrifugation, 400 $\mu$l of stripping solution (10 mM Tris HCl pH 7.3, 1% NP-40, 0.5% deoxycholate, 10 mM NaCl, 1.5 mM $MgCl_2$) was added to the pellet. The supernatant was removed and the soluble nuclear fraction taken after incubation with 200 $\mu$l of the described lysis buffer[19]. The protein content of all fractions was determined using the Pierce (Rockford, Ill.) BCA assay kit with a Molecular Devices (Sunnyvale, Calif.) 96-well plate reader. Total protein from each fraction were analyzed by 12.5% SDS-PAGE. Samples were transferred to a PVDF membrane, stained with Ponceau S, appropriate bands excised, and submitted for N-terminal protein sequencing using an ABI-494 sequencer (PE Biosystems, Foster City, Calif.).

CMP-Sialic Acid Synthase Assay

To assay CMP-sialic acid synthetic ability, CHO-K1 cells (ATCC, Manassas, Va.) were grown to confluence in T-75 flasks at 37° C. in a humidified atmosphere with 5% $CO_2$ in Dulbecco's Modified Eagle medium (Life Technologies, Rockville, Md.) supplemented with 10% FBS, 100 U/ml penicillin, 100 $\mu$g/ml streptomycin, 100 $\mu$M MEM essential amino acids, and 4 mM L-glutamine (Life Technologies, Rockville, Md.). After washing with PBS, 1 ml of suspension solution (02.M Tris, 0.15M NaCl, 1% NP-40 pH=9.0)[27] was added. Sf-9 cells were plated in 6-well dishes with fresh Ex-Cell 405 media (JRH Biosciences, Lanexa, Kans.) and infected with the A35 control virus or AcCMP-SAS virus or left uninfected for 60 h. The cells were washed with PBS, and the contents of two wells were harvested with 400 $\mu$l of the resuspension solution in each well. The resulting mixtures were centrifuged 15 min at 14,000 RPM, and the supernatant was used for enzyme assays. The protein content of each sample was determined as previously described. The activity assays were modified from the TBA assay used to measure CMP-SA formation[17]. Twenty $\mu$l of lysates were incubated with 100 $\mu$l of substrate solution[17] at 37° C. for 40 min. Forty $\mu$l of 1.6 M $NaBH_4$ was used to reduce free Neu5Ac, and the mixture was then treated with 40 $\mu$l of 20 N $H_3PO_4$. Released Neu5Ac was oxidized with 0.1 ml 25 mM periodic acid for 30 min at 37° C. then treated with 0.1 ml of 62 mM sodium bisulfite. 1.0 ml of 0.1 M TBA was added, and the mixture was placed in a boiling water bath for 7.5 minutes. The tubes were placed on ice and 2 ml of DMSO with 5% concentrated HCl was added. The absorbance at 552 nm was taken using a Spectronic 20 spectrophotometer (Bausch and Lomb, Rochester, N.Y.), and the amount of CMP-Neu5Ac formed calculated by Neu5Ac standards.

CMP-Sialic Acid Levels

Sf-9 cells were grown in 6-well plates and infected with combinations of A35, AcSAS, and AcCMP-SAS viruses along with 10 mM ManNAc feeding for approximately 90 hr. CHO cells grown according to the culture conditions described above were grown in T-75 flasks with and without 10 mM ManNAc supplementation for 48 hr. All cells were washed with PBS and aliquots taken for protein quantification. Cells were resuspended in 75% ethanol and sonicated on ice for 30 s. Lysates were centrifuged, frozen in liquid nitrogen, and lyophilized. Samples were resuspended in 120 $\mu$l of 40 mM phosphate buffer, pH 9.2, to stabilize CMP-sialic acids. Samples were centrifuged again and the supernatant filtered through 10,000 molecular weight cut-off membranes. CMP-sialic acids were detected using HPAEC (Tomiya, in preparation) and quantified versus the response curves of standard CMP-Neu5Ac (Sigma, St. Louis, Mo.) and CMP-KDN (Yasuhiro Kajihara, Yokohama City University, Japan).

Results of Example 7
Gene Identification

The human CMP-sialic acid synthase gene was identified using homology searches based on the known bacterial CMP-sialic acid synthase gene[15]. Over the entire sequences, the putative human gene is 23% identical and 47% similar to the bacterial sequence and 92% identical and 94% similar to the murine sequence. Northern blots probing human mRNA samples using the gene sequence showed ubiquitous transcription of the gene in all human tissues tested.

Using in vitro transcription and translation, the putative gene was shown to encode a protein of the expected molecular weight. The same gene was used to generate AcCMP-SAS, and this virus was used to infect Sf-9 cells. Pulse labeling followed by SDS-PAGE separation showed a protein of 49 kDa, consistent with the predicted weight of 48.5 kDa, that was not observed in the control infection (A35).

CMP-Sialic Acid Synthase Activity

The function of the putative gene product was determined in vitro using cell lysates incubated with the precursors N-acetylneuraminic acid and cytidine triphosphate based on the published thiobarbituric acid (TBA) assay[17]. CMP-SA synthetic ability is observed only in Sf-9 cells following AcCMP-SAS infection and was not detectable in control infected or uninfected cells. Furthermore, infection with the AcCMP-SAS provides 60 times the activity of the native CMP-SA synthetic ability of CHO cells.

Enzyme Localization

CMP-sialic acid synthetic activity in mammals has been shown to localize to the nucleus[13], and fluorescent labeling of the recombinant murine enzyme expressed in 3T3 cells confirmed this localization[16]. Analysis of the human CMP-SAS sequence with the pSORT algorithm also predicted the protein would localize to the nucleus because of the nuclear localization sequence (KRPR) starting at amino acid 199. To determine if the recombinant human enzyme localized to the nucleus of insect cells, a nuclear separation using the Pierce NE-PER™ kit was performed. A protein band from the AcCMP-SAS infection was found predominantly in the nuclear fraction but not in the nuclear fraction of a control infection. In contrast, recombinant SAS localized in the cytoplasmic fraction and not the nuclear fraction as observed previously for the native enzyme in mammalian cells[18]. TBA assays of the nuclear fraction showed CMP-SAS activity of AcCMP-SAS infected but not AcSAS infected cells. The protein band in the nuclear fraction following a detergent separation[19] was also transferred to a PDF membrane for N-terminal protein sequencing. The sequence was identical to amino acids 29 through 33 as predicted from the gene sequence indicating cleavage of the first 28 amino acids of the nuclear localized protein.

Completion of the CMP-Sialic Acid Pathway in Insect Cells

The production of Neu5Ac in insect cells has been accomplished by infection with the recombinant human sialic acid phosphate synthase virus (AcSAS) in concert with feeding of the precursor ManNAc[9]. Coinfection of AcSAS and AcCMP-SAS with concomitant ManNAc feeding was attempted in order to produce and activate sialic acids in insect cells. Proteins of the expected molecular weights and cellular locations are seen in lysates of cells infected with each virus individually and together.

A procedure was developed to measure CMP-Neu5Ac by high performance anion exchange chromatography (HPAEC) using UV monitoring. Using this technique, samples from different infection strategies were examined, and the levels of CMP-Neu5Ac produced on a protein basis are listed in Table 5, below. In agreement with previous work[10], CHO cells are shown to have measurable CMP-Neu5Ac levels which are augmented upon feeding of 10 mM ManNAc. Uninfected Sf-9 cells grown in serum-free medium do not have detectable CMP-Neu5Ac levels with or without ManNAc feeding. Large CMP-Neu5Ac levels are produced in insect cells only when all three components of the sialic acid pathway are present: the precursor sugar ManNAc, the sialic acid phosphate synthase from AcSAS, and the CMP-sialic acid synthase from AcCMP-SAS. In this case, CMP-Neu5Ac levels are approximately 6 times those seen in CHO with ManNAc feeding and 30 times without ManNAc feeding.

When ManNAc feeding is omitted from an AcSAS and AcCMP-SAS infection, a CMP-Neu5Ac peak is not observed but a peak eluting at 8.5 min. is detected. This peak has the same elution time as authentic CMP-KDN and is found in quantities of 4 pmol/μg protein. Further confirmation of the peak as CMP-KDN was obtained by acid hydrolysis of the eluted peak followed by fluorescent labeling with DMB and HPLC separation. The resulting fluorescent compound eluted at the same elution time as authentic KDN (data not shown).

Table 5. Intracellular CMP-Neu5Ac levels of CHO and Sf-9 cells using the indicated feeding strategy and infection scheme. The CMP-Neu5Ac content of cell lysates was determined by HPAEC.

| Sample | CMP-NeuAc5 pmol/μg protein) |
|---|---|
| CHO | 0.30 |
| CHO + ManNAc | 1.77 |
| Sf-9 | <0.02 |
| Sf-9 + ManNAc | <0.02 |
| Sf-9 + A35 + ManNAc | 0.02 |
| Sf-9 + AcSAS + ManNAc | 0.02 |
| Sf-9 + AcCMP-SAS + ManNAc | 0.10 |
| Sf-9 + A35 + AcSAS | <0.02 |
| Sf-9 + A35 + AcCMP-SAS | <0.02 |
| Sf-9 + AcSAS + AcCMP-SAS | <0.02 |
| Sf-9 + A35 + AcSAS + ManNAc | 0.08 |
| Sf-9 + A35 + AcCMP-SAS + ManNAc | 0.04 |
| Sf-9 + AcCMP-SAS + AcSAS + ManNAc | 10.30 |

Discussion of Example 7

The baculovirus expression system offers several advantages including the capacity to generate significant levels of post-translationally modified recombinant proteins in a eucaryotic cell line. However, one of the drawbacks of recombinant baculovirus expression is its inability to produce glycoproteins with sizable fractions having complex-type N-glycans, especially those terminating in sialic acid residues. Sialic acids have been associated with numerous in vivo biological processes including development[20], pathogen infectivity[21], ligand-receptor interactions[21], cancer metastasis[22], and the elimination of non-sialylated glycoproteins by the asialoglycoprotein receptor[7].

Although Sf-9 cells do not contain detectable native pools of CMP-Neu5Ac, this bottleneck to sialylation has been overcome by substrate feeding and engineering the CMP-SA synthesis genes into insect cells. The human CMP-sialic acid synthase gene has been identified and expressed in an active form in insect cells. The enzyme localizes to the nucleus of insect cells as observed in the native mammalian host to suggest that the encoded nuclear localization signals are functional in insect cells as well. Moreover, the protein isolated from the nuclear fraction retains enzyme activity, but interestingly its first 28 amino acids are truncated as determined by N-terminal protein sequencing analysis. This cleavage may explain the lower molecular weight of the protein band observed in the nuclear fraction of the Coomassie stained gel as compared to the radiolabeled protein in the total cell lysate. The cause of the cleavage of the nuclear localized CMP-SA synthase is unknown as is the relevance of this cleavage to the nuclear localization process in insect cells.

By feeding ManNAc along with expression of CMP-SAS and SAS, CMP-Neu5Ac levels more than five times higher than those observed in ManNAc supplemented CHO cells are achieved in Sf-9 cells. Some low level endogenous sialic acid metabolic activity may be present in insect cells as seen with the addition of ManNAc and just one component of the pathway (Table 5). However, CMP-levels are increased more than 100-fold by the addition of all three components. In order to complete sialylation, the CMP-Neu5Ac must be transported into the Golgi where a sialyltransferase can transfer the Neu5Ac to the target acceptor oligosaccharide. Expression of recombinant sialyltransferases and a CMP-sialic acid transporter may also be required to achieve sialylation in insect cell culture.

Interestingly, an alternative nucleotide sugar, CMP-KDN, is produced in insect cells co-expressing CMP-SAS and SAS without ManNAc feeding. Previously, we observed the production of KDN when insect cells expressed SAS in the absence of ManNAc. Therefore, both SAS and CMP-SAS must recognize the substrates for generating deaminated sialic acid forms. More significant is the observation that the CMP-KDN is generated in the absence of detectable levels of CMP-Neu5Ac. This is the first report of a cellular system that can produce substantial levels of activated KDN without activated Neu5Ac. Since at least one sialyltransferase recognizes both CMP-KDN as well as CMP-Neu5Ac[23], this expression system may eventually allow the exclusive KDNylation of glycoproteins. KDN was first identified in 1986[24], and its effects on function and activity of a sialylated glycoprotein are largely unknown. However, elevated KDN:Neu5Ac levels have been observed in tissues during biological phenomena of great interest such as cancer and development[25]. In addition glycoproteins sialylated by KDN rather than Neu5Ac may be less susceptible to sialidases[24]. Such proteins could have longer in vivo circulatory half-lives and potentially greater pharmaceutical value.

Furthermore, the capacity to enhance sialylation by engineering the CMP-SA pathway may have significance beyond the baculovirus expression system. Reports have suggested that limitations in levels of activated sialic acids may exist in mammalian cell lines as well[26]. Other expression systems such as yeast and plant cells may also lack some of the genes involved in generating CMP-SA so the pathway may be engineered into other recombinant hosts. In these cases, the sialyltransferases and the enzymes involved in sugar nucleotide transport may also be needed. Thus, in accordance with the invention, the number of cellular species that can generate complex "mammalian-like" glycoforms during recombinant protein expression may be increased through the metabolic engineering of the CMP-SA synthetic and transfer pathways.

Conclusion of Example 7

In summary, to increase substrate levels, the enzymes of the metabolic pathway for CMP-SA synthesis have been engineered into insect cells using the baculovirus expression system. A novel human CMP-sialic acid synthase gene (Cmp-Sas) was identified based on homology to the corresponding *E. coli* gene. The enzyme is ubiquitously expressed in human cells and is active in baculovirus-infected insect cells where it localizes to the nucleus as it does in mammalian cells. Co-expression of Cmp-Sas with the novel sialic acid phosphate synthase (SAS) of the present invention in concert with N-acetylmannosamine (ManNAc) feeding yields intracellular CMP-Neu5Ac levels 30 times higher than those observed in unsupplemented CHO cells. The absence of any one of these three components abolishes CMP-Neu5Ac production in vivo. However, when ManNAc feeding is omitted, the sugar nucleotide form of deaminated Neu5Ac, CMP-2-keto-3-deoxy-D-glycero-D-galacto-nononic acid (CMP-KDN), is produced instead indicating that alternative sialic acid glycoforms may eventually be possible in insect cells. Engineering the CMP-SA metabolic pathway may be beneficial in various cell lines in which CMP-Neu5Ac production limits sialylation of glycoproteins or other glycans.

References Cited In Example 7

1. Goochee, C. F., Gramer, M. J., Andersen, D. C., Bahr, J. B. & Rasmussen, J. R. The oligosaccharides of glycoproteins: bioprocess factors affecting oligosaccharide structure and their effect on glycoprotein properties. *Bio/Technology* 9, 1347–1355 (1991).
2. Altmann, F., Staudacher, E., Wilson, I. B. & Marz, L. Insect cells as hosts for the expression of recombinant glycoproteins. *Glycoconj. J.* 16, 109–123 (1999).
3. Hsu, T. A. et al. Differential N-glycan patterns of secreted and intracellular IgG produced in *Trichoplusia ni* cells. *J. Biol. Chem.* 272, 9062–9070 (1997).
4. Jarvis, D. L. & Finn, E. E. Modifying the insect cell N-glycosylation pathway with immediate early baculovirus expression vectors. *Nat. Biotechnol.* 10, 1288–1292 (1996).
5. Hollister, J. R., Shaper, J. H. & Jarvis, D. L. Stable expression of mammalian beta 1,4-galactosyltransferase extends the N-glycosylation pathway in insect cells. *Glycobiology.* 8, 473–480 (1998).
6. Ailor, E. A. et al. N-Glycan patterns of human transferrin produced in *Trichoplusia ni* insect cells: effects of mammalian galactosyltransferases. *Glycobiology,* (in press).
7. Grossmann, M. et al. Expression of biologically active human thyrotropin (hTSH) in a baculovirus system: effect of insect cell glycosylation on hTSH activity in vitro and in vivo. *Endocrinology* 138, 92–100 (1997).
8. Hooker, A. D. et al. Constraints on the transport and glycosylation of recombinant IFN-gamma in Chinese hamster ovary and insect cells. *Biotechnol. Bioeng.* 63, 559–572 (1999).
9. Lawrence, S. M. et al. Cloning and expression of the human N-acetylneuraminic acid phosphate synthase gene with 2-keto-3-deoxy-D-glycero-D-galacto-nononic acid biosynthetic ability. *J. Biol. Chem.* 275, 17869–17877 (2000).
10. Gu, X. & Wang, D. I. Improvement of interferon-gamma sialylation in Chinese hamster ovary cell culture by feeding of N-acetylmannosamine. *Biotechnol. Bioeng.* 58, 642–648 (1998).
11. Mahal, L. K., Yarema, K. J., Lemieux, G. A. & Bertozzi, C. R. Chemical approaches to glycobiology: engineering cell surface sialic acids for tumor targeting, in *Sialobiology and Other Novel Forms of Glycosylation* (eds. Inoue, Y., Lee, Y. C. & Troy, F. A.) 273–280 (Gakushin Publishing, Osaka, Japan, 1999).
12. Reutter, W. et al. Biochemical engineering by new N-acetylmannosamines of sialic acid creates new biological characteristics and technical tools of its N-acyl side chain. in *Sialobiology and Other Novel Forms of Glycosylation* (eds. Inoue, Y., Lee, Y. C. & Troy, F. A.) 281–288 (Gakushin Publishing, Osaka, Japan, 1999).
13. Kean, E. L. Sialic acid activation. *Glycobiology* 1, 441–447 (1991).
14. Roseman, S. Enzymatic synthesis of cytidine 5'-monophospho-sialic acids. *Proc. Natl. Acad. Sci. USA* 48, 437–441 (1962).

15. Zapata, G., Vann, W. F., Aaronson, W., Lewis, M. S. & Moos, M. Sequence of the cloned *Escherichia coli* K1 CMP-N-acetylneuraminic acid synthetase gene. *J. Biol. Chem.* 264, 14769–14774 (1989).
16. Munster, A. K. et al. Mammalian cytidine 5'-monophosphate N-acetylneuraminic acid synthetase: a nuclear protein with evolutionarily conserved structural motifs. *Proc. Natl. Acad. Sci. USA* 95, 9140–9145 (1998).
17. Vann, W. F. et al. Purification, properties, and genetic location of *Escherichia coli* cytidine 5'-monophosphate N-acetylneuraminic acid synthetase. *J. Biol. Chem.* 262, 17556–17562 (1987).
18. Van Rinsum, J., Van Dijk, W., Hooghwinkel, G. J. & Ferwerda, W. Subcellular localization and tissue distribution of sialic acid-forming enzymes. N-acetylneuraminate-9-phosphate synthase and N-acetylneuraminate 9-phosphatase. *Biochem. J.* 223, 323–328 (1984).
19. Miyamoto, C. et al. Production of human c-myc protein in insect cells infected with a baculovirus expression vector. *Mol. Cell Biol.* 5, 2860–2865 (1985).
20. Cunningham, B. A., Hoffman, S., Rutishauser, U., Hemperly, J. J. & Edelman, G. M. Molecular topography of the neural cell adhesion molecule N-CAM: surface orientation and location of sialic acid-rich and binding regions. *Proc. Natl. Acad. Sci. USA* 80, 3116–3120 (1983).
21. Schauer, R., Kelm, S., Reuter, G., Roggentin, P. & Shaw, L. Biochemistry and role of sialic acids. in *Biology of the Sialic Acids* (ed. Rosenberg, A.) 7–67 (Plenum Press, New York, 1995).
22. Fukuda, M. Possible roles of tumor-associated carbohydrate antigens. *Cancer Res.* 56, 2237–2244 (1996).
23. Angata, T., Matsuda, T. & Kitajima, K. Synthesis of neoglycoconjugates containing deaminated neuraminic acid (KDN) using rat liver α2,6-sialyltransferase. *Glycobiology* 8, 277–284 (1998).
24. Nadano, D. et al. A naturally occurring deaminated neuraminic acid, 3-deoxy-D-glycero-D-galacto-nonulosonic acid (KDN): its unique occurrence at the nonreducing ends of oligosialyl chains in polysialoglycoprotein of rainbow trout eggs. *J. Biol. Chem.* 261, 11550–11557 (1986).
25. Inoue, S. et al. Identification of free deaminated sialic acid (2-keto-3-deoxy-D-glycero-D-galacto-nononic acid) in human red blood cells and its elevated expression in fetal cord red blood cells and ovarian cancer cells. *J. Biol. Chem.* 273, 27199–27204 (1998).
26. Pels Rijcken, W. R., Overdijk, B., Van den Eijnden, D. H. & Ferwerda, W. The effect of increasing nucleotide-sugar concentrations on the incorporation of sugars into glycoconjugates in rat hepatocytes. *Biochem. J.* 305, 865–870 (1995).
27. Potvin, B., Raju, S. R. & Stanley, P. lec32 is a new mutation in Chinese Hamster Ovary cells that essentially abrogates CMP-N-acetylneuraminic acid synthetase activity. *J. Biol. Chem.* 270, 30415–30421 (1995).

The entire disclosure of all publications (including patents, patent applications, journal articles, laboratory manuals, books, or other documents) cited herein are hereby incorporated by reference in their entireties.

Further, the Sequence Listing submitted herewith is hereby incorporated by reference in its entirety. Additionally, the specification and sequence listings of U.S. Provisional Applications Nos. 60/227,579; 60/169,624; and 60/122,582 and of U.S. application Ser. No. 09/516,793 are all hereby incorporated by reference in their entireties.

What is claimed is:

1. An isolated or purified cell which is recombinant or genetically modified to contain and co-express
   i) a cytidine monophosphate sialic acid (CMP-SA)-synthase gene wherein said CMP-SA synthase gene encodes a polypeptide that catalyzes the formation of CMP-SA from SA and cytidine triphosphate (CTP), and wherein said polypeptide is
      a) a polypeptide represented by SEQ ID NO:4 or
      b) a variant polypeptide thereof that contains conservative amino acid substitutions and in which CMP-SA-synthase structure and function are conserved, and
   ii) a sialic acid phosphate synthase (SAS) gene wherein said SAS gene encodes a polypeptide that catalyzes the formation of sialic acid phosphate from N-acetylmannosamine (ManNAc) and phosphoeylpyruvate (PEP), and wherein said polypeptide is
   a) a polypeptide represented by SEQ ID NO: 6 or a variant polypeptide thereof that contains conservative amino acid substitutions and in which SAS structure and function are conserved, or
   b) a polypeptide represented by SEQ ID NO: 8 or a variant polypeptide thereof that contains conservative amino acid substitutions and in which SAS structure and function are conserved, and
   wherein said cell is capable of producing donor substrate CMP-SA above levels produced before said cell was made recombinant or genetically modified, when provided ManNAc.

2. The isolated or purified cell of claim 2, which is an insect cell.

3. The insect cell of claim 2, wherein said insect cell is of a species selected from the group consisting of:
   (a) *Spodoptera frugiperda*;
   (b) *Trichoplusia ni*;
   (c) *Estigmena acrea*; and,
   (d) *Drosophila*.

4. The isolated or purified cell of claim 1, which is a yeast cell.

5. The isolated or purified cell of claim 1, which is a plant cell.

6. The isolated or purified cell of claim 1, which is a bacterial cell.

7. The isolated or purified cell of claim 1, which is a fungal cell.

8. The isolated or purified cell of claim 1, wherein said cell is a mammalian cell.

9. The isolated or purified cell of claim 1, wherein the donor substrate CMP-SA is CMP-Neu5Ac (cytidine monophosphate-N-acetylneuraminic acid).

10. The isolated or purified cell of claim 1 wherein said cell is provided with ManNAc by addition of ManNAc to media in which said cell is grown.

11. The isolated or purified cell of claim 1 wherein said cell is provided with ManNAc by genetically engineering said cell to catalyze synthesis of ManNAc.

12. The isolated or purified cell of claim 1, wherein said cell is genetically engineered to contain or express an epimerase that synthesizes ManNAc.

13. The isolated or purified cell of claim 12, wherein said epimerase is UDP-GlcNAc-2 epimerase.

14. The isolated or purified cell of claim 12, wherein said epimerase is GlcNAc-2 epimerase.

15. The isolated or purified cell of claim 1, wherein said CMP-sialic acid synthase gene and said sialic acid phosphate synthase gene are isolated from a human source.

16. An isolated or purified cell which is recombinant or genetically modified to contain or co-express
   i) a cytidine monophosphate-sialic acid (CMP-SA) synthase gene, wherein said CMP-SA synthase gene encodes a polypeptide that catalyzes the formation of CMP-SA from SA and cytidine triphosphate (CTP), and wherein said CMP-SA synthase gene comprises
      a) a nucleotide sequence represented by SEQ ID NO: 3, or
      b) a polynucleotide that hybridizes to the nucleotide sequence represented by SEQ ID NO:3 under stringent conditions, and
   ii) a sialic acid phosphate synthase (SAS) gene wherein said SAS gene encodes a polypeptide that catalyzes the formation of sialic acid phosphate from N-acetylmannosamine (ManNAc) and phosphoeylpyruvate (PEP), and wherein said SAS gene comprises
      a) a nucleotide sequence represented by SEQ ID NO: 5, or
      b) a polynucleotide that hybridizes to the nucleotide sequence represented by SEQ ID NO:5 under stringent conditions,
   and wherein said cell is capable of producing donor substrate CMP-SA above levels produced before said cell was made recombinant or genetically modified, when provided with ManNAc.

17. The isolated or purified cell of claim 16, which is an insect cell.

18. The insect cell of claim 17, wherein said insect cell is of a species selected from the group consisting of:
   (a) *Spodoptera frugiperda;*
   (b) *Trichoplusia ni;*
   (c) *Estigmena acrea;* and,
   (d) *Drosophila.*

19. The isolated or purified cell of claim 16, which is a yeast cell.

20. The isolated or purified cell of claim 16, which is a plant cell.

21. The isolated or purified cell of claim 16, which is a bacterial cell.

22. The isolated or purified cell of claim 16, which is a fungal cell.

23. The isolated or purified cell of claim 16, wherein said cell is a mammalian cell.

24. The isolated or purified cell of claim 16, wherein the donor substrate CMP-SA is CMP-Neu5Ac (cytidine monophosphate-N-acetylneuraminic acid).

25. The isolated or purified cell of claim 16 wherein said cell is provided with ManNAc by addition of ManNAc to media in which said cell is grown.

26. The isolated or purified cell of claim 16 wherein said cell is provided with ManNAc by genetically engineering said cell to catalyze synthesis of ManNAc.

27. The isolated or purified cell of claim 26, wherein said cell is genetically engineered to contain or express an epimerase that synthesizes ManNAc.

28. The isolated or purified cell of claim 27, wherein said epimerase is UDP-GlcNAc-2 epimerase.

29. The isolated or purified cell of claim 27, wherein said epimerase is GlcNAc-2 epimerase.

30. The isolated or purified cell of claim 16, wherein said CMP-sialic acid synthase gene and said sialic acid phosphate synthase gene are isolated from a human source.

31. An isolated or purified cell that is recombinant or genetically modified to contain and co-express
   i) a cytidine monophosphate-sialic acid (CMP-SA) synthase gene, wherein said CMP-SA synthase gene encodes a polypeptide that catalyzes the formation of CMP-SA from SA and cytidine triphosphate (CTP), and wherein said polypeptide is
      a) a polypeptide represented by SEQ ID NO:4 or
      b) a variant of the polypeptide represented by SEQ ID NO:4 that contains conservative amino acid substitutions and in which CMP-SA structure and function are conserved; and
   ii) a sialic acid phosphate synthase (SAS) gene, wherein said SAS gene encodes a polypeptide that catalyzes the formation of sialic acid phosphate from N-acetylmannosamine (ManNAc) and phosphoeylpyruvate (PEP), and wherein said polypeptide is
      a) a polypeptide represented by SEQ ID NO: 6; or
      b) a variant of the polypeptide represented by SEQ ID NO:6 that contains conservative amino acid substitutions and in which SAS structure and function are conserved; or
      c) a polypeptide represented by SEQ ID NO: 8; or
      d) a variant of the polypeptide represented by SEQ ID NO: 8 that contains conservative amino acid substitutions and in which SAS structure and function are conserved,
   said cell producing the donor substrate CMP-SA above a level produced before said cell was made recombinant or genetically modified, wherein the donor substrate CMP-SA is CMP-KDN (cytidine monophosphate-2-keto-3-deoxy-D-glycero-D-galacto-nonoic acid).

32. The isolated or purified cell of claim 31, which is an insect cell.

33. The insect cell of claim 32, wherein said insect cell is of a species selected from the group consisting of:
   (a) *Spodoptera frugiperda;*
   (b) *Trichoplusia ni;*
   (c) *Estigmena acrea;* and,
   (d) *Drosophila.*

34. The isolated or purified cell of claim 31, which is a yeast cell.

35. The isolated or purified cell of claim 31, which is a plant cell.

36. The isolated or purified cell in claim 31, which is a bacterial cell.

37. The isolated or purified cell of claim 31, which is a fungal cell.

38. The isolated or purified cell of claim 31, which is a mammalian cell.

39. The isolated or purified cell of claim 31, wherein said CMP-sialic acid synthase gene and said sialic acid phosphate synthase gene are isolated from a human source.

40. An isolated or purified cell that is recombinant or genetically modified to contain and co-express
   i) a cytidine monophosphate-sialic acid (CMP-SA) synthase gene, wherein said CMP-SA-synthase gene encodes a polypeptide that catalyzes the formation of CMP-SA from SA and cytidine triphosphate (CTP), and wherein said CMP-SA synthase gene comprises
      a) a nucleotide sequence represented by SEQ ID NO: 3, or
      b) a polynucleotide that hybridizes to the nucleotide sequence represented by SEQ ID NO:3 under stringent conditions, and ii) a sialic acid phosphate synthase gene wherein said SAS gene encodes a polypeptide that catalyzes the formation of sialic acid phosphate from N-acetylmannosamine (ManNAc) and phosphoeylpyruvate (PEP), and wherein said SAS gene comprises
  a) a nucleotide sequence represented by SEQ ID NO: 5, or
  b) a polynucleotide that hybridizes to the nucleotide sequence represented by SEQ ID NO:5 under stringent conditions,
said cell producing the donor substrate CMP-SA above a level produced before said cell was made recombinant or genetically modified, wherein the donor substrate CMP-SA is CMP-KDN (cytidine monophosphate-2-keto-3-deoxy-D-glycero-D-galacto-nonoic acid).

41. The isolated or purified cell of claim 40, which is an insect cell.

42. The insect cell of claim 41, wherein said insect cell is of a species selected from the group consisting of:
  (a) *Spodoptera frugiperda*;
  (b) *Trichoplusia ni*;
  (c) *Estigmena acrea*; and,
  (d) *Drosophila*.

43. The isolated or purified cell of claim 40, which is a yeast cell.

44. The isolated or purified cell of claim 40, which is a plant cell.

45. The isolated or purified cell of claim 40, which is a bacterial cell.

46. The isolated or purified cell of claim 40, which is a fungal cell.

47. The isolated or purified cell of claim 40, which is a mammalian cell.

48. The isolated or purified cell of claim 40, wherein said CMP-sialic acid synthase gene and said sialic acid phosphate synthase gene are isolated from a human source.

49. An isolated or purified cell from a recombinant or genetically engineered cell line which contains and co-expresses
  i) a cytidine monophosphate-sialic acid (CMP-SA) synthase gene, wherein said CMP-SA-synthase gene encodes a polypeptide that catalyzes the formation of CMP-SA from SA and cytidine triphosphate (CTP), and wherein said polypeptide is
    a) a polypeptide represented by SEQ ID NO:4 or
    b) a variant of the polypeptide represented by SEQ ID NO:4 that contains conservative amino acid substitutions and in which CMP-SA structure and function are conserved; and
  ii) a sialic acid phosphate synthase (SAS) gene, wherein said SAS gene encodes a polypeptide that catalyzes the formation of sialic acid phosphate from N-acetylmannosamine (ManNAc) and phosphoeylpyruvate (PEP), and wherein said polypeptide is
    a) a polypeptide represented by SEQ ID NO: 6; or
    b) a variant of the polypeptide represented by SEQ ID NO:6 that contains conservative amino acid substitutions and in which SAS structure and function are conserved; or
    c) a polypeptide represented by SEQ ID NO: 8; or
    d) a variant of the polypeptide represented by SEQ ID NO: 8 that contains conservative amino acid substitutions and in which SAS structure and function are conserved,
said cell producing a donor substrate CMP-SA at a higher level than a cell from a parent cell line corresponding to said recombinant or genetically engineered cell line, when provided with ManNAc.

50. The isolated or purified cell of claim 49, which is an insect cell.

51. The insect cell of claim 50, wherein said insect cell is of a species selected from the group consisting of:
  (a) *Spodoptera frugiperda*;
  (b) *Trichoplusia ni*;
  (c) *Estigmena acrea*; and,
  (d) *Drosophila*.

52. The isolated or purified cell of claim 49, which is a yeast cell.

53. The isolated or purified cell of claim 49, which is a plant cell.

54. The isolated or purified cell of claim 49, which is a bacterial cell.

55. The isolated or purified cell of claim 49, which is a fungal cell.

56. The isolated or purified cell of claim 49, which is a mammalian cell.

57. The isolated or purified cell of claim 49, wherein the donor substrate CMP-SA is CMP-Neu5Ac (cytidine monophosphate-N-acetylneuraminic acid).

58. The isolated or purified cell of claim 49 wherein said CMP-sialic acid synthase gene and said sialic acid phosphate synthase gene are isolated from a human source.

59. The cell of claim 49 wherein said cell is provided with ManNAc by addition of ManNAc to media in which said cell is grown.

60. The cell of claim 49 wherein said cell is provided with ManNAc by genetically engineering said cell to catalyze synthesis of ManNAc.

61. The cell of claim 60, wherein said cell is genetically engineered to contain or express an epimerase that synthesizes ManNAc.

62. The cell of claim 61, wherein said epimerase is UDP-GlcNAc-2 epimerase.

63. The cell of claim 61, wherein said epimerase is GlcNAc-2 epimerase.

64. The cell of claim 49 wherein said cell also contains SA precursor GlcNAc above endogenous levels as a result of supplementation of cell growth medium with SA precursor GlcNAc.

65. An isolated or purified cell from a recombinant or genetically engineered cell line which contains and co-expresses
  i) a cytidine monophosphate-sialic acid (CMP-SA)-synthase gene, wherein said CMP-SA-synthase gene encodes a polypeptide that catalyzes the formation of CMP-SA from SA and cytidine triphosphate (CTP), and wherein said CMP-SA synthase gene comprises
    a) a nucleotide sequence represented by SEQ ID NO: 3, or
    b) a polynucleotide that hybridizes to the nucleotide sequence represented by SEQ ID NO:3 under stringent conditions, and
  ii) a sialic acid phosphate synthase gene wherein said SAS gene encodes a polypeptide that catalyzes the formation of sialic acid phosphate from N-acetylmannosamine (ManNAc) and phosphoeylpyruvate (PEP), and wherein said sialic acid phosphate synthase gene comprises
    a) a nucleotide sequence represented by SEQ ID NO: 5, or
    b) a polynucleotide that hybridizes to the nucleotide sequence represented by SEQ ID NO:5 under stringent conditions, said cell producing a donor substrate CMP-SA at a higher level than a cell from a parent cell line corresponding to said recombinant or genetically engineered cell line, when provided with ManNAc.

66. The isolated or purified cell of claim 65, which is an insect cell.

67. The insect cell of claim 66, wherein said insect cell is of a species selected from the group consisting of:
   (a) *Spodoptera frugiperda;*
   (b) *Trichoplusia ni;*
   (c) *Estigmena acrea*; and,
   (d) *Drosophila.*

68. The isolated or purified cell of claim 65, which is a yeast cell.

69. The isolated or purified cell of claim 65, which is a plant cell.

70. The isolated or purified cell of claim 65, which is a bacterial cell.

71. The isolated or purified cell of claim 65, which is a fungal cell.

72. The isolated or purified cell of claim 65, which is a mammalian cell.

73. The isolated or purified cell of claim 65, wherein the donor substrate CMP-SA is CMP-Neu5Ac (cytidine monophosphate-N-acetylneuraminic acid).

74. The isolated or purified cell of claim 65 wherein said CMP-sialic acid synthase gene and said sialic acid phosphate synthase gene are isolated from a human source.

75. The cell of claim 65 wherein said cell is provided with ManNAc by addition of ManNAc to media in which said cell is grown.

76. The cell of claim 65 wherein said cell is provided with ManNAc by genetically engineering said cell to catalyze synthesis of ManNAc.

77. The cell of claim 76, wherein said cell is genetically engineered to contain or express an epimerase that synthesizes ManNAc.

78. The cell of claim 77, wherein said epimerase is UDP-GlcNAc-2 epimerase.

79. The cell of claim 77, wherein said epimerase is GlcNAc-2 epimerase.

80. The cell of claim 65 wherein said cell also contains SA precursor GlcNAc above endogenous levels as a result of supplementation of cell growth medium with SA precursor GlcNAc.

81. An isolated or purified cell from a recombinant or genetically engineered cell line which contains and co-expresses
   i) a cytidine monophosphate-sialic acid (CMP-SA) synthase gene, wherein said CMP-SA-synthase gene encodes a polypeptide that catalyzes the formation of CMP-SA from SA and cytidine triphosphate (CTP), and wherein said polypepide is
      a) a polypeptide represented by SEQ ID NO:4 or
      b) a variant of the polypeptide represented by SEQ ID NO:4 that contains conservative amino acid substitutions and in which CMP-SA synthase structure and function are conserved; and
   ii) a sialic acid phosphate synthase (SAS) gene, wherein said SAS gene encodes a polypeptide that catalyzes the formation of sialic acid phosphate from N-acetylmannosamine (ManNAc) and phosphoeylpyruvate (PEP), and wherein polypeptide is
      a) a polypeptide represented by SEQ ID NO: 6; or
      b) a variant of the polypeptide represented by SEQ ID NO:6 that contains conservative amino acid substitutions and in which SAS structure and function are conserved; or
   c) a polypeptide represented by SEQ ID NO: 8; or
   d) a variant of the polypeptide represented by SEQ ID NO: 8 that contains conservative amino acid substitutions and in which SAS structure and function are conserved, said cell producing a donor substrate CMP-SA at a higher level than a cell from a parent cell line corresponding to said recombinant or genetically engineered cell line, wherein the donor substrate CMP-SA is CMP-KDN (cytidine monophosphate-2-keto-3-deoxy-D-glycero-D-galacto-nonoic acid).

82. The isolated or purified cell of claim 81, which is an insect cell.

83. The insect cell of claim 82, wherein said insect cell is of a species selected from the group consisting of:
   (a) *Spodoptera frugiperda;*
   (b) *Trichoplusia ni;*
   (c) *Estigmena acrea*; and,
   (d) *Drosophila.*

84. The isolated or purified cell of claim 81, which is a yeast cell.

85. The isolated or purified cell of claim 81, which is a plant cell.

86. The isolated or purified cell of claim 81, which is a bacterial cell.

87. The isolated or purified cell of claim 81, which is a fungal cell.

88. The isolated or purified cell of claim 81, which is a mammalian cell.

89. The isolated or purified cell of claim 81, wherein said CMP-sialic acid synthase gene and said sialic acid phosphate synthase gene are isolated from a human source.

90. An isolated or purified cell from a recombinant or genetically engineered cell line which contains and co-expresses
   i) a cytidine monophosphate-sialic acid (CMP-SA) synthase gene, wherein said CMP-SA synthase gene encodes a polypeptide that catalyzes the formation of CMP-SA from SA and cytidine triphosphate (CTP), and wherein said CMP-SA synthase gene comprises
      a) a nucleotide sequence represented by SEQ ID NO: 3, or
      b) a polynucleotide that hybridizes to the nucleotide sequence represented by SEQ ID NO:3 under stringent conditions, and
   ii) a sialic acid phosphate synthase gene wherein said SAS gene encodes a polypeptide that catalyzes the formation of sialic acid phosphate from N-acetylmannosamine (ManNAc) and phosphoeylpyruvate (PEP), and wherein said sialic acid phosphate synthase gene comprises
      a) a nucleotide sequence represented by SEQ ID NO: 5, or
      b) a polynucleotide that hybridizes to the nucleotide sequence represented by SEQ ID NO:5 under stringent conditions, said cell producing a donor substrate CMP-SA at a higher level than a cell from a parent cell line corresponding to said recombinant or genetically engineered cell line, wherein the donor substrate CMP-SA is CMP-KDN (cytidine monophosphate-2-keto-3-deoxy-D-glycero-D-galacto-nonoic acid).

91. The isolated or purified cell of claim 90, which is an insect cell.

92. The insect cell of claim 91, wherein said insect cell is of a species selected from the group consisting of:

(a) *Spodoptera frugiperda;*

(b) *Trichoplusia ni;*

(c) *Estigmena acrea;* and, (d) *Drosophila.*

93. The isolated or purified cell of claim 90, which is a yeast cell.

94. The isolated or purified cell of claim 90, which is a plant cell.

95. The isolated or purified cell of claim 90, which is a bacterial cell.

96. The isolated or purified cell of claim 90, which is a fungal cell.

97. The isolated or purified cell of claim 90, which is a mammalian cell.

98. The isolated or purified cell of claim 90, wherein said CMP-sialic acid synthase gene and said sialic acid phosphate synthase gene are isolated from a human source.

* * * * *

SEQUENCE LISTING

<160> NUMBER OF SEQ ID NOS: 18

<210> SEQ ID NO 1
<211> LENGTH: 1429
<212> TYPE: DNA
<213> ORGANISM: Homo sapiens

<400> SEQUENCE: 1

```
atggccttcc caaagaagaa acttcagggt cttgtggctg caaccatcac gccaatgact      60
gagaatggag aaatcaactt ttcagtaatt ggtcagtatg tggattatct tgtgaaagaa     120
cagggagtga agaacatttt tgtgaatggc acaacaggag aaggcctgtc cctgagcgtc     180
tcagagcgtc gccaggttgc agaggagtgg gtgacaaaag ggaaggacaa gctggatcag     240
gtgataattc acgtaggagc actgagcttg aaggagtcac aggaactggc ccaacatgca     300
gcagaaatag gagctgatgg catcgctgtc attgcaccgt tcttcctcaa gccatggacc     360
aaagatatcc tgattaattt cctaaaggaa gtggctgctg ccgcccctgc cctgccattt     420
tattactatc acattcctgc cttgacaggg gtaaagattc gtgctgagga gttgttggat     480
gggattctgg ataagatccc caccttccaa gggctgaaat tcagtgatac agatctctta     540
gacttcgggc aatgtgttga tcagaatcgc cagcaacagt ttgctttcct ttttggggtg     600
gatgagcaac tgttgagtgc tctggtgatg ggagcaactg gagcagtggg cagttttgta     660
tccagagatt tatcaacttt gttgtcaaac taggttttgg agtgtcacag accaaagcca     720
tcatgactct ggtctctggg attccaatgg gcccaccccg gcttccactg cagaaagcct     780
```

```
ccagggagtt tactgatagt gctgaagcta aactgaagag cctggatttc ctttctttca      840
ctgatttaaa ggatggaaac ttggaagctg gtagctagtg cctctctatc aaatcagggt      900
ttgcaccttg agacataatc taccttaaat agtgcattt ttctcaggg aatttttagat      960 gaacttgaat aaactctcct agcaaatgaa atctcacaat aagcattgag gtaccttttg     1020
tgagccttaa aaagtcttat tttgtgaagg ggcaaaaact ctaggagtca caactctcag     1080
tcattcattt cacagatttt tttgtggaga aatttctgtt tatatggatg aaatggaatc     1140
aagaggaaaa ttgtaattga ttaattccat ctgtctttag gagctctcat tatctcggtc     1200
tctggttcct aatcctattt taaagttgtc taattttaaa ccactataat atgtcttcat     1260
tttaataaat attcatttgg aatctaggaa aactctgagc tactgcattt aggcaggcac     1320
tttaatacca aactgtaaca tgtctcaact gtatacaact caaaatacac cagctcattt     1380
ggctgctcag tctaactcta gaatggatgc ttttgaattc atttcgatg                1429
```

```
<210> SEQ ID NO 2
<211> LENGTH: 304
<212> TYPE: PRT
<213> ORGANISM: Homo sapiens

<400> SEQUENCE: 2

Met Ala Phe Pro Lys Lys Leu Gln Gly Leu Val Ala Ala Thr Ile
1               5                  10                  15

Thr Pro Met Thr Glu Asn Gly Glu Ile Asn Phe Ser Val Ile Gly Gln
            20                  25                  30

Tyr Val Asp Tyr Leu Val Lys Glu Gln Gly Val Lys Asn Ile Phe Val
        35                  40                  45

Asn Gly Thr Thr Gly Glu Gly Leu Ser Leu Ser Val Ser Glu Arg Arg
    50                  55                  60

Gln Val Ala Glu Glu Trp Val Thr Lys Gly Lys Asp Lys Leu Asp Gln
65                  70                  75                  80

Val Ile Ile His Val Gly Ala Leu Ser Leu Lys Glu Ser Gln Glu Leu
                85                  90                  95

Ala Gln His Ala Ala Glu Ile Gly Ala Asp Gly Ile Ala Val Ile Ala
            100                 105                 110

Pro Phe Phe Leu Lys Pro Trp Thr Lys Asp Ile Leu Ile Asn Phe Leu
        115                 120                 125

Lys Glu Val Ala Ala Ala Ala Pro Ala Leu Pro Phe Tyr Tyr Tyr His
    130                 135                 140

Ile Pro Ala Leu Thr Gly Val Lys Ile Arg Ala Glu Glu Leu Leu Asp
145                 150                 155                 160

Gly Ile Leu Asp Lys Ile Pro Thr Phe Gln Gly Leu Lys Phe Ser Asp
                165                 170                 175

Thr Asp Leu Leu Asp Phe Gly Gln Cys Val Asp Gln Asn Arg Gln Gln
            180                 185                 190

Gln Phe Ala Phe Leu Phe Gly Val Asp Glu Gln Leu Leu Ser Ala Leu
        195                 200                 205

Val Met Gly Ala Thr Gly Ala Val Gly Ser Phe Val Ser Arg Asp Leu
    210                 215                 220

Ser Thr Leu Leu Ser Asn Val Leu Glu Cys His Arg Pro Lys Pro Ser
225                 230                 235                 240

Leu Trp Ser Leu Gly Phe Gln Trp Ala His Pro Gly Phe His Cys Arg
                245                 250                 255
```

```
        Lys Pro Pro Gly Ser Leu Leu Ile Val Leu Lys Leu Asn Arg Ala Trp
                    260                 265                 270

Ile Ser Phe Leu Ser Leu Ile Arg Met Glu Thr Trp Lys Leu Val Ala
                275                 280                 285

Ser Ala Ser Leu Ser Asn Gln Gly Phe Ala Pro Leu Arg His Asn Leu
            290                 295                 300

<210> SEQ ID NO 3
<211> LENGTH: 1305
<212> TYPE: DNA
<213> ORGANISM: Homo sapiens

<400> SEQUENCE: 3
atggactcgg tggagaaggg ggccgccacc tccgtctcca acccgcgggg gcgaccgtcc      60
cggggccggc cgccgaagct gcagcgcaac tctcgcggcg gccagggccg aggtgtggag     120
aagcccccgc acctggcagc cctaattctg gcccggggag gcagcaaagg catccccctg     180
aagaacatta agcacctggc gggggtcccg ctcattggct gggtcctgcg tgcggccctg     240
gattcagggg ccttccagag tgtatgggtt tcgacagacc atgatgaaat tgagaatgtg     300
gccaaacaat ttggtgcaca gttcatcga agaagttctg aagtttcaaa agacagctct     360
acctcactag atgccatcat agaatttctt aattatyata atgaggktga cattgtagga     420
aatattcaag ctacttctyc atgtttacat cctactgatc ttcaaaaagt tgcagaaatg     480
attcgagaag aaggatatga ttctgktttc tctgttgtga gacgccatca gtttcgatgg     540
agtgaaattc agaaaggagt tcgtgaagtg accgaacctc tgaatttaaa tccagctaaa     600
cggcctcgtc gacaagactg ggatggagaa ttatatgaaa atggctcatt ttattttgct     660
aaaagacatt tgatagagat gggttacttg cagggtggaa aaatggcata ctacgaaatg     720
cgagctgaac atagtgtgga tatagatgtg gatattgatt ggcctattgc agagcaaaga     780
gtattaagat atggctattt tggcaaagag aagcttaagg aaataaaact tttggtttgc     840
aatattgatg gatgtctcac caatggccac atttatgtat caggagacca aaaagaaata     900
atatcttatg atgtaaaaga tgctattggg ataagtttat taaagaaaag tggtattgag     960
gtgaggctaa tctcagaaag ggcctgttca agcagacgc tgtcttcttt aaaactggat    1020
tgcaaaatgg aagtcagtgt atcagacaag ctagcagttg tagatgaatg gagaaaagaa    1080
atgggcctgt gctggaaaga gtggcatat cttggaaatg aagtgtctga tgaagagtgc    1140
ttgaagagag tgggcctaag tggcgctcct gctgatgcct gttcctacgc ccagaaggct    1200
gttggataca tttgcaaatg taatggtggc cgtggtgcca tccgagaatt tgcagagcac    1260
atttgcctac taatggaaaa agttaataat tcatgccaaa aatag                    1305

<210> SEQ ID NO 4
<211> LENGTH: 434
<212> TYPE: PRT
<213> ORGANISM: Homo sapiens
<220> FEATURE:
<221> NAME/KEY: misc_feature
<222> LOCATION: (133)..(133)
<223> OTHER INFORMATION: Xaa can be any naturally occurring amino acid
<220> FEATURE:
<221> NAME/KEY: misc_feature
<222> LOCATION: (136)..(136)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
```

<221> NAME/KEY: misc_feature
<222> LOCATION: (169)..(169)
<223> OTHER INFORMATION: Xaa can be any naturally occurring amino acid

<400> SEQUENCE: 4

```
Met Asp Ser Val Glu Lys Gly Ala Ala Thr Ser Val Ser Asn Pro Arg
  1               5                  10                  15

Gly Arg Pro Ser Arg Gly Arg Pro Lys Leu Gln Arg Asn Ser Arg
                 20                  25                  30

Gly Gly Gln Gly Arg Gly Val Glu Lys Pro Pro His Leu Ala Ala Leu
             35                  40                  45

Ile Leu Ala Arg Gly Gly Ser Lys Gly Ile Pro Leu Lys Asn Ile Lys
         50                  55                  60

His Leu Ala Gly Val Pro Leu Ile Gly Trp Val Leu Arg Ala Ala Leu
 65                  70                  75                  80

Asp Ser Gly Ala Phe Gln Ser Val Trp Val Ser Thr Asp His Asp Glu
                     85                  90                  95

Ile Glu Asn Val Ala Lys Gln Phe Gly Ala Gln Val His Arg Arg Ser
                100                 105                 110

Ser Glu Val Ser Lys Asp Ser Ser Thr Ser Leu Asp Ala Ile Ile Glu
            115                 120                 125

Phe Leu Asn Tyr Xaa Asn Glu Xaa Asp Ile Val Gly Asn Ile Gln Ala
130                 135                 140

Thr Ser Xaa Cys Leu His Pro Thr Asp Leu Gln Lys Val Ala Glu Met
145                 150                 155                 160

Ile Arg Glu Glu Gly Tyr Asp Ser Xaa Phe Ser Val Val Arg His
                165                 170                 175

Gln Phe Arg Trp Ser Glu Ile Gln Lys Gly Val Arg Glu Val Thr Glu
                180                 185                 190

Pro Leu Asn Leu Asn Pro Ala Lys Arg Pro Arg Arg Gln Asp Trp Asp
                195                 200                 205

Gly Glu Leu Tyr Glu Asn Gly Ser Phe Tyr Phe Ala Lys Arg His Leu
            210                 215                 220

Ile Glu Met Gly Tyr Leu Gln Gly Gly Lys Met Ala Tyr Tyr Glu Met
225                 230                 235                 240

Arg Ala Glu His Ser Val Asp Ile Asp Val Asp Ile Asp Trp Pro Ile
                245                 250                 255

Ala Glu Gln Arg Val Leu Arg Tyr Gly Tyr Phe Gly Lys Glu Lys Leu
                260                 265                 270

Lys Glu Ile Lys Leu Leu Val Cys Asn Ile Asp Gly Cys Leu Thr Asn
            275                 280                 285

Gly His Ile Tyr Val Ser Gly Asp Gln Lys Glu Ile Ile Ser Tyr Asp
        290                 295                 300

Val Lys Asp Ala Ile Gly Ile Ser Leu Leu Lys Lys Ser Gly Ile Glu
305                 310                 315                 320

Val Arg Leu Ile Ser Glu Arg Ala Cys Ser Lys Gln Thr Leu Ser Ser
                325                 330                 335

Leu Lys Leu Asp Cys Lys Met Glu Val Ser Val Ser Asp Lys Leu Ala
                340                 345                 350

Val Val Asp Glu Trp Arg Lys Glu Met Gly Leu Cys Trp Lys Glu Val
                355                 360                 365

Ala Tyr Leu Gly Asn Glu Val Ser Asp Glu Glu Cys Leu Lys Arg Val
            370                 375                 380

Gly Leu Ser Gly Ala Pro Ala Asp Ala Cys Ser Tyr Ala Gln Lys Ala
```

```
                385           390           395           400
Val Gly Tyr Ile Cys Lys Cys Asn Gly Gly Arg Gly Ala Ile Arg Glu
                    405               410              415

Phe Ala Glu His Ile Cys Leu Leu Met Glu Lys Val Asn Asn Ser Cys
                420               425              430

Gln Lys

<210> SEQ ID NO 5
<211> LENGTH: 1080
<212> TYPE: DNA
<213> ORGANISM: Homo sapiens

<400> SEQUENCE: 5
atgccgctgg agctggagct gtgtcccggg cgctgggtgg gcgggcaaca cccgtgcttc      60
atcattgccg agatcggcca gaaccaccag ggcgacctgg acgtagccaa gcgcatgatc     120
cgcatggcca aggagtgtgg ggctgattgt gccaagttcc agaagagtga gctagaattc     180
aagtttaatc ggaaagcctt ggagaggcca tacacctcga agcattcctg ggggaagacg     240
tacggggagc acaaacgaca tctggagttc agccatgacc agtacaggga gctgcagagg     300
tacgccgagg aggttgggat cttcttcact gcctctggca tggatgagat ggcagttgaa     360
ttcctgcatg aactgaatgt tccatttttc aaagttggat ctggagacac taataatttt     420
ccttatctgg aaaagacagc caaaaaggt cgcccaatgg tgatctccag tgggatgcag     480
tcaatggaca ccatgaagca gtttatcag atcgtgaagc ccctcaaccc caacttctgc     540
ttcttgcagt gtaccagcgc atacccgctc cagcctgagg acgtcaacct gcgggtcatc     600
tcggaatatc agaagctctt tcctgacatt cccataggt attctgggca tgaaacaggc     660
atagcgatat ctgtggccgc agtggctctg ggggccaagg tgttggaacg tcacataact     720
ttggacaaga cctggaaggg gagtgaccac tcggcctcgc tggagcctgg agaactggcc     780
gagctggtgc ggtcagtgcg tcttgtggag cgtgccctgg gctccccaac caagcagctg     840
ctgccctgtg agatggcctg caatgagaag ctgggcaagt ctgtggtggc caaagtgaaa     900
attccggaag gcaccattct aacaatggac atgctcaccg tgaaggtggg tgagcccaaa     960
gcctatcctc ctgaagacat ctttaatcta gtgggcaaga aggtcctggt cactgttgaa    1020
gaggatgaca ccatcatgga agaattggta gataatcatg gcaaaaaaat caagtcttaa    1080

<210> SEQ ID NO 6
<211> LENGTH: 359
<212> TYPE: PRT
<213> ORGANISM: Homo sapiens

<400> SEQUENCE: 6

Met Pro Leu Glu Leu Glu Leu Cys Pro Gly Arg Trp Val Gly Gly Gln
1               5                   10                  15

His Pro Cys Phe Ile Ile Ala Glu Ile Gly Gln Asn His Gln Gly Asp
            20                  25                  30

Leu Asp Val Ala Lys Arg Met Ile Arg Met Ala Lys Glu Cys Gly Ala
        35                  40                  45

Asp Cys Ala Lys Phe Gln Lys Ser Glu Leu Glu Phe Lys Phe Asn Arg
    50                  55                  60

Lys Ala Leu Glu Arg Pro Tyr Thr Ser Lys His Ser Trp Gly Lys Thr
65                  70                  75                  80

Tyr Gly Glu His Lys Arg His Leu Glu Phe Ser His Asp Gln Tyr Arg
                85                  90                  95
```

```
Glu Leu Gln Arg Tyr Ala Glu Glu Val Gly Ile Phe Phe Thr Ala Ser
                100                 105                 110
Gly Met Asp Glu Met Ala Val Glu Phe Leu His Glu Leu Asn Val Pro
            115                 120                 125
Phe Phe Lys Val Gly Ser Gly Asp Thr Asn Asn Phe Pro Tyr Leu Glu
130                 135                 140
Lys Thr Ala Lys Lys Gly Arg Pro Met Val Ile Ser Ser Gly Met Gln
145                 150                 155                 160
Ser Met Asp Thr Met Lys Gln Val Tyr Gln Ile Val Lys Pro Leu Asn
                165                 170                 175
Pro Asn Phe Cys Phe Leu Gln Cys Thr Ser Ala Tyr Pro Leu Gln Pro
            180                 185                 190
Glu Asp Val Asn Leu Arg Val Ile Ser Glu Tyr Gln Lys Leu Phe Pro
        195                 200                 205
Asp Ile Pro Ile Gly Tyr Ser Gly His Glu Thr Gly Ile Ala Ile Ser
210                 215                 220
Val Ala Val Ala Leu Gly Ala Lys Val Leu Glu Arg His Ile Thr
225                 230                 235                 240
Leu Asp Lys Thr Trp Lys Gly Ser Asp His Ser Ala Ser Leu Glu Pro
                245                 250                 255
Gly Glu Leu Ala Glu Leu Val Arg Ser Val Arg Leu Val Glu Arg Ala
            260                 265                 270
Leu Gly Ser Pro Thr Lys Gln Leu Leu Pro Cys Glu Met Ala Cys Asn
275                 280                 285
Glu Lys Leu Gly Lys Ser Val Val Ala Lys Val Lys Ile Pro Glu Gly
        290                 295                 300
Thr Ile Leu Thr Met Asp Met Leu Thr Val Lys Val Gly Glu Pro Lys
305                 310                 315                 320
Ala Tyr Pro Pro Glu Asp Ile Phe Asn Leu Val Gly Lys Lys Val Leu
                325                 330                 335
Val Thr Val Glu Glu Asp Asp Thr Ile Met Glu Glu Leu Val Asp Asn
            340                 345                 350
His Gly Lys Lys Ile Lys Ser
        355

<210> SEQ ID NO 7
<211> LENGTH: 1059
<212> TYPE: DNA
<213> ORGANISM: Escherichia coli

<400> SEQUENCE: 7
atgagtaata tatatatcgt tgctgaaatt ggttgcaacc ataatggtag tgttgatatt      60
gcaagsagaa atgatattaa aagccaaaga ggccggtgtt aatgcagtaa aattccaaac     120
atttaaagct gataaattaa tttcagctat tgcacctaag gcagagtatc aaataaaaaa     180
cacaggagaa ttagaatctc agttagaaat gacaaaaaag cttgaaatga gtatgacga     240 ttatctccat ctaatggaat atgcagtcag tttaaattta gatgttttt ctaccccttt     300 tgacgaagac tctattgatt ttttagcatc tttgaaacaa aaaatatgga aaatcccttc     360
aggtgagtta ttgaatttac cgtatcttga aaaatagcc aagcttccga tccctgataa     420
gaaaataatc atatcaacag gaatggctac tattgatgag ataaaacagt ctgtttctat     480 tttttataaat aataaagttc cggttggtaa tattacaata ttcattgca atactgaata     540 tccaacgccc tttgaggatg taaaccttaa tgctattaat gatttgaaaa aacacttccc     600
```

-continued

```
taagaataac ataggcttct ctgatcattc tagcgggttt tatgcagcta ttgcggcggt      660
gccttatgga ataactttta ttgaaaaaca ttttacttta gataaatcta tgtctggccc      720
agatcatttg gcctcaatag aacctgatga actgaaacat ctttgtattg gggtcaggtg      780
tgttgaaaaa tctttaggtt caaatagtaa agtggttaca gcttcagaaa ggaagaataa      840
aatcgtagca agaaagtcta ttatagctaa acagagataa aaaaggtga ggttttttca       900 gaaaaaaata taacaacaaa aagacctggt aatggtatca gtccgatgga gtggtataat      960
ttattgggta aaattgcaga gcaagacttt attccagatg aattaataat tcatagcgaa      1020
ttcaaaaatc aggggaata atgagaacaa aaattattg                              1059
```

<210> SEQ ID NO 8
<211> LENGTH: 346
<212> TYPE: PRT
<213> ORGANISM: Escherichia coli

<400> SEQUENCE: 8

```
Met Ser Asn Ile Tyr Ile Val Ala Glu Ile Gly Cys Asn His Asn Gly
1               5                   10                  15

Ser Val Asp Ile Ala Arg Glu Met Ile Leu Lys Ala Lys Glu Ala Gly
                20                  25                  30

Val Asn Ala Val Lys Phe Gln Thr Phe Lys Ala Asp Lys Leu Ile Ser
            35                  40                  45

Ala Ile Ala Pro Lys Ala Glu Tyr Gln Ile Lys Asn Thr Gly Glu Leu
        50                  55                  60

Glu Ser Gln Leu Glu Met Thr Lys Lys Leu Glu Met Lys Tyr Asp Asp
65                  70                  75                  80

Tyr Leu His Leu Met Glu Tyr Ala Val Ser Leu Asn Leu Asp Val Phe
                85                  90                  95

Ser Thr Pro Phe Asp Glu Asp Ser Ile Asp Phe Leu Ala Ser Leu Lys
                100                 105                 110

Gln Lys Ile Trp Lys Ile Pro Ser Gly Glu Leu Leu Asn Leu Pro Tyr
            115                 120                 125

Leu Glu Lys Ile Ala Lys Leu Pro Ile Pro Asp Lys Lys Ile Ile Ile
        130                 135                 140

Ser Thr Gly Met Ala Thr Ile Asp Glu Ile Lys Gln Ser Val Ser Ile
145                 150                 155                 160

Phe Ile Asn Asn Lys Val Pro Val Gly Asn Ile Thr Ile Leu His Cys
                165                 170                 175

Asn Thr Glu Tyr Pro Thr Pro Phe Glu Asp Val Asn Leu Asn Ala Ile
                180                 185                 190

Asn Asp Leu Lys Lys His Phe Pro Lys Asn Asn Ile Gly Phe Ser Asp
            195                 200                 205

His Ser Ser Gly Phe Tyr Ala Ala Ile Ala Ala Val Pro Tyr Gly Ile
        210                 215                 220

Thr Phe Ile Glu Lys His Phe Thr Leu Asp Lys Ser Met Ser Gly Pro
225                 230                 235                 240

Asp His Leu Ala Ser Ile Glu Pro Asp Glu Leu Lys His Leu Cys Ile
                245                 250                 255

Gly Val Arg Cys Val Glu Lys Ser Leu Gly Ser Asn Ser Lys Val Val
                260                 265                 270

Thr Ala Ser Glu Arg Lys Asn Lys Ile Val Ala Arg Lys Ser Ile Ile
            275                 280                 285
```

```
Ala Lys Thr Glu Ile Lys Lys Gly Glu Val Phe Ser Glu Lys Asn Ile
    290                 295                 300

Thr Thr Lys Arg Pro Gly Asn Gly Ile Ser Pro Met Glu Trp Tyr Asn
305                 310                 315                 320

Leu Leu Gly Lys Ile Ala Glu Gln Asp Phe Ile Pro Asp Glu Leu Ile
                325                 330                 335

Ile His Ser Glu Phe Lys Asn Gln Gly Glu
            340                 345

<210> SEQ ID NO 9
<211> LENGTH: 20
<212> TYPE: DNA
<213> ORGANISM: Artificial
<220> FEATURE:
<223> OTHER INFORMATION: synthetic oligonucleotide primer: T/C, T, I,
      C,A,C/T,T,G,G,C,A,C/T,A/T/C,T,I,G,T,I,G,A
<220> FEATURE:
<221> NAME/KEY: misc_feature
<222> LOCATION: (1)..(1)
<223> OTHER INFORMATION: n = t or c
<220> FEATURE:
<221> NAME/KEY: misc_feature
<222> LOCATION: (3)..(3)
<223> OTHER INFORMATION: n = i
<220> FEATURE:
<221> NAME/KEY: misc_feature
<222> LOCATION: (6)..(6)
<223> OTHER INFORMATION: n = c or t
<220> FEATURE:
<221> NAME/KEY: misc_feature
<222> LOCATION: (12)..(12)
<223> OTHER INFORMATION: n = c or t
<220> FEATURE:
<221> NAME/KEY: misc_feature
<222> LOCATION: (13)..(13)
<223> OTHER INFORMATION: n = a, c or t
<220> FEATURE:
<221> NAME/KEY: misc_feature
<222> LOCATION: (15)..(15)
<223> OTHER INFORMATION: n = i
<220> FEATURE:
<221> NAME/KEY: misc_feature
<222> LOCATION: (18)..(18)
<223> OTHER INFORMATION: n = i

<400> SEQUENCE: 9
ntncantggc anntngtnga                                              20

<210> SEQ ID NO 10
<211> LENGTH: 20
<212> TYPE: DNA
<213> ORGANISM: Artificial
<220> FEATURE:
<223> OTHER INFORMATION: synthetic oligonucleotide primer
      G,A,G/A,A/T,T,A/C/T,G,A,C/T,I,I,I,C,C,I,G,G/C,I,C,A
<220> FEATURE:
<221> NAME/KEY: misc_feature
<222> LOCATION: (3)..(3)
<223> OTHER INFORMATION: n = g or a
<220> FEATURE:
<221> NAME/KEY: misc_feature
<222> LOCATION: (4)..(4)
<223> OTHER INFORMATION: n = a or t
<220> FEATURE:
<221> NAME/KEY: misc_feature
<222> LOCATION: (6)..(6)
<223> OTHER INFORMATION: n = a,c or t
<220> FEATURE:
<221> NAME/KEY: misc_feature
<222> LOCATION: (9)..(9)
<223> OTHER INFORMATION: n = c or t
<220> FEATURE:
<221> NAME/KEY: misc_feature
```

```
<222> LOCATION: (10)..(10)
<223> OTHER INFORMATION: n = i
<220> FEATURE:
<221> NAME/KEY: misc_feature
<222> LOCATION: (11)..(11)
<223> OTHER INFORMATION: n = i
<220> FEATURE:
<221> NAME/KEY: misc_feature
<222> LOCATION: (12)..(12)
<223> OTHER INFORMATION: n = i
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n = g or c
<220> FEATURE:
<221> NAME/KEY: misc_feature
<222> LOCATION: (18)..(18)
<223> OTHER INFORMATION: n = i

<400> SEQUENCE: 10
ganntngann nnccngnnca                                           20

<210> SEQ ID NO 11
<211> LENGTH: 20
<212> TYPE: DNA
<213> ORGANISM: Artificial
<220> FEATURE:
<223> OTHER INFORMATION: synthetic oligonucleotide primer
     T,G,I,C/G,C,I,G,G,I,I,I,G/A,T,C,T/G/A,A,T/A,C/T,T,C
<220> FEATURE:
<221> NAME/KEY: misc_feature
<222> LOCATION: (3)..(3)
<223> OTHER INFORMATION: n = i
<220> FEATURE:
<221> NAME/KEY: misc_feature
<222> LOCATION: (4)..(4)
<223> OTHER INFORMATION: n = c or g
<220> FEATURE:
<221> NAME/KEY: misc_feature
<222> LOCATION: (6)..(6)
<223> OTHER INFORMATION: n = i
<220> FEATURE:
<221> NAME/KEY: misc_feature
<222> LOCATION: (9)..(9)
<223> OTHER INFORMATION: n = i
<220> FEATURE:
<221> NAME/KEY: misc_feature
<222> LOCATION: (10)..(10)
<223> OTHER INFORMATION: n = i
<220> FEATURE:
<221> NAME/KEY: misc_feature
<222> LOCATION: (11)..(11)
<223> OTHER INFORMATION: n = i
<220> FEATURE:
<221> NAME/KEY: misc_feature
<222> LOCATION: (12)..(12)
<223> OTHER INFORMATION: n = g or a
<220> FEATURE:
<221> NAME/KEY: misc_feature
<222> LOCATION: (15)..(25)
<223> OTHER INFORMATION: n = t, g or a
<220> FEATURE:
<221> NAME/KEY: misc_feature
<222> LOCATION: (17)..(17)
<223> OTHER INFORMATION: n = t or a
<220> FEATURE:
<221> NAME/KEY: misc_feature
<222> LOCATION: (18)..(18)
<223> OTHER INFORMATION: n = c or t

<400> SEQUENCE: 11
tgnncnggnn nntcnanntc                                           20
```

<210> SEQ ID NO 12
<211> LENGTH: 20
<212> TYPE: DNA
<213> ORGANISM: Artificial
<220> FEATURE:
<223> OTHER INFORMATION: synthetic oligonucleotide primer A, C/A/G, C/T,
    T,C,G/A,T,C,I,C,C,I,C,C,I,I,I,G/A,T,G
<220> FEATURE:
<221> NAME/KEY: misc_feature
<222> LOCATION: (2)..(2)
<223> OTHER INFORMATION: n = c, a or g
<220> FEATURE:
<221> NAME/KEY: misc_feature
<222> LOCATION: (3)..(3)
<223> OTHER INFORMATION: n = c or t
<220> FEATURE:
<221> NAME/KEY: misc_feature
<222> LOCATION: (6)..(6)
<223> OTHER INFORMATION: n = g or a
<220> FEATURE:
<221> NAME/KEY: misc_feature
<222> LOCATION: (9)..(9)
<223> OTHER INFORMATION: n = i
<220> FEATURE:
<221> NAME/KEY: misc_feature
<222> LOCATION: (12)..(12)
<223> OTHER INFORMATION: n = i
<220> FEATURE:
<221> NAME/KEY: misc_feature
<222> LOCATION: (15)..(15)
<223> OTHER INFORMATION: n = i
<220> FEATURE:
<221> NAME/KEY: misc_feature
<222> LOCATION: (16)..(16)
<223> OTHER INFORMATION: n = i
<220> FEATURE:
<221> NAME/KEY: misc_feature
<222> LOCATION: (17)..(17)
<223> OTHER INFORMATION: n = i
<220> FEATURE:
<221> NAME/KEY: misc_feature
<222> LOCATION: (18)..(18)
<223> OTHER INFORMATION: n = g or a

<400> SEQUENCE: 12
anntcntcnc cnccnnnntg                                            20

<210> SEQ ID NO 13
<211> LENGTH: 54
<212> TYPE: DNA
<213> ORGANISM: Artificial
<220> FEATURE:
<223> OTHER INFORMATION: synthetic oligonucleotide primer

<400> SEQUENCE: 13
tgtaatacga ctcactatag ggcggatccg ccatcatgcc gctggagctg gagc       54

<210> SEQ ID NO 14
<211> LENGTH: 34
<212> TYPE: DNA
<213> ORGANISM: Artificial
<220> FEATURE:
<223> OTHER INFORMATION: synthetic oligonucleotide primer

<400> SEQUENCE: 14
gtacggtacc ttattaagac ttgattttttt tgcc                            34

<210> SEQ ID NO 15
<211> LENGTH: 54
<212> TYPE: DNA
<213> ORGANISM: Artificial

```
<220> FEATURE:
<223> OTHER INFORMATION: synthetic oligonucleotide primer

<400> SEQUENCE: 15
tgtaatacga ctcactatag ggcggatccg ccatcatgga ctcggtggag aagg          54

<210> SEQ ID NO 16
<211> LENGTH: 44
<212> TYPE: DNA
<213> ORGANISM: Artificial
<220> FEATURE:
<223> OTHER INFORMATION: synthetic oligonucleotide primer

<400> SEQUENCE: 16
gtacggtacc ttactatttt tggcatgaat tattaacttt ttcc                    44

<210> SEQ ID NO 17
<211> LENGTH: 14
<212> TYPE: PRT
<213> ORGANISM: Escherichia coli

<400> SEQUENCE: 17

Ile Ile Ala Ile Ile Pro Ala Arg Ser Gly Ser Lys Gly Leu
1               5                   10

<210> SEQ ID NO 18
<211> LENGTH: 14
<212> TYPE: PRT
<213> ORGANISM: Homo sapiens

<400> SEQUENCE: 18

Leu Ala Ala Leu Ile Leu Ala Arg Gly Gly Ser Lys Gly Ile
1               5                   10
```